(12) United States Patent
Hatamian

(10) Patent No.: US 11,175,303 B2
(45) Date of Patent: Nov. 16, 2021

(54) AUTOMATED MEDICAL SAMPLE COLLECTION AND TESTING FOR PROVIDING BLOOD COAGULATION INDICATION

(71) Applicant: 2Pi-Sigma Corp., Newport Beach, CA (US)

(72) Inventor: Mehdi Hatamian, Mission Viejo, CA (US)

(73) Assignee: 2Pi-Sigma Corp., Newport Beach, CA (US)

(*) Notice: Subject to any disclaimer, the term of this patent is extended or adjusted under 35 U.S.C. 154(b) by 30 days.

(21) Appl. No.: 16/664,746

(22) Filed: Oct. 25, 2019

(65) Prior Publication Data

US 2020/0057086 A1 Feb. 20, 2020

Related U.S. Application Data

(63) Continuation-in-part of application No. 15/954,442, filed on Apr. 16, 2018, now Pat. No. 10,791,972.
(Continued)

(51) Int. Cl.
*G01N 35/10* (2006.01)
*G01N 33/49* (2006.01)
*G01N 35/00* (2006.01)

(52) U.S. Cl.
CPC ..... *G01N 35/1095* (2013.01); *G01N 33/4905* (2013.01); *G01N 35/00584* (2013.01)

(58) Field of Classification Search
None
See application file for complete search history.

(56) References Cited

U.S. PATENT DOCUMENTS 4,031,399 A 6/1977 Klein et al.
5,502,651 A * 3/1996 Jackson ............. G01N 21/82
356/39

(Continued)

FOREIGN PATENT DOCUMENTS

WO WO 2011/029794 3/2011
WO WO 2016/025843 2/2016
WO WO 2018/195544 10/2018

OTHER PUBLICATIONS

Portions of prosecution history of U.S. Appl. No. 15/785,755, Apr. 27, 2020, Hatamian, Mehdi.
(Continued)

*Primary Examiner* — Matthew D Krcha
(74) *Attorney, Agent, or Firm* — Makoui Law, PC; Ali Makoui

(57) ABSTRACT

A sample collection and testing device for analyzing blood is provided that includes a controller, a fluid flow pathway, a pump configured to move fluid through the fluid pathway, and an optical fluid measurement element configured to measure a light intensity of the fluid in the fluid flow pathway. The controller is configured to: start the pump to move a blood sample in the fluid flow pathway, receive a signal from the optical fluid measurement element indicating a detection of a leading edge of the blood in the fluid flow pathway, stop the pump to stop the moving of the blood in the pathway, receive a plurality of light intensity measurements from the optical measurement element, each light intensity measurement measured at a corresponding point of time, and provide a mapping of the light intensity measurements into an indication of a coagulation of the blood sample over a time period.

19 Claims, 29 Drawing Sheets

Related U.S. Application Data which is a continuation-in-part of application No. 15/785,755, filed on Oct. 17, 2017, now Pat. No. 10,928,411.

(60) Provisional application No. 62/488,174, filed on Apr. 21, 2017.

(56) References Cited

U.S. PATENT DOCUMENTS

| | | | |
|---|---|---|---|
| 5,662,127 | A | 9/1997 | De Vaughn |
| 5,916,230 | A | 6/1999 | Brenneman et al. |
| 5,971,941 | A | 10/1999 | Simons et al. |
| 6,506,165 | B1 | 1/2003 | Sweeney |
| 6,506,168 | B1* | 1/2003 | Fathallah .............. A61B 5/157 |
| | | | 600/578 |
| 6,770,190 | B1 | 8/2004 | Milanovski et al. |
| 7,374,949 | B2 | 5/2008 | Kuriger |
| 8,413,886 | B2 | 4/2013 | Creaven et al. |
| 2003/0067599 | A1 | 4/2003 | Carrillo |
| 2003/0083685 | A1 | 5/2003 | Freeman et al. |
| 2003/0136183 | A1* | 7/2003 | Neel ................. G01N 21/0303 |
| | | | 73/53.01 |
| 2004/0173456 | A1 | 9/2004 | Boos et al. |
| 2005/0032204 | A1 | 2/2005 | Rodgers et al. |
| 2005/0130292 | A1 | 6/2005 | Ahn et al. |
| 2005/0208648 | A1 | 9/2005 | Sage et al. |
| 2006/0068490 | A1 | 3/2006 | Tang et al. |
| 2008/0077048 | A1 | 3/2008 | Escutia et al. |
| 2008/0082117 | A1 | 4/2008 | Ruf |
| 2008/0194987 | A1 | 8/2008 | Boecker |
| 2008/0194988 | A1 | 8/2008 | Nakamura et al. |
| 2008/0297169 | A1 | 12/2008 | Greenquist et al. |
| 2009/0269837 | A1 | 10/2009 | Shevkoplyas et al. |
| 2009/0298097 | A1 | 12/2009 | Harris et al. |
| 2010/0045267 | A1 | 2/2010 | Dittmer et al. |
| 2010/0196207 | A1 | 8/2010 | Steinmiller et al. |
| 2011/0053289 | A1 | 3/2011 | Lowe et al. |
| 2011/0137208 | A1 | 6/2011 | Valk et al. |
| 2011/0201312 | A1 | 8/2011 | Peterson et al. |
| 2012/0208283 | A1 | 8/2012 | Gheorghiu et al. |
| 2012/0301967 | A1* | 11/2012 | Nadkarni ........... G01N 33/4905 |
| | | | 436/69 |
| 2013/0114075 | A1* | 5/2013 | Hukari .................. B01L 9/527 |
| | | | 356/246 |
| 2013/0158432 | A1 | 6/2013 | Escutia et al. |
| 2013/0309778 | A1 | 11/2013 | Lowe et al. |
| 2014/0295433 | A1 | 10/2014 | Chen et al. |
| 2014/0378800 | A1 | 12/2014 | Richter et al. |
| 2015/0377814 | A1 | 12/2015 | Schindelholz et al. |
| 2017/0016753 | A1 | 1/2017 | Shi et al. |
| 2018/0303385 | A1 | 10/2018 | Hatamian et al. |
| 2018/0303390 | A1 | 10/2018 | Hatamian |
| 2018/0306831 | A1 | 10/2018 | Hatamian |
| 2018/0310863 | A1 | 11/2018 | Hatamian |
| 2020/0054260 | A1 | 2/2020 | Hatamian |

OTHER PUBLICATIONS

Portions of prosecution history of U.S. Appl. No. 15/954,442, Jul. 1, 2020, Hatamian, Mehdi.

Portions of prosecution history of U.S. Appl. No. 15/959,555, Jul. 14, 2020, Hatamian, Mehdi, et al.

Portions of prosecution history of U.S. Appl. No. 15/959,576, Jul. 15, 2020, Hatamian, Mehdi.

International Written Opinion of PCT/US18/28913, dated May 10, 2018, 2Pi-Sigma Corp.

International Search Report of PCT/US18/28913, dated May 10, 2018, 2Pi-Sigma Corp.

International Preliminary Search Report of PCT/US18/28913, dated Oct. 22, 2019, 2Pi-Sigma Corp.

* cited by examiner

AUTOMATED MEDICAL SAMPLE COLLECTION AND TESTING FOR PROVIDING BLOOD COAGULATION INDICATION

CROSS-REFERENCE TO RELATED APPLICATIONS

This application is a continuation-in-part of U.S. patent application Ser. No. 15/954,442, filed on Apr. 16, 2018, published as U.S. Patent Publication 2018/0303390. U.S. patent application Ser. No. 15/954,442 is a continuation-in-part of U.S. patent application Ser. No. 15/785,755, filed on Oct. 17, 2017, published as U.S. Patent Publication 2018/0306831. U.S. patent application Ser. No. 15/785,755 claims priority to U.S. Provisional Patent Application Ser. No. 62/488,174, filed on Apr. 21, 2017. The contents of U.S. patent application Ser. No. 15/954,442, published as U.S. Patent Publication 2018/0303390, is hereby incorporated by reference.

BACKGROUND

Many users, whether professional or home-based, may wish to take blood samples (and/or other fluid samples) on a regular basis. For instance, people with type I diabetes may need to measure blood sugar at least four times per day.

Existing sampling methods require users to manually prick a fingertip to generate and collect a sample for testing. Such sampling results in inconsistent sample quantities, stress and anxiety for the subject, potential for sample contamination, and/or other issues related to manual collection and processing.

Furthermore, after generating a sample, a subject may need to perform additional operations such as collecting the sample, applying the sample to a test strip, inserting the strip into a testing device, etc.

In addition, as collection may be performed frequently, subjects may wish to collect the minimum sample needed for testing.

Thus there is a need for a way to accurately measure small volumes of collected samples.

SUMMARY

A sample collection and testing device (SCTD) of some embodiments may be able to collect a sample from a test subject. The SCTD may utilize removable cartridges. Such cartridges (or portions thereof) may be intended for single use.

Some embodiments are able to automatically collect a blood sample from a subject's finger. Such sample collection may involve detection of the subject (or finger in this example), piercing or pricking of the subject, collection, and/or storage of the sample. Although blood is used as one example, various other fluids may be collected and/or analyzed.

The sample may be collected via a receptacle (e.g., a recess in a surface of the cartridge) using a pump, valve, fluid sensing chip, tubing or other flow pathways, storage cavities, and/or other appropriate features.

A piercing element of some embodiments may include a needle and spring, actuator, and/or other appropriate elements. The piercing element may be automatically extended an appropriate amount to draw blood through the skin in this example. The amount of extension may be specified and/or limited in various appropriate ways (e.g., physical or mechanical barriers or stops, a value associated with the actuator extension, etc.). The extension may be set by a user, may be based on default values, or may be determined automatically using various sensors associated with the SCTD and/or cartridge.

In some embodiments, a fluid sensing device (and/or other elements of the cartridge) may include and/or be at least partially enclosed in a flexible material (e.g., silicone). Such enclosed elements may come into contact with the sample fluid and thus be intended to be single use or disposable. Other elements, such as the piercing element, that come into contact with the sample fluid may also be included in a disposable cartridge (or disposable portion thereof). Throughout the specification, any reference to "disposable" elements or components indicates single use components (e.g., components that will directly contact a blood sample).

Some embodiments may include non-contact sensing elements such that the fluid sensing device is able to be reused. Such non-contact elements may include, for instance, embedded sensors or leads that are able to be accessed via terminals along an outer surface of the cartridge. In some embodiments, the sensing elements may be able to sense properties of the sample through the enclosure without use of any exposed leads or contacts.

The non-contact elements may include fluid measurement features in some embodiments. The fluid measurement features may include optical measurement elements that are able to detect and measure properties associated with fluid samples. Such measurements may include, for example, volume, viscosity or flow rate, color density or saturation, etc.

One example cartridge may be able to perform a test for cancer using human aspartyl (asparaginyl) β-hydroxylase (HAAH) protein and its associated antibodies. Such a cartridge may utilize magnetic beads and charge detection to evaluate samples.

Some embodiments of the SCTD (and/or associated cartridges) may be able to measure small amounts of fluid using optical components such as lasers, LED lights sources, and/or other optical components to detect fluid within a transparent or semi-transparent fluid pathway.

The preceding Summary is intended to serve as a brief introduction to various features of some exemplary embodiments. Other embodiments may be implemented in other specific forms without departing from the scope of the disclosure.

BRIEF DESCRIPTION OF THE SEVERAL VIEWS OF THE DRAWINGS

The exemplary features of the disclosure are set forth in the appended claims. However, for purpose of explanation, several embodiments are illustrated in the following drawings.

DETAILED DESCRIPTION

The following detailed description describes currently contemplated modes of carrying out exemplary embodiments. The description is not to be taken in a limiting sense, but is made merely for the purpose of illustrating the general principles of some embodiments, as the scope of the disclosure is best defined by the appended claims.

Various features are described below that can each be used independently of one another or in combination with other features. Broadly, some embodiments generally provide an automated sample collection and testing device (SCTD).

Some embodiments may include optical measurement elements that are able to measure attributes of fluid within a flow pathway of some embodiments. The attributes may include, for instance, verification of fluid presence, volume, flow rate, color saturation, etc.

A first exemplary embodiment provides an optical fluid measurement element comprising: an emitter that generates an optical output; an absorber that measures an optical input; and a fluid flow pathway, wherein the optical output of the emitter passes through a portion of the fluid flow pathway and is received as the optical input to the absorber after passing through the portion of the fluid flow pathway.

A second exemplary embodiment provides an automated method of measuring fluid volume using an optical fluid measurement element, the method comprising: activating an emitter of the optical fluid measurement element; capturing data from an optical sensor of the optical fluid measurement element; detecting a leading edge of fluid travelling along a flow pathway based on the data captured from the optical sensor; starting a counter when the leading edge is detected; and calculating a volume based on a value of the counter.

A third exemplary embodiment provides an automated method of measuring fluid attributes along a flow pathway, the method comprising: activating an optical emitter; receiving a signal from an optical sensor, the signal based on an amount of light received from the optical emitter, wherein the flow pathway is between the optical emitter and the optical sensor; and processing the received signal to determine at least one fluid attribute.

Several more detailed embodiments are described in the sections below. Section I provides a description of hardware architectures of some embodiments. Section II then describes various methods of operation of some embodiments. Lastly, Section III describes a computer system which implements some of the embodiments.

I. Hardware Architecture

Figure 1:
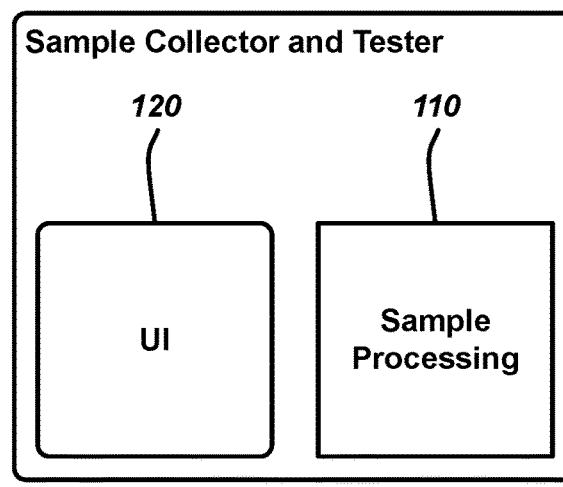
FIG. 1 illustrates a top view of an automated sample collection and testing device according to an exemplary embodiment.

FIG. 1 illustrates a top view of an automated SCTD 100 according to an exemplary embodiment. As shown, the device may include a removable test sample processing module 110, various user interface (UI) features 120, such as buttons, displays, touchscreens, keypads, LEDs, etc., and a housing 130.

The sample processing module 110 will be described in more detail in reference to FIG. 2 below. The housing 130 may be able to sit flat on a surface such as a tabletop or counter. The housing may include receptacles, sockets, etc. that may allow the housing to be attached to various elements, as appropriate (e.g., stands, carts, etc.). The housing may include various mechanical features (e.g., a cartridge release lever and associated mechanism, a hinged lid or door that provides access to elements within the housing, etc.).

Figure 2:
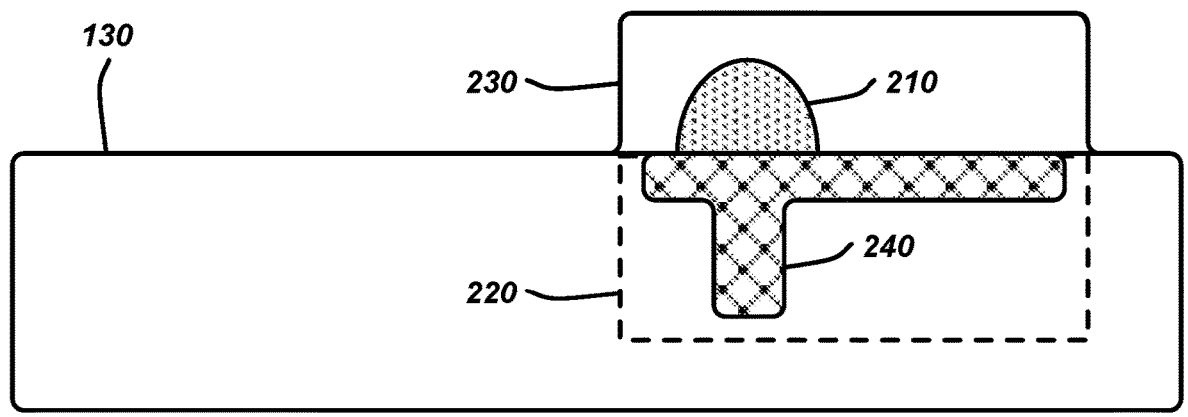
FIG. 2 illustrates a front elevation view of the automated sample collection and testing device of FIG. 1.

FIG. 2 illustrates a front elevation view of the automated sample collection and testing device 100. As shown, the sample processing module 110 of this example includes a receptacle 210 sized and shaped appropriately for a human finger, a bottom portion 220, a top portion 230, and a disposable cartridge 240 (or cavity if no cartridge has been inserted) that is able to be added to or removed from the sample processing module 110. In this example, the top portion 230 may include a hinge such that the top portion may be pulled away from the bottom portion to expose the cartridge 240 (or cavity).

Figure 3:
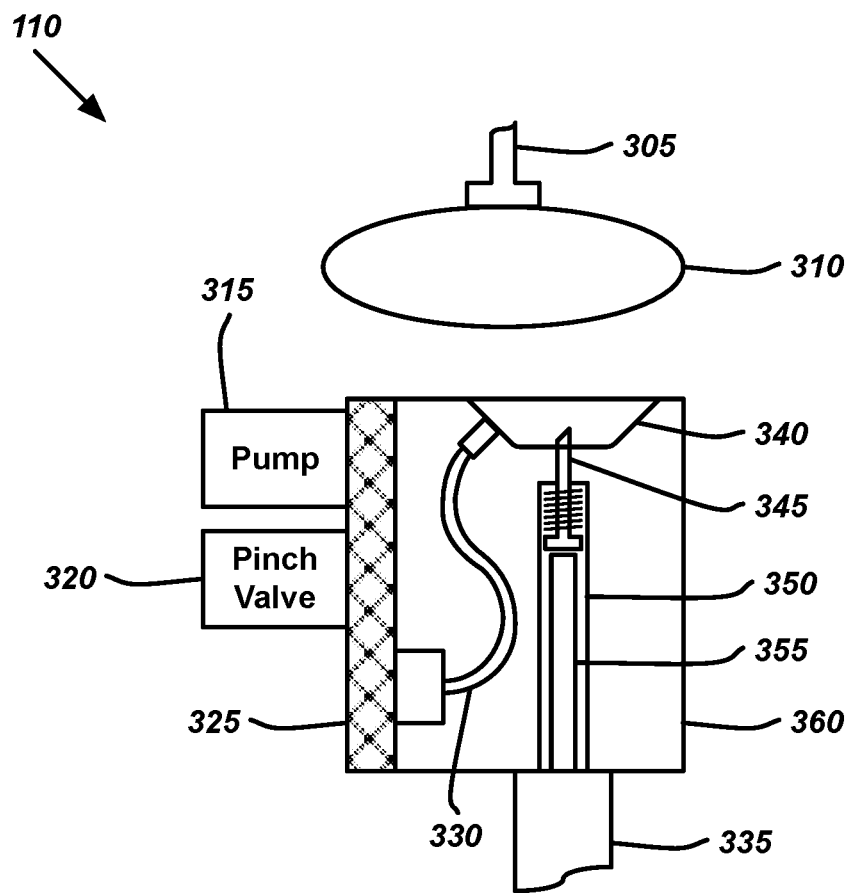
FIG. 3 illustrates a side elevation view of an exemplary embodiment of a sample processing module included in the sample collection and testing device of FIG. 1.

FIG. 3 illustrates a side elevation view of an exemplary embodiment of the sample processing module 110, showing various internal components of the cartridge. As shown, the cartridge may include a rubber pump 305, retention element 310, sample pump 315, pinch valve 320, chip 325, tubing or other connectors 330, an actuator 335, a receptacle 340, needle and spring 345, needle housing 350, needle connector 355, and cartridge housing 360.

In this example, elements 325-330 and 340-360 may typically be included in the disposable cartridge portion 240 of the sample processing module 110, while the other components may be included in a reusable portion of the sample processing module 110 or otherwise included in the SCTD 100.

The rubber pump 305 may be a device capable of pumping fluid (e.g., air) into the retention element 310. The fluid may be in a liquid and/or gaseous form. The retention element 310 may be a balloon or flexible bladder that is able to accept an appropriate amount of fluid and, in turn, provide adjustable resistance to pressure.

The sample pump 315 may be a pump capable of moving fluid along a pathway. In some embodiments, the sample pump may be associated with a measurement element or meter (not shown) that is able to determine an amount of fluid moved by the pump. The pinch valve 320 may be a controllable valve capable of permitting or restraining fluid flow within the sample processing module 110.

The "chip" 325 or fluid sensing plate may be able to store and/or interact with various fluids (e.g., sample fluids, reactants, catalysts, etc.). The chip may include electronic circuitry (e.g., sensors, integrated circuits, etc.) that may be able to detect or measure attributes of the fluid(s) and generate signals that provide the measured attributes to other components (e.g., a processor).

Some embodiments may include a fluid sensing plate that is reusable across multiple samples. Such a plate may either contact a sample indirectly (e.g., using disposable probes that are part of the cartridge and are able to provide electrical connection via some external connectors to the device 100). In some embodiments, the plate may be completely non-contact and sense fluid attributes through a silicone membrane or other appropriate cartridge material.

The tubing or other connectors 330 may allow fluid flow among the elements of the sample processing module 110. In some embodiments, the tubing 330 may be formed by cavities within a solid element. For instance, in some embodiments, the chip 325, tubing 330, and receptacle 340 may be included in cube-shaped silicone.

The actuator 335 may be able to apply force to the connector 355. The actuator 335 may be able to extend and retract the connector 355. The actuator 335 may include components such as a linear solenoid, a rotary motor, etc. In some embodiments, the actuator may be controllable such that attributes such as depth or height, pressure, velocity, acceleration, torque, etc. may be able to be controlled based on various parameters (e.g., default values, user selections, measured values, etc.).

The receptacle 340 may include a recess or tub appropriate for placement of a finger in this example. Different embodiments may include different receptacles. For instance, some embodiments may include a connector that allows vials or other containers (e.g., micro tubes or other industry standard micro containers) to be coupled to the sample processing module 110. In some embodiments, the fluid may be collected and tested at the receptacle 340. For instance, a droplet of blood from a fingertip may be applied to a paper test strip located at the receptacle. In some embodiments, a micro tube or other container may be removed (after a sample has been collected) and sent elsewhere for testing (or attached to another testing device).

The extendable and retractable needle and spring 345 (or other piercing element such as a blade) may be able to extend out into the receptacle 340 such that a sample may be taken. The spring may cause the needle 345 to automatically retract when pressure is released from the actuator 335. The height and/or other attributes of the needle 345 may be adjusted manually or electronically (e.g., using actuators). For instance, some embodiments may include a physical knob that may allow users to adjust the height of housing 350, thereby controlling the maximum extension of the needle 345.

As another example, some embodiments may allow a desired height or extension of the needle 345 to be entered using a UI element or external device. Such desired height may be set in relative (e.g., discrete values from one to ten) or absolute terms (e.g., height in millimeters). The desired height may be used to control the operation of the actuator 335 to control the extension of the needle 345. Some embodiments may include various sensors that may automatically determine a desired height and apply such determined height to the operation of the needle 345. Such adjustment parameters may be stored such that a user may collect additional samples once comfortable needle use has been achieved.

The needle housing 350 may be a rigid hollow column. In this example, the housing is associated with a round needle and spring 345 and a cylindrical connector 355. Different embodiments may have elements with different shapes, based on the particular application.

The needle connector 355 may be a rigid member that couples the actuator 335 to the needle 345 such that the extension (or retraction) of the actuator 335 causes the needle 345 to be extended (or retracted).

The cartridge housing 360 in this example has a cube shape. The housing may include multiple portions. Some embodiments may include hinges, latches, etc. that may couple the portions. The housing may include various interfaces for use with the SCTD 100. Such interfaces may include, for instance, sockets or other connectors, terminals, wireless communication interfaces, etc.

During use, a subject's finger may be retained using the rubber pump 305 and balloon 310. The punching needle and associated spring 345 may be manipulated by the actuator 335 via the connector 355 to pierce the subject's finger and a blood sample may be collected using the chip 325, pinch valve 320, pump 315, and collection receptacle 340 under the finger. In addition, various tubes, connectors, etc. 330 may be utilized to transport fluid from the collection receptacle 340 to the chip 325.

The pressure of the balloon 310 (or other retaining element) may be adjustable. Such pressure may be set to retain the finger in place without causing a feeling that the finger is trapped or any other discomfort. Such a pressure adjustment may utilize various appropriate UI elements, including, for instance, up/down buttons, touchscreen features, received command from an external device, etc. Such adjustments may be stored for future use by a particular subject.

In this example, the sample processing module 110 includes automated collection and processing. Some embodiments may be able to receive a cartridge that includes a previously collected sample (e.g., held in a microtube). Such embodiments may be able to pierce (and/or otherwise interact with) the microtube in order to retrieve and analyze the collected sample.

Some embodiments may include at least one flowmeter. Such a flowmeter may follow the collection point in order to monitor the flow of fluid and/or measure volume. Such elements may be omitted in some embodiments in order to reduce cost of the sample processing module 110 (or disposable portions thereof).

In some embodiments, the SCTD 100 may automatically detect the finger and activate the device. Some embodiments may include a manual control such as a button or touchscreen 120 that can be used to activate the device 100. Such a control may be received as a command message from an external user device.

Figure 4:
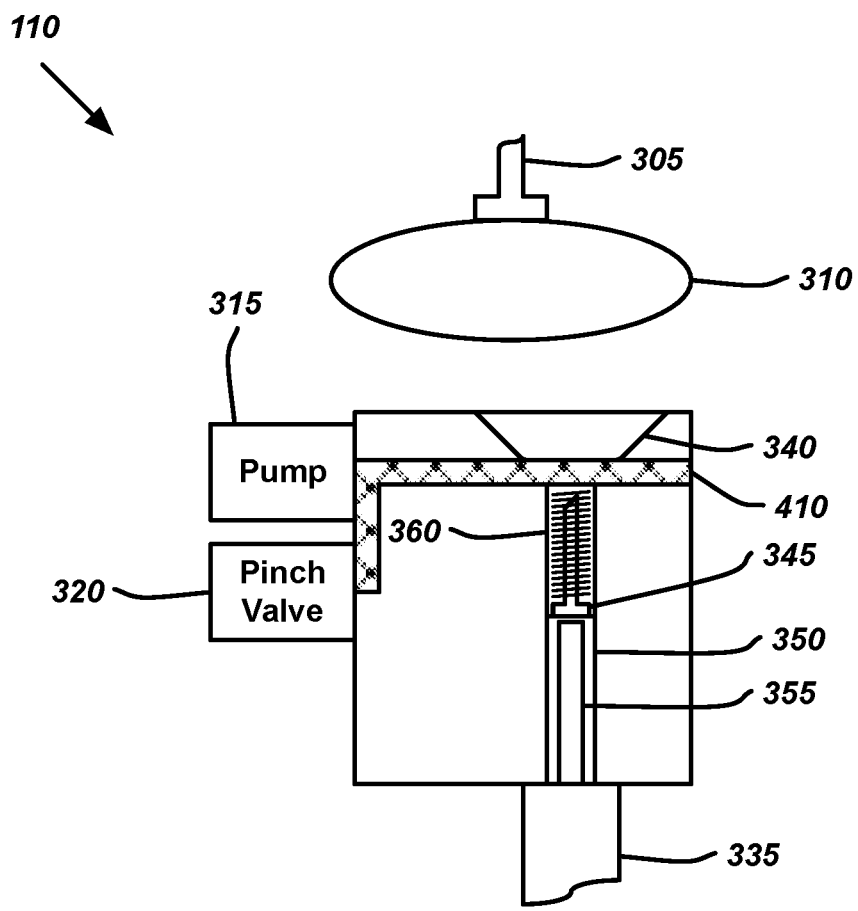
FIG. 4 illustrates a side elevation view of another exemplary embodiment of the sample processing module included in the sample collection and testing device of FIG. 1.

FIG. 4 illustrates a side elevation view of another exemplary embodiment of the sample processing module 110. In this example, the chip 410 may be located at the sample collection point (e.g., receptacle 340 where the finger is placed). The chip 410 may be made from a flexible material such as silicone. In such embodiments, the needle 345 may be placed below the chip 410 and pierce the chip 410 before pricking the finger. The material may then seal itself after the needle 345 is retracted such that the blood is retained within the chip or sample collection cavity 410. In this example, the needle 345 is in a fully retracted position whereas in the example of FIG. 3, the needle was in a partially or fully extended state.

In this example, the needle housing 350 may be split into two portions (a top portion and a bottom portion from this view), where one portion (i.e., the top portion in this example) is included in the disposable insert 360 of some embodiments. Other components may be included in the disposable insert, such as the needle and spring 345, the chip 410, and the receptacle 340. As above, any electronic sensing plate may be included in the removable cartridge 360 along with the chip 410 or may be included with the non-disposable components.

In the examples of FIG. 3 and FIG. 4, different embodiments may include different components within the disposable cartridge of some embodiments. Likewise, various different components may be included within the non-disposable elements of the device 100. Such components may be distributed among the disposable and non-disposable portions based on various relevant criteria (e.g., component cost, availability of components, cartridge footprint, device sensing capabilities, etc.).

Figure 5:
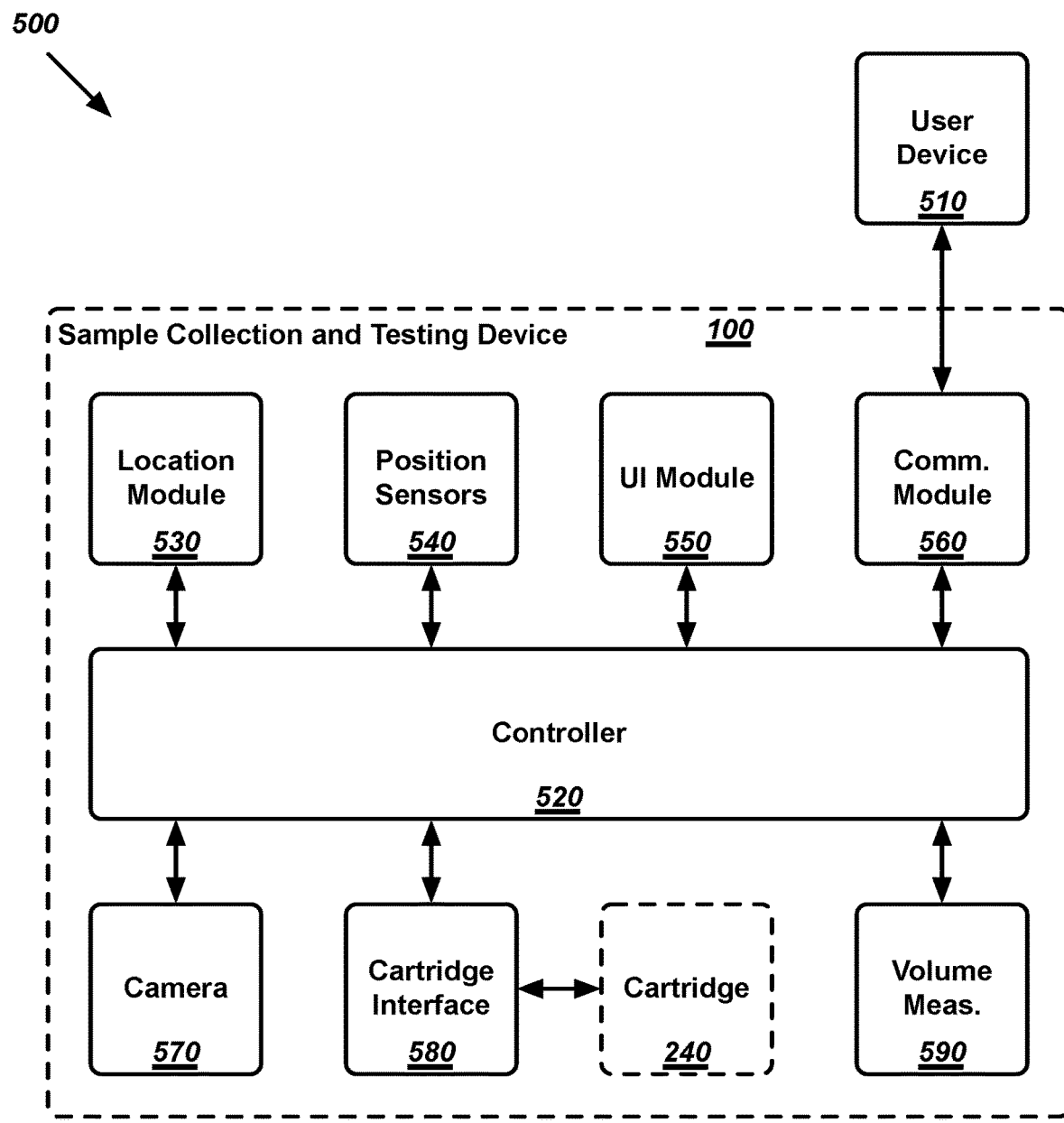
FIG. 5 illustrates a schematic block diagram of a system including the automated sample collection and testing device of FIG. 1.

FIG. 5 illustrates a schematic block diagram of a system 500 including the automated SCTD 100, sample processing module 110, and a user device 510. As shown, the SCTD 100 may include a controller 520, location module 530, position sensors 540, UI module 550, communication module 560, camera 570 (and/or other appropriate sensors), cartridge interface 580, and volume measurement module 590.

The sample processing module 110 may be similar to that described above in reference to FIG. 2, FIG. 3, and FIG. 4. The module 110 may include a removable test cartridge. The cartridge, or portions thereof, may be disposable (i.e., intended for a single use). several exemplary modules 110 will be described in more detail in reference to FIG. 6-FIG. 8 below.

The user device 510 may be an electronic computing device, such as a smartphone, tablet, personal computer, medical device, etc. The user device may provide various system features, such as UI output elements (e.g., display of test results, status, etc.), UI input elements (e.g., menus, buttons, etc.), and/or connectivity (e.g., via a cellular or wireless network connection). In some embodiments, the user device may be able to at least partly control the operations of the SCTD 100. For instance, a user such as a medical professional may initiate a test sequence by pressing a button on a tablet after a subject has been properly positioned with respect to the SCTD 100 (and sample collection element thereof).

The controller 520 may be an electronic device that is able to execute instructions and/or process data. The controller may be able to at least partly direct the operations of the other components. The controller may be associated with a local memory (not shown) that is able to store instructions and/or data.

The location module 530 may include various electronic components that are able to determine a geographic location. Such components may include, for instance, global positioning system (GPS) components.

The position sensors 540 may include various sensors, accelerometers, gyroscopes, etc. that may be able to determine a relative position of the SCTD. Such components may be used to ensure, for instance, that the SCTD is on a level surface. Some embodiments may include components that are able to automatically adjust device position based on such sensor measurements.

The UI module 550 may include various buttons, touchscreens, displays, indicators, keypads, microphones, speakers, etc. that may allow interaction with a user and/or subject.

The communication module 560 may be able to communicate across one or more wired or wireless pathways. Such pathways may include, for instance, universal serial bus (USB), Bluetooth, Wi-Fi, Ethernet, the Internet, etc.

The camera 570 (and/or other appropriate sensors) may be a color, HD camera that is able to capture video and/or still photographs. Such captured data may be able to be automatically analyzed by the controller and/or other components. Other embodiments may include different types of sensors such as environmental sensors (e.g., temperature, humidity, elevation, barometric pressure, etc.), subject attribute sensors (e.g., temperature, pulse rate, blood pressure, etc.), etc. In some embodiments, the sensors may be provided by one or more external components, with a resource such as controller 520, via communication module 560, may retrieve the data from such external components.

The cartridge interface 580 may include various components appropriate for interaction with a removable test sample processing module 110. For instance, some embodiments may utilize the camera 570 to scan a graphic code on the test cartridge. As another example, some embodiments may include components that are able to read radio frequency identification (RFID) tags or other similar tags. As still another example, some embodiments may be able to retrieve information through a digital or analog connection to the sample processing module 110. As yet another example, some embodiments may utilize near-field communication (NFC).

In some embodiments, the cartridge interface 580 and sample processing module 110 may have shared elements, complementary elements, and/or otherwise associated components that may together provide various functions described in reference to the cartridge.

The volume measurement module 590 may be able to interact with the cartridge interface 580 (and/or other appropriate elements) in order to determine volume measurements associated with sample fluids. As described in more detail in reference to FIG. 11 below, the volume measurement module 590 may include and/or interact with various other elements (e.g., optical sources and sensors) that are able to determine a volume of a fluid sample.

Figure 6:
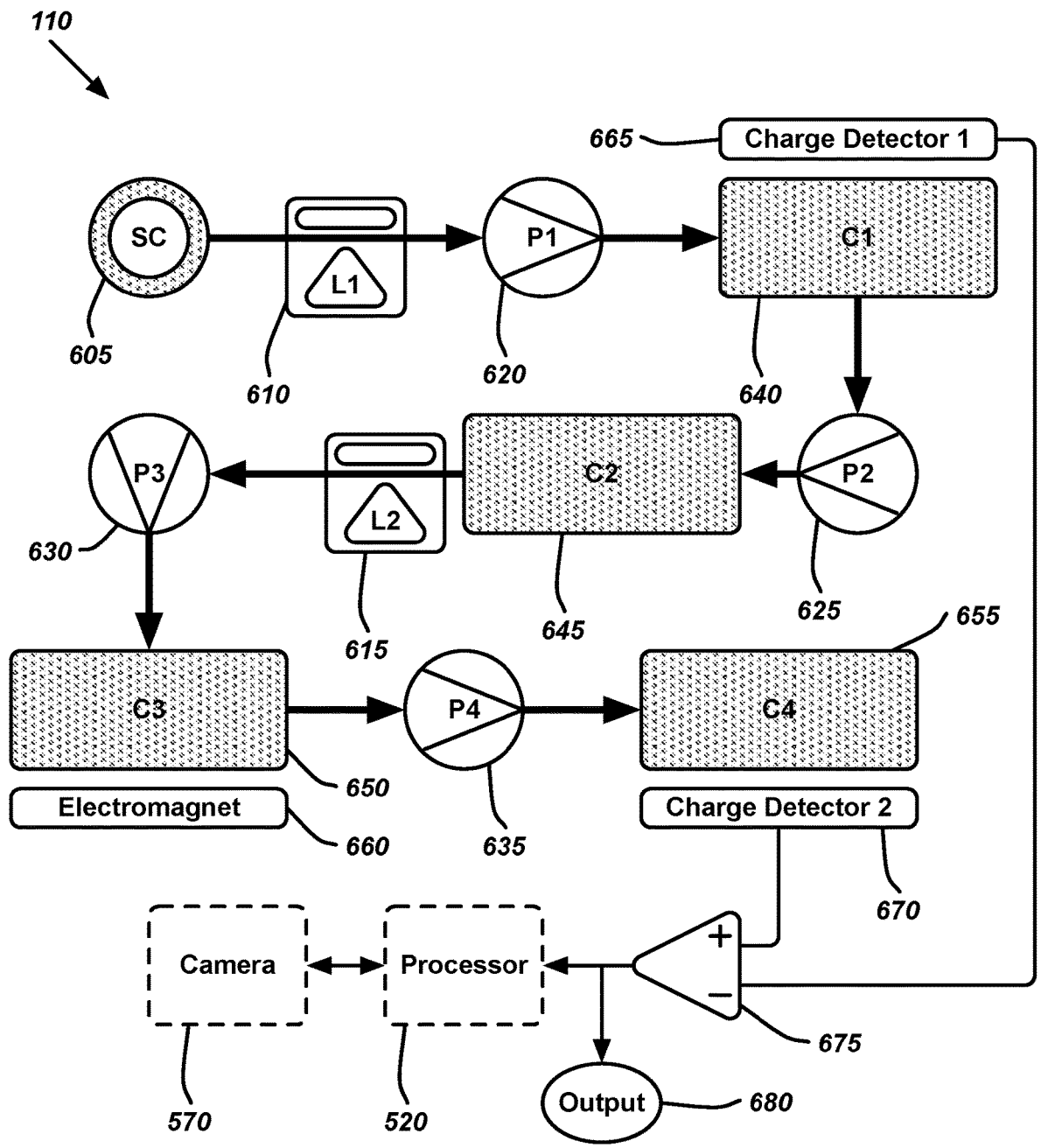
FIG. 6 illustrates a schematic block diagram of an exemplary embodiment of the sample processing module included in the sample collection and testing device of FIG. 1.

FIG. 6 illustrates a schematic block diagram of an exemplary embodiment of the sample processing module 110. As shown, this example module may include a sample collection element 605, multiple optical measurement elements 610-615 (e.g., lasers, LED light sources, etc.), multiple bi-directional pumps 620-635, multiple cavities 640-655, an electromagnet 660, a pair of charge detectors 665-670, a differential output generator 675, a camera 570, and a processor 520. This example sample processing module 110 is associated with tests to diagnose cancer. Different embodiments may include different components and/or arrangements of components when associated with other tests (e.g., blood sugar levels).

The sample processing module 110, or portions thereof, may be self-contained such that each subject may use a new disposable cartridge. As such, the fluid collected by the cartridge may be completely contained within the cartridge and not exposed to the SCTD device 100. The cartridge elements may be made out of (and/or enclosed or embedded in) appropriate materials that are impervious to the various fluids collected or used within the sample processing module 110. Such materials may include plastics, silicone, composites, etc. In this example, the fluid flow pathway is indicated by thicker arrows, while communicatively coupled elements are indicated by thinner lines or arrows. In addition, the components that contact the sample are indicated by a fill pattern.

In some embodiments, the disposable cartridge portion may include the sample collection element 605, the cavities 640-655, and the tubing between them. Such a configuration allows the more expensive components (such as pumps, optical detectors, etc.) to be reused across multiple cartridges.

The sample collection element 605 may be similar to that described above in reference to FIG. 3 or FIG. 4. At minimum, the sample collection element may include a cavity that is able to receive an amount of fluid for testing. In some embodiments, the cavity may include a fluid sensing chip. Some elements of the sample collection element (e.g., the pump or pinch valve) may be shared with other elements of the sample processing module 110. For instance, pump 620 may act as pump 315 in some embodiments.

Each of the pumps 620-635 may be a peristaltic or other appropriate pump that is able to move fluid along a flow pathway (e.g., the areas indicated by the fill and thick arrows). Such a pathway may include various flexible tubes or cavities within a fluid retaining housing (e.g., a silicone housing). In some embodiments, a peristaltic pump may move fluid along the pathway. Such pumps may also act as valves, such that when the pumps are not operating, fluid flow between cavities (and/or other elements along the pathway) is prevented.

Each of the multiple optical measurement elements 610-615 (or other optical sensors, or other types of volume measurement sensors) may include a source and a collector or absorber. The optical measurement elements may be placed along the fluid flow pathway such that fluid flow is able to be detected. The optical sensors 610-615 of some embodiments may be utilized without contacting the fluid sample. In this way, the cost of cartridges may be reduced as the sensors are able to be used across numerous samples.

Each of the multiple cavities 640-655 may be able to store an appropriate amount of fluid. The cavities may be connected to the flow pathway at multiple locations (e.g., an input and an output).

The electromagnet 660 may include various appropriate components that are able to provide a controllable magnet.

The pair of detectors 665-670 (e.g., charge detectors, impedance detectors, conductivity detectors, etc.) may include various elements such as metal plates, capacitors, circuitry, etc. that may be able to detect and/or store charge, and/or otherwise sense qualities of the cavity contents.

The differential output generator 675 may be able to receive the outputs of the charge detectors 665-670 and generate a signal 680 that is proportional to a difference in sensed charge at each charge detector 665-670. The differential output 680 may be provided as an analog and/or digital signal. The output may be provided to a processor 520, as shown, and/or may be provided directly to an external resource such as the SCTD 100.

The camera 570 may be able to capture images and/or video associated with the sample processing module 110. The camera 570 may be placed above the sample processing module 110 such that activity inside the cartridge may be monitored. The camera 570 may be able to track fluid movement (and/or other appropriate factors) in real time such that adjustments may be made or problems identified. In some embodiments, the camera may be associated with the SCTD 100 rather than included in the disposable cartridge in order to reduce cartridge cost. The camera 570 may be high definition, 4K, and/or other appropriate formats of any resolution. Higher resolutions may provide more image processing capability if needed.

The processor 520 may be an electronic device capable of executing instructions and/or processing data. The processor may be able to at least partly control the operations of the various other components (although various connections have been omitted for clarity). For instance, the processor may direct the operations of the electromagnet 660. As another example, the processor 520 may receive and analyze data from the optical measurement elements 610-615. The processor 520 may have an associated memory (not shown).

Although this example includes charge detectors 665-670 and an electromagnet 660 that are used for charge differential detection, other embodiments may utilize other sensing components. For instance, some embodiments may include active electronic components such as sensors that directly contact the fluid sample. In such cases, a signal from such a component may be received and analyzed by the processor 520 of some embodiments (and/or other appropriate components such as a sensor interface). Some embodiments may utilize inductive power and wireless data exchange such that no physical connections to the chip are needed.

Figure 7:
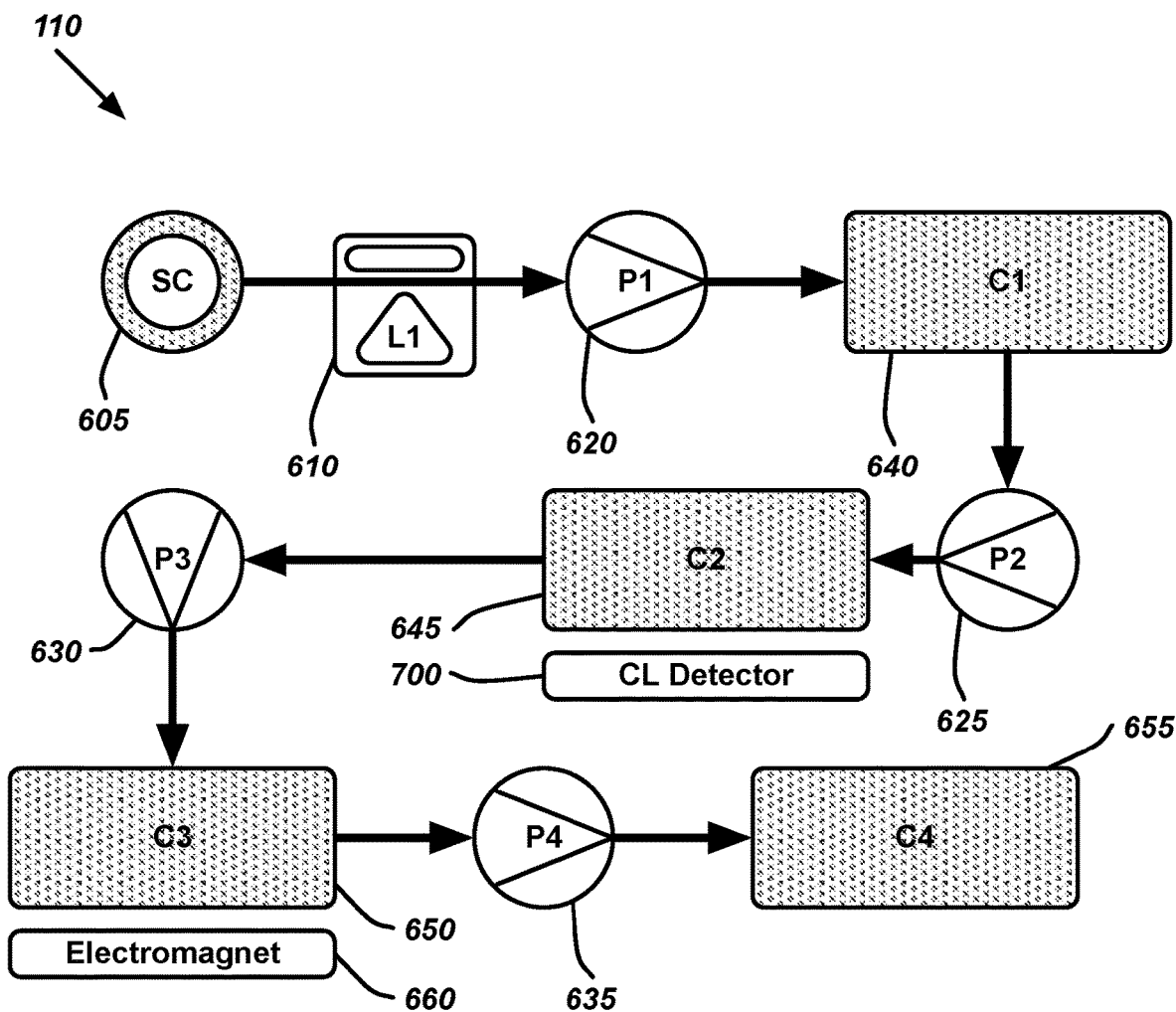
FIG. 7 illustrates a schematic block diagram of a second exemplary embodiment of the sample processing module included in the sample collection and testing device of FIG. 1.

FIG. 7 illustrates a schematic block diagram of a second exemplary embodiment of the sample processing module 110. As shown, the module may include many of the same components as the module of FIG. 6. In the example of FIG. 7, the second cavity 645 may be associated with a chemiluminescence (CL) detector 700. Such a detector may be able to sense photons emitted from CL particles. In addition, unlike the example of FIG. 6, the charge detectors 665-670 and second measurement element 615 are not needed. The output of the CL detector 700 may be converted to a discrete value and supplied to a processor (and/or other appropriate elements), as in FIG. 6. Similar such processing elements may at least partly direct the operations of the components of the sample processing module 110.

As above, in this example, the fluid flow pathway is indicated by thicker arrows, while communication pathways among elements are omitted for clarity. In addition, the components that contact the sample are indicated by a fill pattern.

Figure 8:
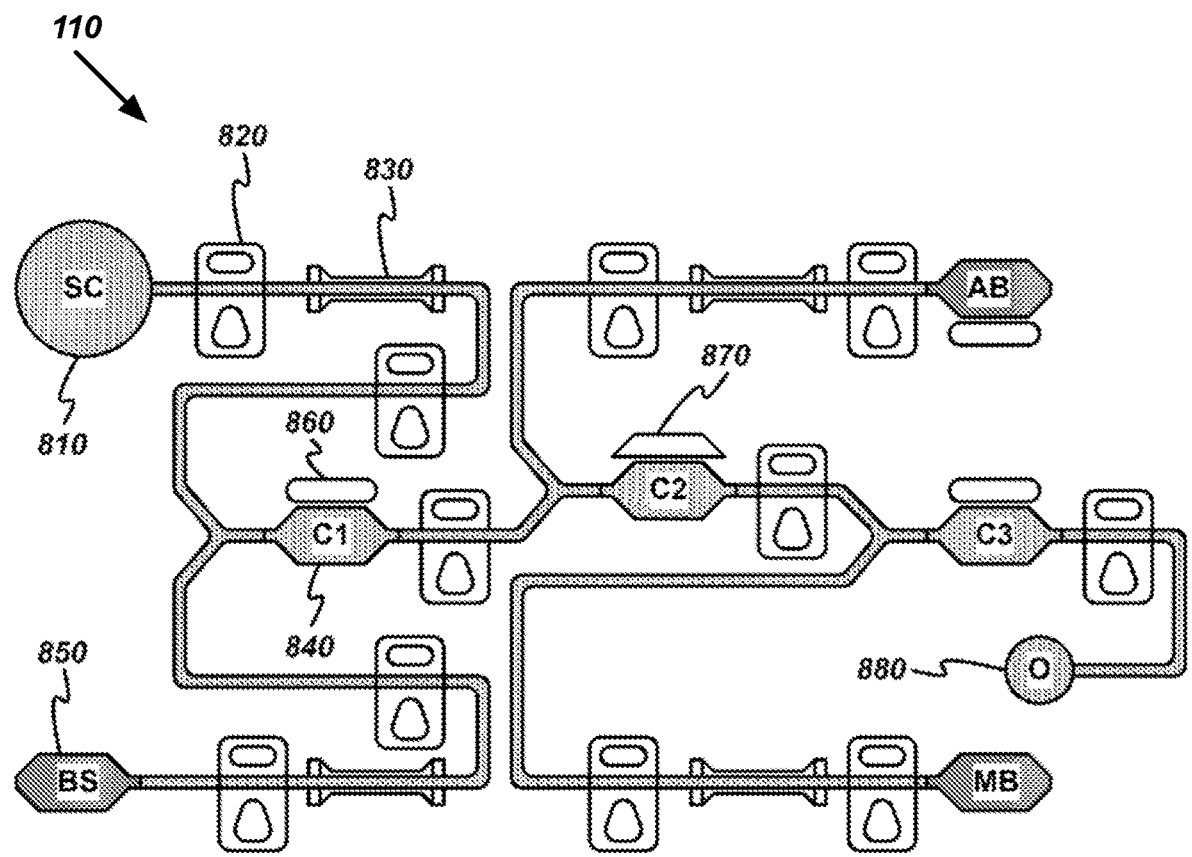
FIG. 8 illustrates a schematic block diagram of a third exemplary embodiment of the sample processing module included in the sample collection and testing device of FIG. 1.

FIG. 8 illustrates a schematic block diagram of a third exemplary embodiment of the sample processing module 110. As shown, the module may include a sample collection element 810, multiple optical measurement elements 820, multiple bi-directional pumps 830, multiple empty cavities 840, multiple pre-filled cavities 850, multiple detectors 860, at least one electromagnet 870, and a fluid output port 880.

The sample collection element 810 may be similar to element 605 described above. Each optical measurement element 820 may be similar to measurement elements 610-615 described above. In this example, measurement elements 820 are located throughout the module 110. Such an arrangement may be useful while developing or testing a new module or cartridge. Some embodiments may omit some such elements in order to reduce cost. Each bi-directional pump 830 may be similar to pumps 620-635 described above. The electromagnet 870 may be similar to electromagnet 660 described above.

Each empty cavity 840 may be similar to cavities 640-655 described above. Each pre-filled cavity 850 may be similar to cavities 640-655 described above and may include various solutions, materials, etc. that may be used during performance of the associated test. In this example, a first pre-filled cavity 850 includes a buffer solution (BS), a second pre-filled cavity includes antibodies (AB) that may be electrically charged or tagged with particles that are attached to the AB molecules (e.g., gold particles of various sizes), and a third pre-filled cavity includes certain agents or proteins attached to magnetic beads (MB). The size and/or other characteristics of each cavity 840-850 may depend on various relevant factors (e.g., desired volume, properties of stored solutions or materials, etc.).

Each detector 860 may be capable of detecting various attributes of the contents of an associated chamber 840 or 850. Such attributes may include, for instance, charge, impedance or conductance, pH level, color or other visual attributes, and/or any other measurable attribute of the fluid.

The fluid output port 880 may allow fluid to be provided to an external element via the cartridge of some embodiments. For instance, the cartridge may be removed and fluid collected from the cartridge for further analysis.

In this example, elements having a fill pattern are associated with a disposable portion of the module 110, while elements having no fill pattern are associated with the reusable portion of the module.

The outputs of the detectors 860 may be converted to a discrete value and supplied to a processor (and/or other appropriate elements), as in FIG. 6. Likewise, such elements may be able to at least partly direct the operations of the various pumps 830, measurement elements 820, sample collection element 810, detectors 860, electromagnet 870, etc.

Several sample operations of the sample processing modules of FIG. 6-FIG. 8 will be described in more detail in references to processes 2800-3000 below. In these examples, the sample collection modules may include similar (or the same) reusable components. For instance, although the different examples may include different numbers of cavities within the disposable cartridge, each example uses the same number of pumps (where the layout of each different cartridge may be arranged to utilize those pumps). Different embodiments may utilize different numbers of pumps (or other such reusable components) as well. In addition, the reusable components may include elements (e.g., the CL detector 700) that are only used by some embodiments of the disposable cartridge.

Figure 9:
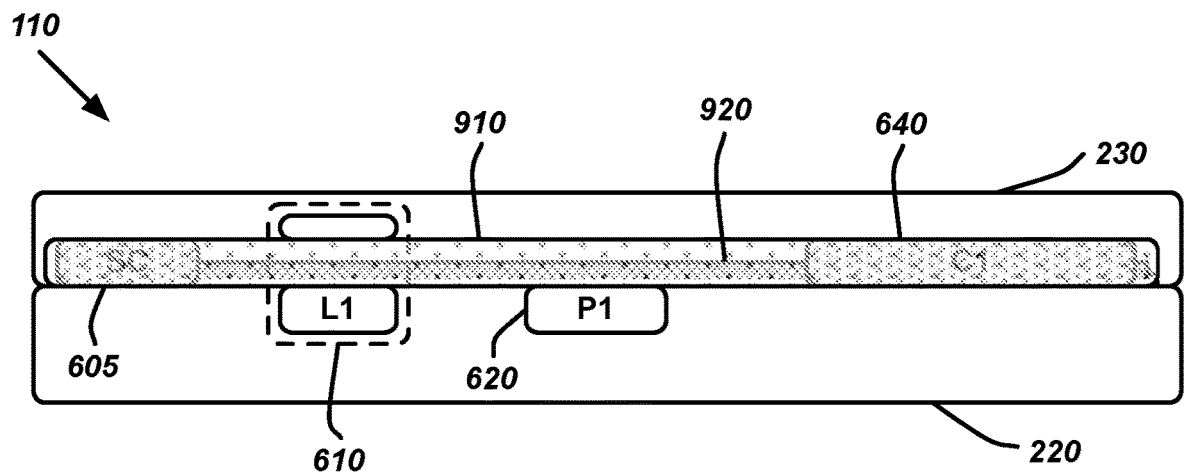
FIG. 9 illustrates a partial side view of a sample processing module according to an exemplary embodiment.

FIG. 9 illustrates a partial side view of a sample processing module 110 including a disposable cartridge (or "insert") 910 according to an exemplary embodiment. This example includes a sub-set of the components described above in reference to FIG. 6.

As shown, the sample processing module 110 of FIG. 9 may include the removable insert 910 including a fluid flow pathway 920, a top portion 230, and a bottom portion 220. In some embodiments, the top and bottom 220-230 may be reusable and may include a solid housing made of, for example, plastic or metal. The top and bottom may be coupled together (and/or to the device housing) in various appropriate ways, including hinges, latches, tabs and sockets, nuts and bolts, compression fit, magnets, etc.

The removable insert 910 may be made of (or housed within) a flexible material such as silicone such that inserts may be inserted into and/or removed from the cartridge housing. The insert may include various ridges, notches, slots, cavities, receptacles, etc. that may engage complementary elements of the cartridge housing.

Figure 10:
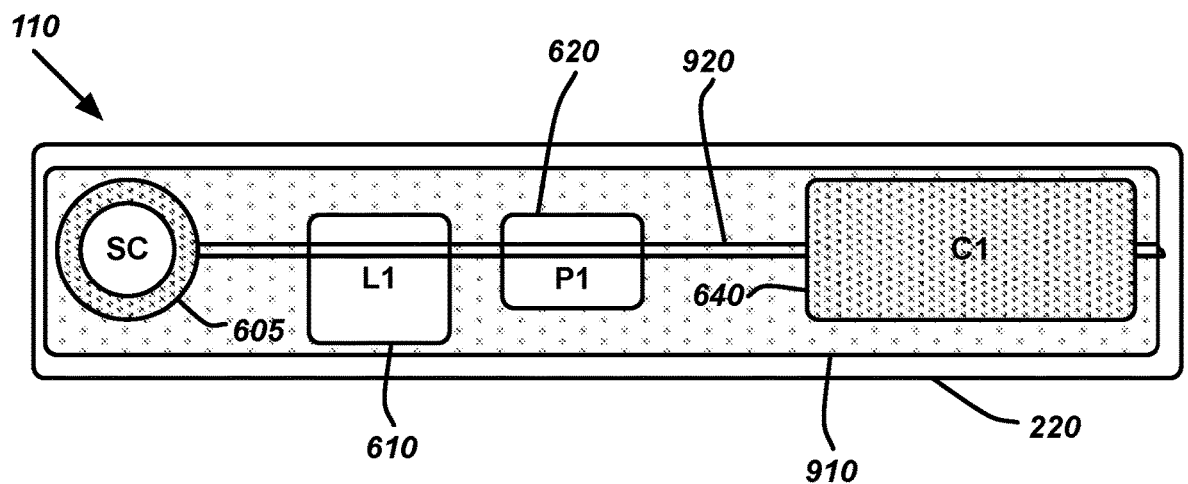
FIG. 10 illustrates a partial top view of a sample processing module according to an exemplary embodiment.

FIG. 10 illustrates a partial top view of a disposable insert 910 and sample processing module 110 according to an exemplary embodiment. This example includes the same sub-set of components shown in FIG. 9. In the view of FIG. 10, the top portion 230 has been omitted for clarity.

As shown, the disposable insert 910 may house at least a portion of the sample collection element 605, cavity 640, and cylindrical tubes or other appropriate connectors. The pump 620 may engage a portion of the flow pathway 920 without contacting the sample. For instance, the pump 620 may be a peristaltic pump that includes a rotating member with a number of protruding ridges aligned with a portion of the insert tubing 920. The optical measurement element 610 may be associated with a transparent or semitransparent portion of the insert 910 and associated tubing 920. The optical measurement element 910 may be oriented vertically, as in FIG. 9, horizontally, as in FIG. 10, and/or other may utilize other appropriate orientations.

Figure 11:
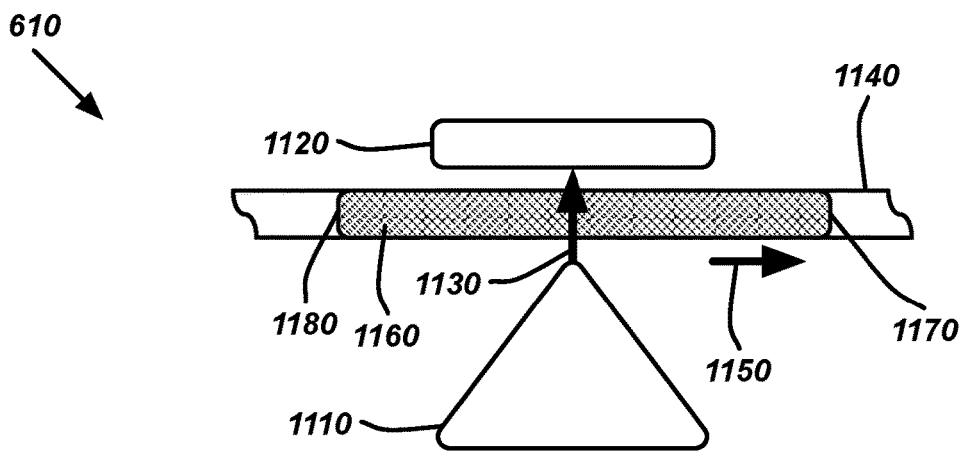
FIG. 11 illustrates a side elevation view of an optical measurement element according to an exemplary embodiment.

FIG. 11 illustrates a side elevation view of an optical measurement element 610 or 615 according to an exemplary embodiment. As shown, the optical measurement element may include an emitter 1110, an absorber 1120, a beam 1130, a fluid path 1140, forward flow direction 1150, fluid sample 1160, starting edge (or "leading" edge) 1170, and ending edge (or "trailing" edge) 1180. The operation of the components of the optical measurement element 610 may be at least partly controlled by a resource such as controller 520.

At least some portions of the pathway 1140, including any portions associated with a beam 1130, may be translucent or semi-translucent such that more energy is able to be measured at the absorber 1120. When an opaque or semi-opaque fluid (such as blood) passes through that portion of the pathway 1140, the amount of energy measured at the absorber 1120 may decrease versus the energy absorbed when there is a lack of fluid in the pathway. An appropriate threshold may be set such that fluid flow at the particular location may be detected. The optical sensors 610 may be placed before and/or after an associated pump (and/or other appropriate components).

In this example, the emitter 1110 is on one side of the fluid path 1140 while the absorber 1120 is on an opposite side. The path 1140 may be embedded into an insert, such as path 920 in insert 910. In some embodiments, the emitter 1110 and absorber 1120 may both be on one side of the fluid path 1140 (e.g., both may be housed within the bottom portion 220 of the sample processing module 110), while a reflective element is located on the opposite side. Such embodiments may reduce the cost of components included in the disposable cartridge 240. In some embodiments, the absorber(s) 1120 may be located within the top portion 230 of the sample processing module. In other embodiments, the emitter(s) 1110 may be located within the top portion 230 of the sample processing module while all other components are included within the bottom portion 220.

Some embodiments may include other types of optical sensors. For instance, some embodiments may utilize an LED light source and a photodetector. The photodetector may have an analog output that is fed to an analog to digital converter for processing. Such a scheme may be used to measure volume by determining a length of fluid (e.g., several microns), and calculating a volume based on a diameter of a tube or other connecting element. The output of the photodetector may be analyzed by a processor to determine the beginning and end of a volume of fluid. Such an approach may allow very accurate measurement of volumes.

Some embodiments may capture, store, and/or analyze a signal that is generated based on the output of the photodetector or other absorbing element. Such an approach may allow the device to handle issues such as gaps in the fluid sample along the pathway. The signal may be stored (along with other test parameters) for future analysis.

In some embodiments, the detector 610 may measure a volume of fluid by incrementing a counter while the detector 610 senses an opaque fluid, where the count may be able to be translated to a fluid volume based on the sizing of the tubing 1140 and count value. As each count increment may be associated with a very small amount of fluid, counting a large number of increments (e.g., five hundred, one thousand, etc.) may provide an accurate measure of volume.

In some embodiments, multiple detectors may be placed serially along a path in order to measure flow rate or viscosity. Of course, as in the example of FIG. 8, such detectors may be utilized for other purposes as well. Such flow rate detection may be used to measure performance of blood thinners. For instance, a leading edge of a sample may be detected at a first detector at a first time. The leading edge of the sample may be detected at a second detector at a second time. The difference between the first time and the second time may be used to calculate a "thickness" or viscosity parameter that may be used to evaluate the performance of the blood thinner.

Figure 12:
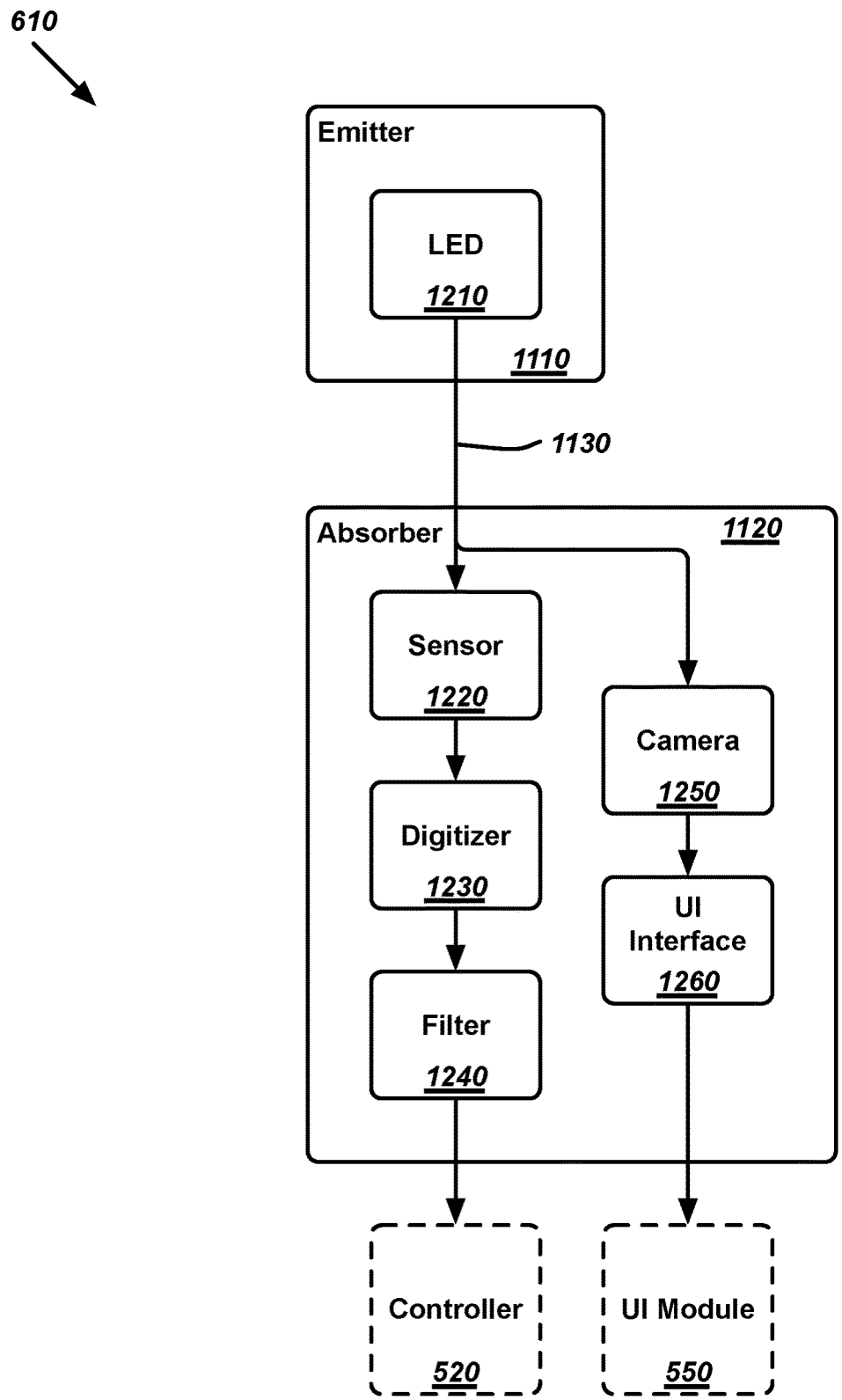
FIG. 12 illustrates a schematic block diagram of an optical measurement element according to an exemplary embodiment.

FIG. 12 illustrates a schematic block diagram of an optical measurement element 610 according to an exemplary embodiment. As shown, the optical measurement element may include an emitter 1110 and an absorber 1120. The emitter 1110 may include one or more optical sources 1210. The absorber 1120 may include a sensor 1220, digitizer 1230, filter 1240, camera 1250, and UI interface 1260.

Each optical source 1210 may include an optical output element such as an LED, bulb, laser, etc. The optical source(s) may be arranged in an array in some embodiments. As described in more detail in reference to FIG. 13 below, the emitter 1110 may include various other elements associated with the source 1210. The beam (or "light pipe") 1130 formed by the source(s) 1210 may be adjustable or configurable in various ways (e.g., power to the source may be varied, different numbers of sources may be activated, etc.).

The sensor 1220 may include various components that are able to sense the beam 1130. Such an output may represent a relative amount of sensed light expressed from a minimum value to a maximum value. Performance of the sensor 1220 may be configurable in various ways. For instance, some embodiments may allow parameters such as light sensitivity, gain, output range, input range, etc. to be modified depending on various appropriate criteria (e.g., test type, sample properties, practitioner or patient preferences, etc.).

The digitizer 1230 may receive the output signal generated by sensors 1220 and convert any analog outputs into digital signals. The digitizer 1230 and sensor 1220 may be combined into a single sensor element that generates a digital output signal. In some embodiments, for example, the sensor 1220 may produce an output between zero volts (no light sensed) to five volts (maximum light sensed, i.e., fluid path is clear). Such an output may be digitized to reflect values between zero and one thousand twenty-four (or other appropriate values, depending on available number of bits and capabilities of the sensing devices). The output of the digitizer 1230 may be used to determine a color density, depth, or saturation.

The filter 1240 may perform various processing operations on the digital output signal received from the digitizer 1230 or sensor 1220. Such processing may include, for instance, averaging or other smoothing, gain or other normalizing adjustments, color filtering or other signal processing, etc. The filtered output may be provided to a resource such as controller 520.

The camera 1250 may be able to capture images or video associated with a portion of the fluid path 920 that is illuminated by beam 1130 (and/or another appropriate resource). The UI interface 1260 may receive captured data from the camera 1250 and provide the data to a resource such as UI module 550. The camera 1250 and UI interface 1260 may allow a patient or practitioner to monitor sample flow during a test.

Figure 13:
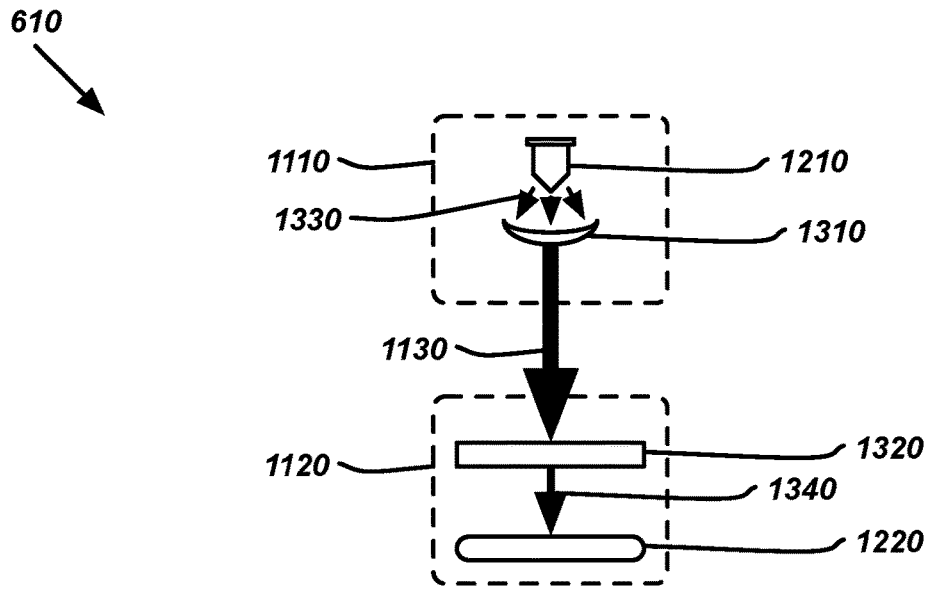
FIG. 13 illustrates a schematic block diagram of various optical processing components associated with an optical measurement element in some embodiments.

FIG. 13 illustrates a schematic block diagram of various optical processing components associated with an optical measurement element 610 in some embodiments. As shown, the optical measurement element may include a source 1210, a first optical filter 1310, and a second optical filter 1320.

In some embodiments, the source 1210 may radiate light over a range of output directions 1330. Filter 1310 may focus the beams 1330 into a single more powerful beam 1130 and/or otherwise manipulate the beams 1330 (e.g., by modifying the color of the beams). In some embodiments, the filter 1310 may be integrated into the housing of source 1210 or may be omitted. Some embodiments, as described below, may focus or filter the beam through an appropriately-sized opening in a portion of the cartridge 910.

The filter 1320 may be similar to filter 1310. Some embodiments may omit one or bother filters 1310-1320. The output beam 1340 produced by filter 1310 may be provided to sensor 1220.

Different combinations of filters and/or other elements may be utilized to maximize contrast. For instance, when measuring red blood, some embodiments will utilize a light source 1210 and/or filter 1310 that produce a blue beam 1130. Continuing the blood example, filter 1320 may be a blue filter and the sensor 1220 may be specifically configured and/or selected to have peak sensitivity to light at the blue wavelength. Thus a clear fluid path 920 would produce a very clear blue light pipe 1130 with maximum contrast versus a blood-filled portion of the fluid path 920.

Figure 14:
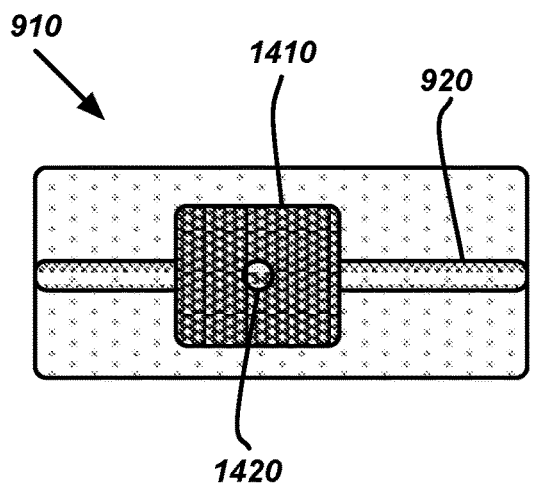
FIG. 14 illustrates a top plan view of a portion of a cartridge associated with an optical measurement element in some embodiments.
Figure 15:
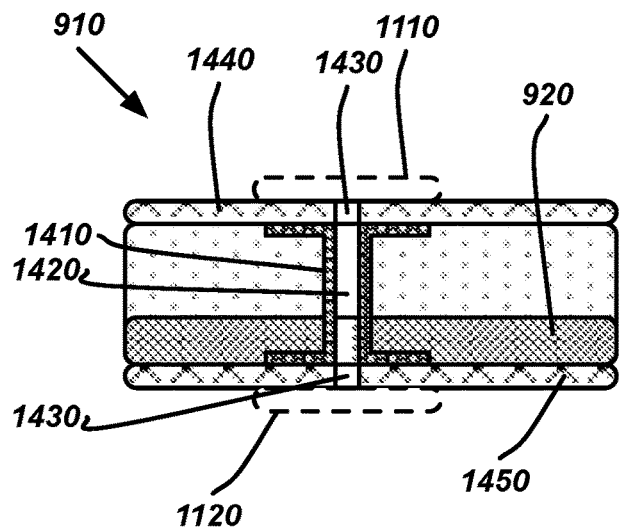
FIG. 15 illustrates a side elevation view of a portion of a cartridge associated with an optical measurement element in some embodiments.

FIG. 14 illustrates a top plan view of a portion of a cartridge 910 associated with an optical measurement element 610 in some embodiments. FIG. 15 illustrates a side elevation view of a portion of a cartridge 910 associated with an optical measurement element 610 in some embodiments.

As shown, an area associated with optical element 610 may include opaque or light-absorbing material 1410 (e.g., dark paint or other surface coating, embedded plastics, metals and/or other opaque elements, etc.). The light absorbing material may be applied to various surfaces of a cartridge 910 (and/or other appropriate elements). In some embodiments, the material 1410 may be embedded into portions of the cartridge 910.

Such material may reduce interference among multiple optical elements 610 and/or other sources of light. The cartridge 910 may include an opening (or "optical pathway") 1420 that is used to generate the light pipe 1130. In some embodiments, the opening 1420 may have a diameter of three millimeters. The size of the opening may be based at least partly on the size of the fluid pathway 920 (e.g., the opening, and thus the light pipe, may be sized to have a slightly smaller diameter than the pathway). The opening may simply be an area with no opaque material 1410. In some embodiments, the opening 1420 may include a cavity or through-hole with opaque material 1410 lining the interior wall or surface of the cylinder 1420 along the portions that do not intersect the pathway 920.

Some embodiments may include one or more light guides 1430. Such light guides may be located in a top plate 1440 and/or bottom plate 1450 of some embodiments. The top plate 1440 and bottom plate 1450 may be adjacent to the cartridge 910 during operation. The source 1110 and absorber 1120 may be attached to PC boards that sit on the opposite sides of the plates 1440-1450 from cartridge 910.

Some embodiments may include a surround (e.g., a black plastic tube) that encloses either or both light guides 1430. Some embodiments may include one or more surrounds and omit one or more of the light guides. The light guides 1430, surrounds (not shown), light absorbing material 1410, and/or other elements may together form the "light pipe" 1130 of some embodiments.

One of ordinary skill in the art will recognize that the example architectures described above are exemplary in nature and different embodiments may be implemented in different specific ways without departing from the scope of the disclosure. For instance, various components may be combined or separated. As another example, various components may be distributed differently than shown (e.g., one or more pumps may be included in a disposable cartridge in some embodiments). As still another example, different embodiments may include different numbers of pumps, optical measurement elements, cavities, etc. Furthermore, different embodiments may be sized or shaped differently depending on the application. Such differences may include different layouts of internal components, circuitry, etc.

II. Methods of Operation

Figure 16:
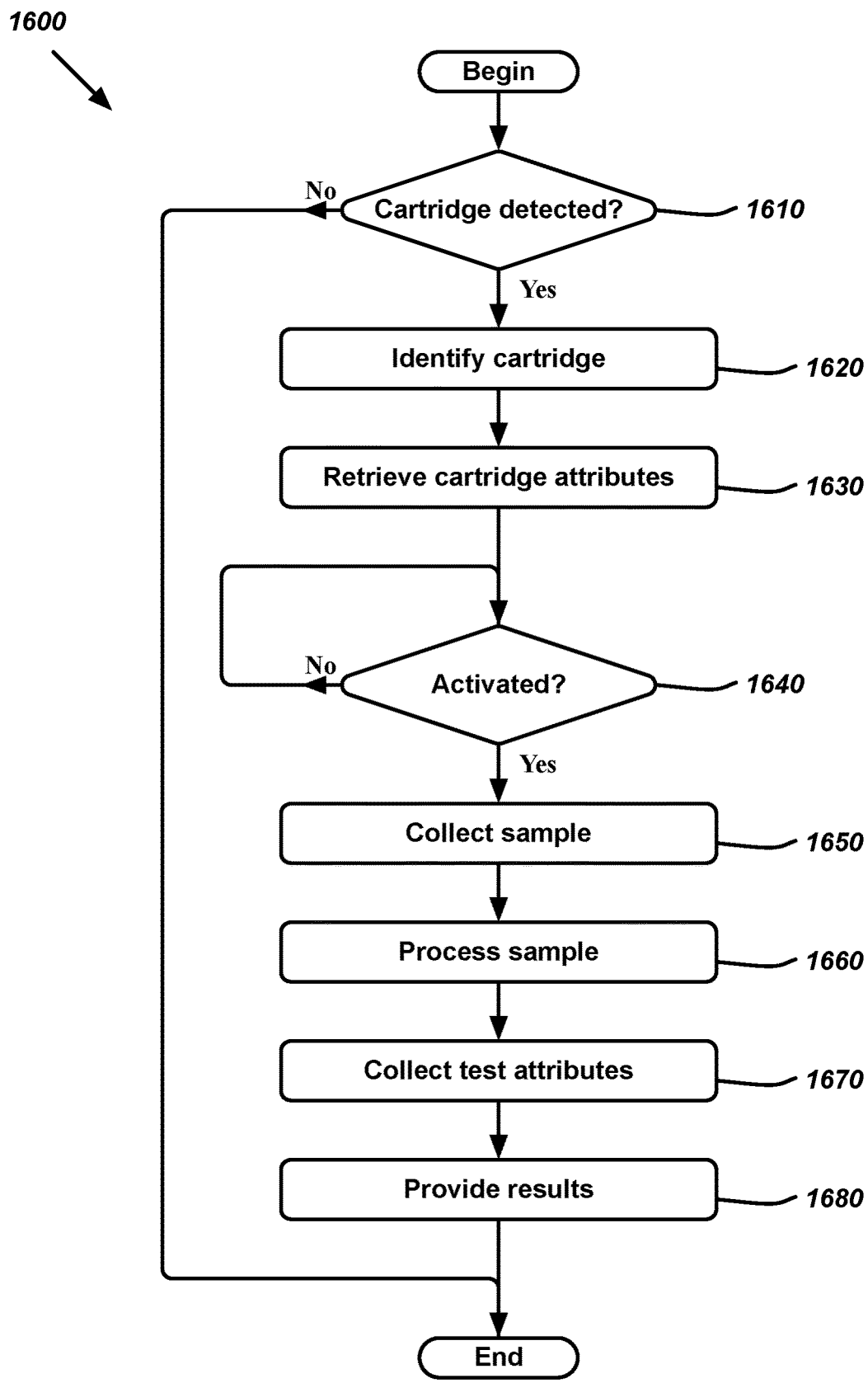
FIG. 16 illustrates a flow chart of an exemplary process that collects and tests a sample using the automated sample collection and testing device of FIG. 1.

FIG. 16 illustrates a flow chart of an exemplary process 1600 that collects and tests a sample using the automated SCTD 100. The process may begin when the device is powered on, when a sample processing module 110 is inserted, and/or other appropriate times.

As shown, the process may determine (at 1610) whether a cartridge is present. If the process determines that no cartridge is present, the process may end. If the process determines that a cartridge is present, the process may identify (at 1620) the cartridge. Such identification may include scanning of a graphic code, reading an RFID, receiving user input from an external device, etc.

Next, the process may retrieve (at 1630) cartridge attributes. Such attributes may be retrieved from the cartridge itself, from a local or remote database or look-up table, from user inputs, etc. The cartridge attributes may include, for instance, test type, fluid amounts (e.g., minimum sample volume), durations of operations (e.g., pulse counts associated with fluid measurements, reaction times, etc.), test or evaluation thresholds, etc.

The process may then determine (at 1640) whether the sample collection has been activated. Such a determination may be made based on various relevant factors, such as whether a finger (or other appropriate sample collection point) has been detected. Such a determination may be made using, for instance, the camera of some embodiments, a user input, a pressure sensor, etc.

If the process determines that no finger is detected, the process may continue trying to detect a finger until the process determines that a finger is detected. If the process determines that a finger is detected, the process may collect (at 1650) a sample. Such a sample may be collected using a needle and/or other appropriate elements as described above. Sample collection will be described in more detail in reference to process 1700 below.

Next, process 1600 may process (at 1660) the sample. Several example of such processing is described in more detail in reference to processes 2800-3000 below.

The process 1600 may then collect (at 1670) test attributes. Such attributes may include, for instance, charge difference at a pair of charge detectors, impedance or conductance of a sample (and/or processed sample), pH level, and/or any other measurable attribute of the fluid.

Next, the process may provide (at 1680) the results, and then may end. Such results may be based on comparison of the test attributes to one or more threshold values. The results may include discrete values (e.g., "pass", "fail", "inconclusive", etc.), measured values (e.g., weight or percentage of some tested parameter), and/or other appropriate result formats. The results may be provided via the SCTD 100 (e.g., using UI 120), a user device or medical device 510, and/or other appropriate ways. Some embodiments may send the results (and/or measure or intermediate values) to multiple external devices or systems using an element such as communication module 560.

Figure 17:
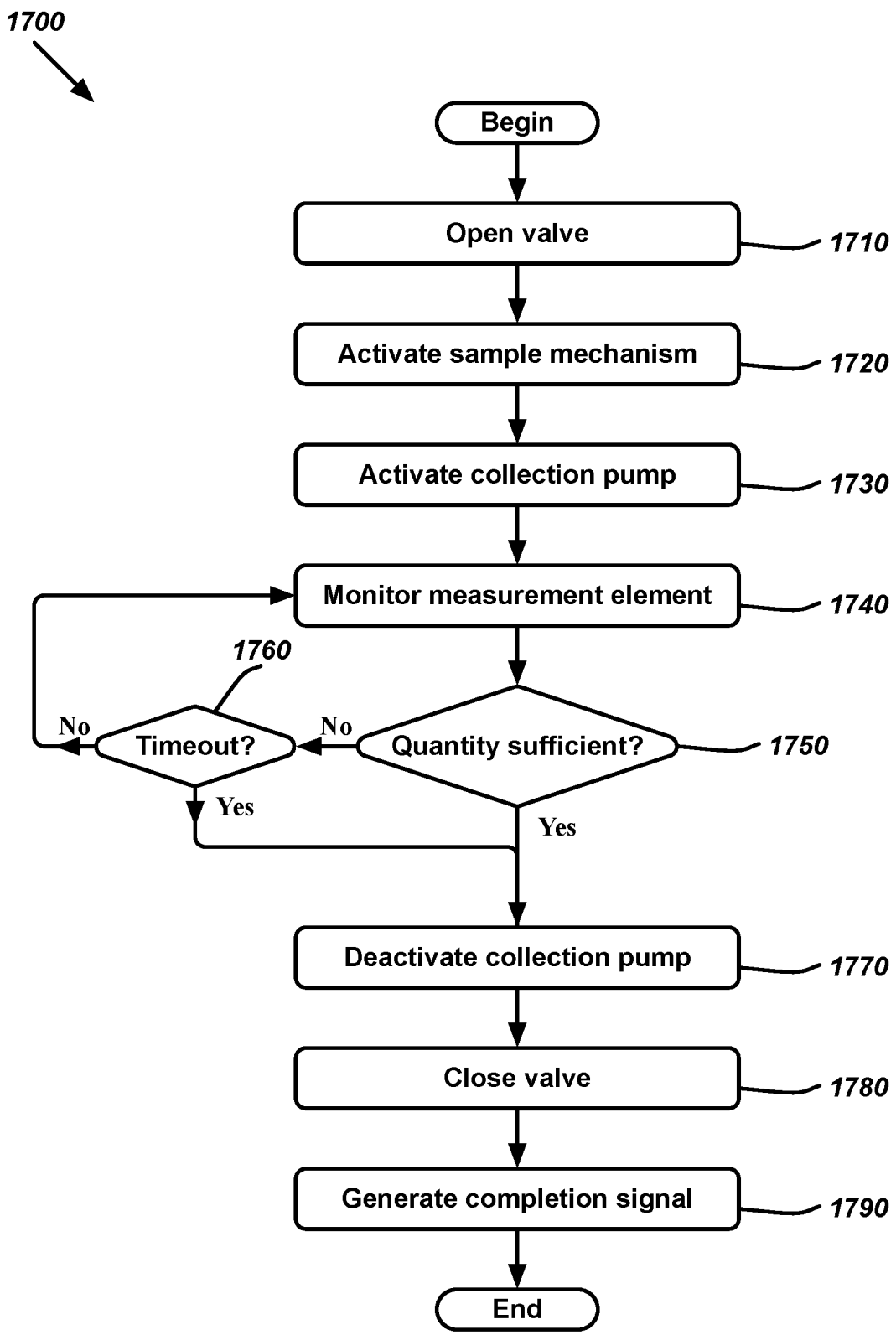
FIG. 17 illustrates a flow chart of an exemplary process that collects a sample using the automated sample collection and testing device of FIG. 1.

FIG. 17 illustrates a flow chart of an exemplary process 1700 that collects a sample using the automated SCTD 100. The process may begin when sample collection is activated as described in reference to operation 1640 above.

As shown, the process 1700 may open (at 1710) a valve such as pinch valve 320. Next, the process may activate (at 1720) a sample mechanism. Such a mechanism may include elements such as needle and spring 345, receptacle 340, and chip 325 described above. Activation of the sampling mechanism will be described in more detail in reference to process 1800 below.

Next, process 1700 may activate (at 1730) a collection pump, such as pump 315. The process may then monitor (at 1740) a measurement element such as element 610 described above. Alternatively, some embodiments may monitor collection using a camera, scale, etc. Some embodiments may simply utilize a timer rather than attributes associated with the sample itself.

The process may then determine (at 1750) whether the collected quantity is sufficient for the associated test. Such a determination may be made based on various relevant factors (e.g., counter value, weight of sample, etc.).

If the process determines the quantity is not sufficient, the process may then determine (at 1760) whether a sample timeout has been exceeded. If the process determines (at 1760) that the sample timeout has not been exceeded, the process may repeat operations 1740-1760 until the process determines (at 1750) that the quantity is sufficient or the process determines (at 1760) that the timeout has been exceeded.

If the process determines (at 1750) that the quantity is sufficient, or if the process determines (at 1760) that the sample timeout has been exceeded, the process may deactivate (at 1770) the collection pump, close (at 1780) the valve, generate (at 1790) a completion signal, and then end. The completion signal may be an internal signal that is relayed to an element such as controller 520 and may be used as a trigger to continue operations of process 1600 after collecting a sample at 1650. In some cases, no further processing may be performed after sample collection, and the completion signal may include indications at UI 120, via user device 510, and/or other appropriate signals.

In cases where the process determines (at 1760) that the timeout has been exceeded, the completion signal may indicate that the sample quantity is insufficient. Such a signal may cause the process to be re-run, or may provide a UI indication that the sample is insufficient and instruct the subject to insert another finger (or take other appropriate actions to successfully complete a sample collection, such as the insertion of a new cartridge).

Figure 18:
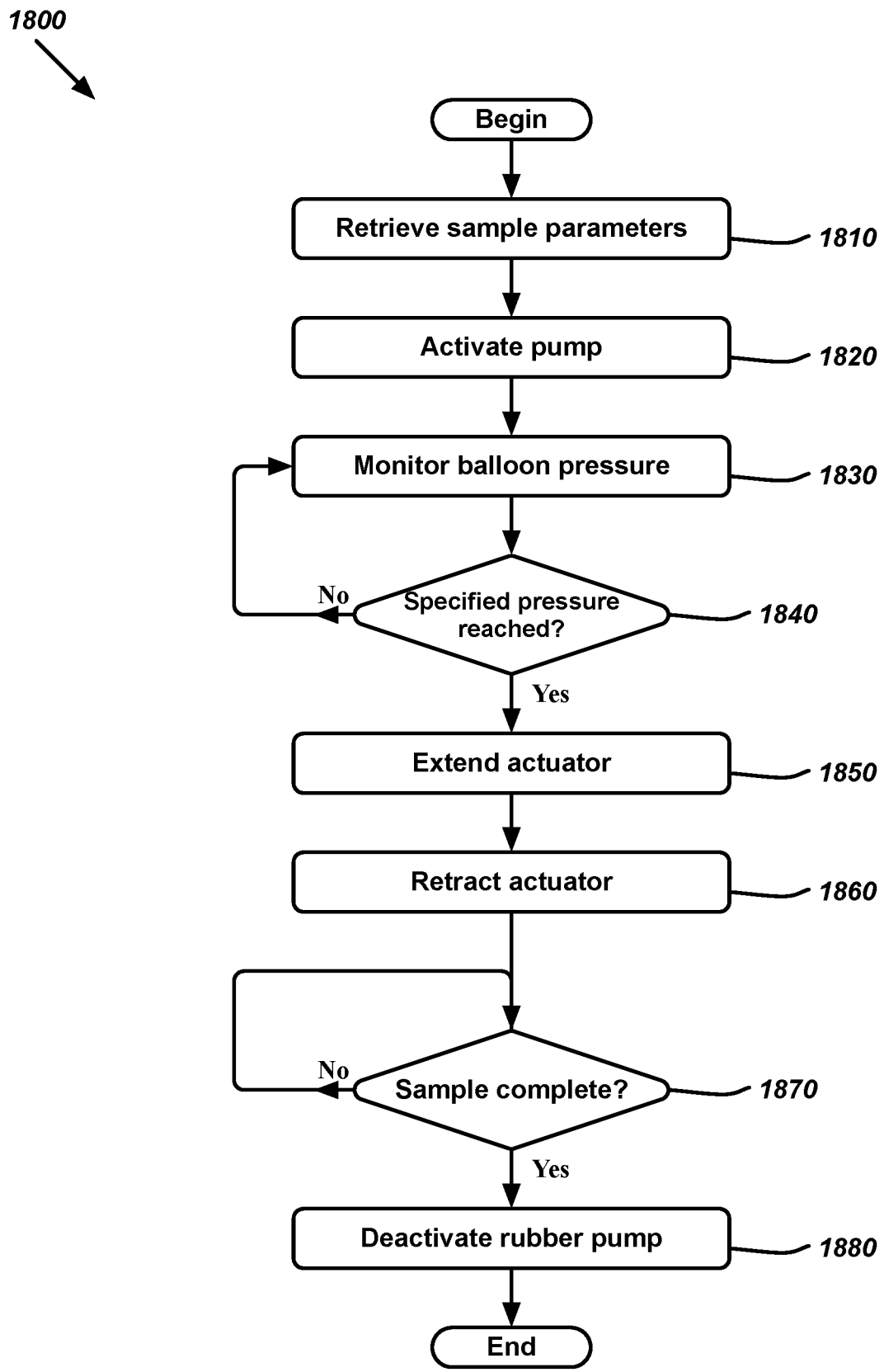
FIG. 18 illustrates a flow chart of an exemplary process that controls a sampling element of the automated sample collection and testing device of FIG. 1.

FIG. 18 illustrates a flow chart of an exemplary process 1800 that controls a sampling element of the automated SCTD 100. The process may begin when sample collection is activated as described in reference to operation 1720 above.

As shown, process 1800 may retrieve (at 1810) sample collection parameters. Such parameters may include, for instance, balloon pressure, needle extension, etc.

Next, the process may activate (at 1810) a pump such as rubber pump 305 and monitor (at 1830) pressure at a retaining element such as balloon 310. Next, the process may determine (at 1840) whether the specified pressure (or other parameter) has been reached. The process may repeat operations 1830-1840 until the process determines (at 1840) that the specified pressure has been reached.

Next, the process may extend (at 1850) an actuator such as actuator 335, such that the needle 345 or other sampling element is extended. The actuator may be extended to a specified value or may be full extended and limited by physical features of the needle, actuator housing, stops, etc.

The process may then retract (at 1860) the actuator and determine (at 1870) whether the sampling is complete. Such a determination may be made in various appropriate ways. For instance, some embodiments may wait for a completion message as described above in reference to operation 1790. As another example, some embodiments may wait for a specified amount of time. As still another example, some embodiments may wait for a user input to be received via a UI element, user device, medical device, etc.

If the process determines (at 1870) that the sample is complete, the process may deactivate (at 1880) the rubber pump (and/or other retaining elements) and then may end.

Figure 19:
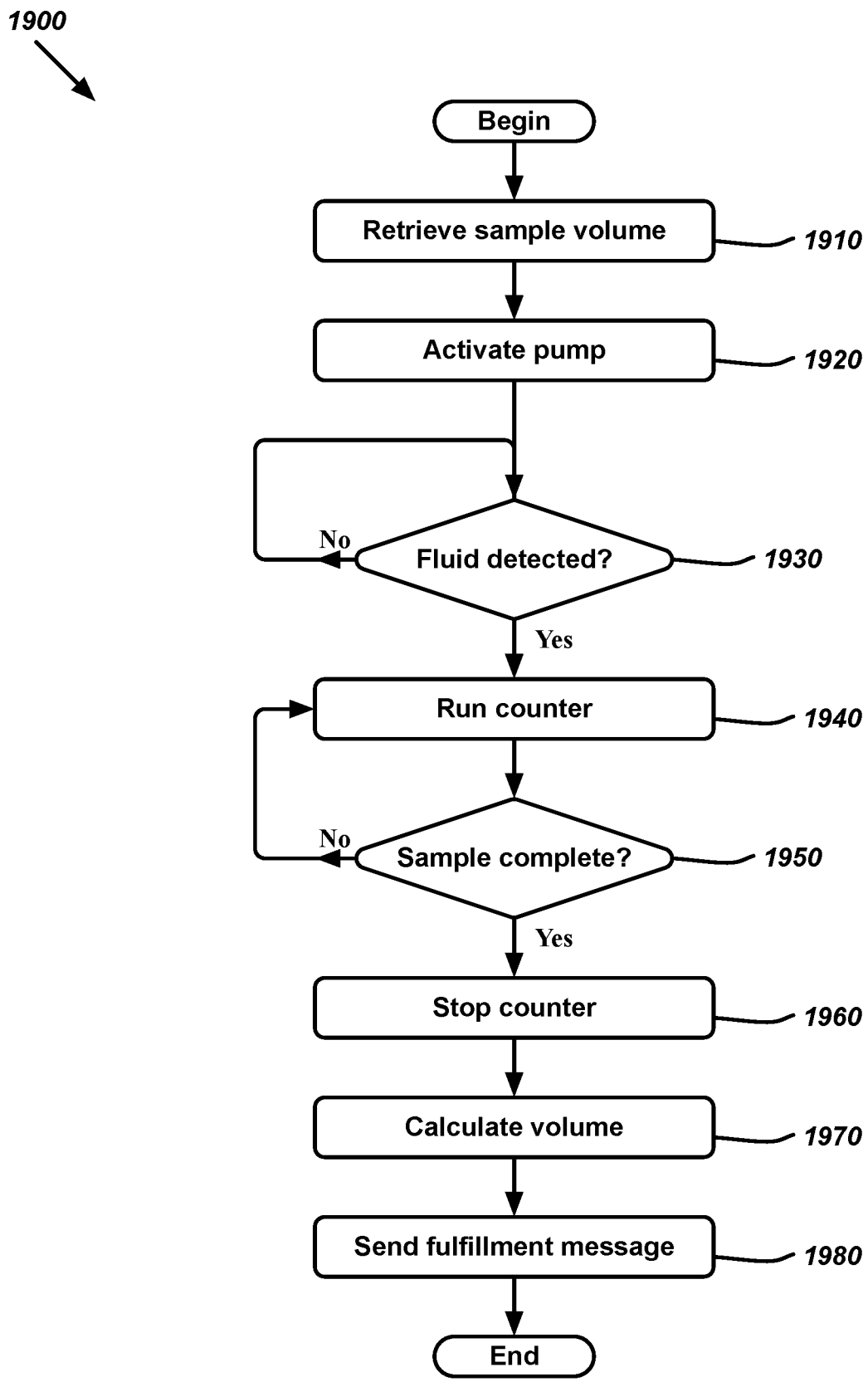
FIG. 19 illustrates a flow chart of an exemplary process that impels a small amount of fluid within the exemplary embodiments of the sample processing module included in the sample collection and testing device of FIG. 1.

FIG. 19 illustrates a flow chart of an exemplary process 1900 that impels a small amount of fluid within the exemplary embodiments of the sample processing module 110. Such a process may be executed by the SCTD 100 using an optical element such as element 610. The process may begin, for instance, when a sample is available or when a sample is being taken.

As shown, the process may retrieve (at 1910) a necessary (or minimum) sample volume. Such a volume may be retrieved from the cartridge, from a database or look-up table, received from a user, and/or other appropriate resource. The volume may be expressed as a count value or other discrete value associated with different measurement algorithms of different embodiments.

Next, the process may activate (at 1920) the appropriate pump associated with the measurement. Such a pump may be similar to pumps 315 or 620-635.

The process may then determine (at 1930) whether fluid is detected at the location of the flow pathway associated with the optical sensor 610 (and/or other appropriate elements). Such detection may be based on detection of a leading edge 1170 such as that described above. The process may iteratively or continuously attempt to detect fluid until the process determines that fluid has been detected, at which point, the process may activate (at 1940) a counter or other timing algorithm.

Such a counter may be a digital and/or analog timer. In some embodiments, the counter may specify a duration during which the fluid is detected. In other embodiments, the counter may specify a number of pump motor pulses to be applied (or a duration during which pulses are applied). The counter may be incremented at regular intervals (e.g., each clock period) when used to measure duration of time.

In some embodiments, as described above, the sensor 610 output may be converted to a digital or analog signal. In such cases, the signal may be analyzed in various appropriate ways in order to generate a "count" value (where such a value, in addition to being a literal counter or timer, may include any appropriate signal analysis). For instance, some embodiments may integrate the signal to calculate an area under a curve that may be used as the count value in order to determine a volume. As another example, the signal may be associated with various thresholds that may be used to activate or deactivate the counter (e.g., the counter value may increase when the signal is above a threshold and be held constant when the signal is below the threshold).

Next, the process may determine (at 1950) whether the sample is complete (i.e., whether the specified volume has been collected). Such a determination may be made based on whether a specified count threshold has been met or exceeded (and/or other appropriate analysis such as comparison of area to a threshold value).

If the process determines (at 1950) that the sample is not complete, the process may repeat operations 1940-1950 until the process determines (at 1950) that the sample is complete. In addition, the process may continue to monitor whether fluid is detected and may determine (at 1950) that the sample is complete when no more fluid is detected at the monitored portion of the fluid pathway. Such a determination may be made based on a gap in fluid detection having a minimum width or time duration, a sensor signal that drops below a specified threshold, etc.

If the process determines (at 1950) that the threshold volume has been collected, the process may stop (at 1960) the counter, deactivate (at 1970) the pump, send (at 1980) a completion message to other components or devices, and then may end.

Figure 20:
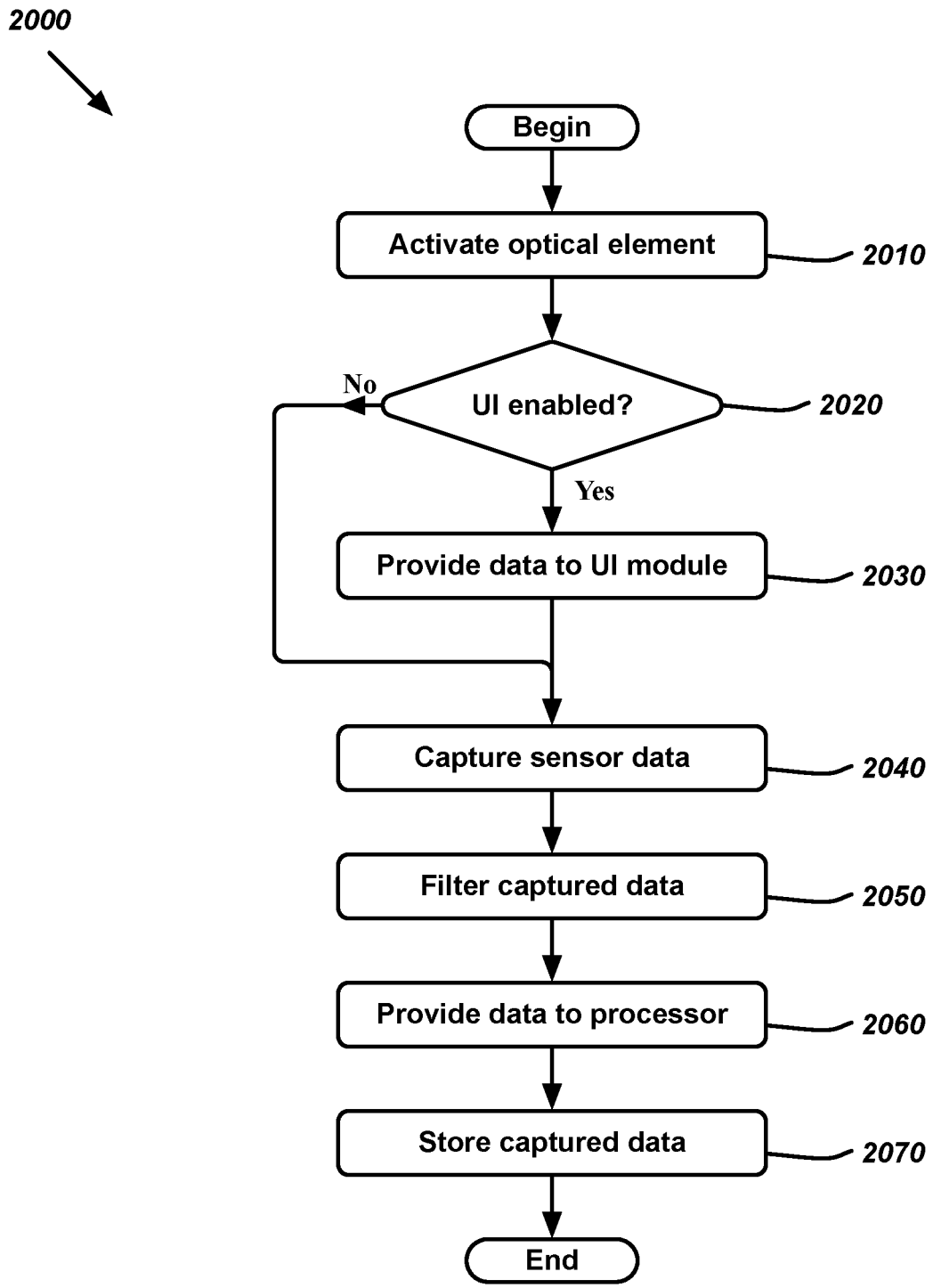
FIG. 20 illustrates a flow chart of an exemplary process that measures fluid parameters within the exemplary embodiments of the sample processing module included in the sample collection and testing device of FIG. 1.

FIG. 20 illustrates a flow chart of an exemplary process that measures fluid parameters within the exemplary embodiments of the sample processing module included in the sample collection and testing device 110. Such a process may be executed by the SCTD 100 using an optical element such as element 610. The process may begin, for instance, when the SCTD 100 is powered on.

As shown, process 2000 may activate (at 2010) an optical element of some embodiments (e.g., element 610). In addition, some embodiments may perform various calibration operations. Such operations could include, for instance, measuring absorber output with the emitter disabled, measuring absorber output with the emitter at maximum power and no cartridge inserted. As another example, some cartridges may include test fluids that may be used for calibration (e.g., a clear fluid and a red fluid) such fluids may be used only for calibration or may be associated with various substances used by the particular test cartridge (e.g., a blood thinner may be clear while an active agent may be dyed red).

Next, the process may determine (at 2020) whether the UI is enabled. Such a determination may be made based on various relevant factors (e.g., default parameters, test-specific parameters, user selections, etc.). If the UI is enabled, the process may capture data (e.g., using camera 1250) and provide (at 2030) the captured data to a UI module (e.g., by passing data from UI interface 1260 to UI module 550). Photo or video data may then be displayed by the UI 120 of some embodiments.

After determining (at 2020) that the UI is not enabled, or after providing (at 2030) data to the UI module, process 2000 may capture (at 2040) sensor data using a resource such as sensor 1220. Such data may be digitized using an element such as digitizer 1230.

Next, the process may filter (at 2050) the captured data. Such filtering may include, for instance, averaging or other smoothing, gain or other normalizing adjustments, color filtering or other signal processing, etc. The filtering may be performed by a resource such as filter 1240.

Process 2000 may then provide (at 2060) the filtered captured data to a processor or other appropriate resource (e.g., controller 520).

Finally, the process may store (at 2070) the captured data and then may end. Such data may be stored locally and/or transmitted to various other resources (e.g., user devices, servers, etc.).

In some embodiments, process 2000 may utilize feedback in order to optimize performance during a measurement operation. Such feedback may include, for instance, inputs received via UI 120 (e.g., a user may manually adjust gain or sensitivity). In some embodiments, the feedback may be generated automatically based on received data (e.g., if all measured values have fallen within a limited range, gain or sensitivity may be increased).

The SCTD, in some embodiments, may be used to determine the viscosity of a fluid. When the fluid is blood (or a derivative thereof), the viscosity may provide an indication of blood thickness (or thinness). Viscosity is the measure of the internal friction of a fluid. When a layer of fluid is made to move in relation to another layer, the greater the friction, the greater the amount of force required to cause this movement, which is called shear. The shear may be expressed as force divided by area. Viscosity may be defined by Eq (1):

$$\eta = \frac{\frac{F}{A}}{\frac{dv}{dx}} \qquad \text{EQ (1)}$$

where, $\eta$ is viscosity, F is force, A is area, and $$\frac{dv}{dx}$$

is the velocity gradient. In addition, speed is an inverse function of time as shown by EQ (2):

$$v = \frac{d}{t} \qquad \text{EQ (2)}$$

where v is speed, d is distance, and t is time. The viscosity of a fluid, therefore, has a direct relationship with the time the fluid travels between two points. For a fluid such as blood that may coagulate over time, the viscosity of the fluid may change. The SCTD may be designed such that the distance between the two points where the fluid may travel is short and the change in the fluid viscosity is negligible while the fluid travels between the two points. Some embodiments measure the viscosity of a fluid by keeping an amount of the fluid under an optical measurement element and measure the intensity of a beam of light that passes through the fluid.

Some embodiments may map the blood viscosity to the results of prothrombin time test (PT test), which is a test that measures how quickly blood clots. The results of the PT test (in seconds) measures the activity of several blood coagulation factors including prothrombin and is used to determine the tendency of blood to clot. The results of the PT is reported as the International Normalized Ratio (INR). The INR is a calculation based on results of the PT test and may be used to monitor individuals who are being treated with an anticoagulation medication such as warfarin.

The mapping may be done based on calibration performed for a particular design (or particular configuration) of the SCTD device. The indication of the blood viscosity and/or the mapping of the viscosity to the PT test results by the SCTD of the present embodiments may be used, for example and without limitations, in a doctor's office or by a patient at home to monitor the blood thickness or thinness of the patient when the patient is taking blood-thinning mediation.

Figure 21A:
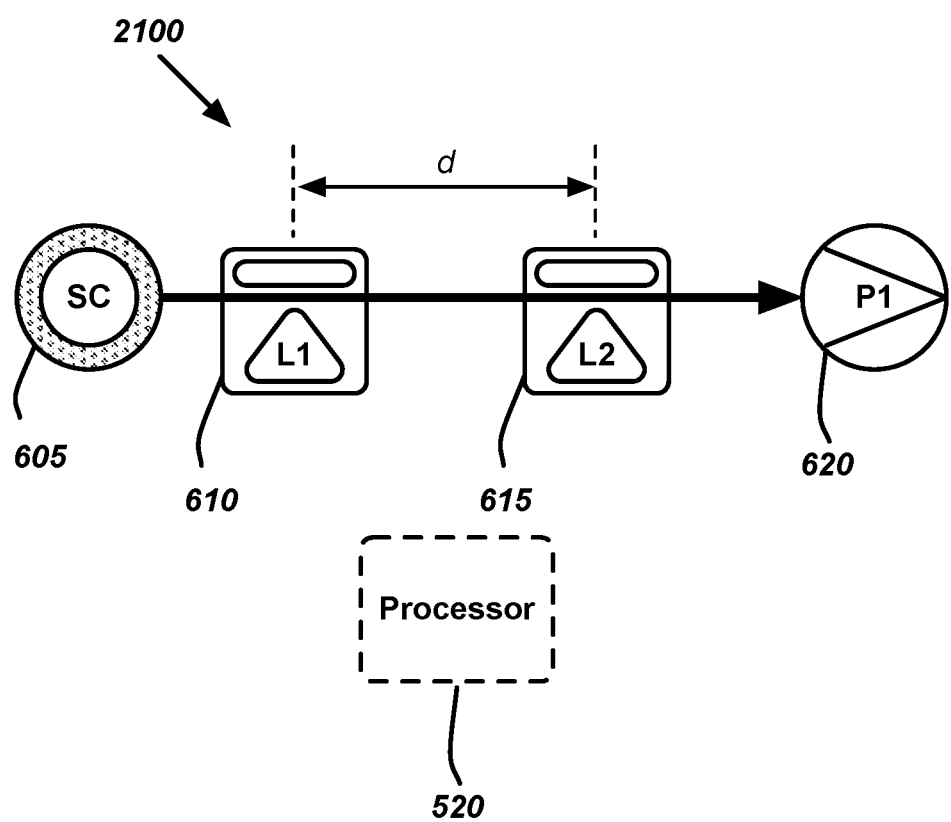
FIG. 21A illustrates a schematic block diagram of an exemplary embodiment of the sample processing module with two optical measurement elements, included in the sample collection and testing device of FIG. 1.

FIG. 21A illustrates a schematic block diagram of an exemplary embodiment of the sample processing module 2100 with two optical measurement elements, included in the sample collection and testing device of FIG. 1. The sample processing module 2100 may be used to provide an indication of the viscosity of a fluid such as blood, an indication of blood thickness or thinness, and/or an indication of blood coagulation. As shown, this example module may include a sample collection element 605, two optical measurement elements 610-615 (e.g., lasers, LED light sources, etc.), and a pump 620. The fluid flow path (shown by thick arrow) may be a capillary tube.

The sample processing module 2100, in some embodiments, may include a processor or a controller 520 (FIG. 5). In other embodiments the processor may be external to the sample processing module 2100. Different embodiments may include additional components, for example and without limitation, one or more cameras such as camera 570 (FIG. 6), one or more cavities such as cavities 640-655 (FIG. 6), additional optical measurement elements, additional pumps, etc. The sample collection element 605, the optical measurement elements 610-615, the pump 620, and the processor 520 may be similar to the corresponding components of FIGS. 6-8.

The pump 620 may be a peristaltic pump in some embodiments. The pump 620 may be unidirectional or bi-directional in different embodiments. The sample collection element 605 may include an actuator, such as the actuator 335 of FIG. 3 that may include components such as a linear solenoid, a rotary motor, etc. In some embodiments, the actuator may be controllable such that attributes such as depth or height, pressure, velocity, acceleration, torque, etc. may be able to be controlled based on various parameters (e.g., default values, user selections, measured values, etc.).

The sample processing module 2100, or portions thereof, may be self-contained such that each subject may use a new disposable cartridge 240 (FIG. 2). As such, the fluid collected by the cartridge may be completely contained within the cartridge and not exposed to the SCTD device 100 (FIG. 1). The cartridge elements may be made out of (and/or enclosed or embedded in) appropriate materials that are impervious to the various fluids collected or used within the sample processing module 2100. Such materials may include plastics, silicone, composites, etc. In this example, the fluid flow pathway is indicated by thicker arrows, while communicatively coupled elements are indicated by thinner lines or arrows. In addition, the components that contact the sample are indicated by a fill pattern.

In some embodiments, the disposable cartridge portion may include the sample collection element 605 and the tubing between them. Such a configuration allows the more expensive components (such as the pump 620, the optical measurement elements 610-615, the processor 520, etc.) to be reused across multiple cartridges.

The sample collection element 605, in some embodiments, may not include a separate pump and the pump 620 may act as the pump for the sample collection element 605.

The sample collection element 605, in some embodiments, may measure the amount of fluid in a sample taken by the SCTD device and stop taking further fluid when a predetermined amount of sample is taken (e.g., as described above with reference to operations 1740-1750 of FIG. 17).

The controller 520 may be an electronic device capable of executing instructions and/or processing data. The controller 520 may include a processor. The controller may be able to at least partly control the operations of various other components (although various connections have been omitted for clarity). For instance, the controller 520 may receive and analyze data from the optical measurement elements 610-615. The controller 520 may start and stop the pump 620. The controller 520 may open or close a valve (e.g., the pinch valve 320 of FIG. 3) in the sample collection element 605. The controller 520 may have an associated memory (not shown).

During operation, a sample fluid, such as blood, is received by the sample collection element 605 while the pump 620 may move the fluid in the fluid flow pathway in the direction of the thick arrow towards the optical measurement elements 610-615. When the leading edge of the fluid reaches the optical measurement element 610, the optical measurement element 610 may send a signal to the controller and the controller may start a timer or use an algorithm to measure elapsed time. The optical measurement element 610 may make one or more light intensity measurements of the light that goes through the fluid and may send the measurements to the controller 520. For example, the optical measurement element 610 make the measurements after a quantity of fluid is under the optical measurement element 610 (e.g., the optical measurement element 610 may be configured to make the measurements after a delay or the controller 520 may send a signal to the optical measurement element after the pump 620 moves the fluid in the fluid pathway for a few pulses (e.g., and without limitations, 1 to 10 pulses).

When the leading edge of the fluid reaches the optical measurement element 615, the optical measurement element 615 may send a signal to the controller and the controller may stop the counter. In some embodiments, the controller may operate the pump 620 for a few more pulses e.g., and without limitations, 1 to 10 pulses) to bring a quantity of fluid under the optical measurement element 615. The controller may then stop the pump and may receive one or more light intensity measurements of the light that goes through the fluid from the optical measurement element 615. As described below, the counter value (and the known distance, d, between the two optical elements 610-615), the light intensity measurements, and/or their combination may be used to determine indications of blood viscosity, blood thinness/thinness, and/or blood coagulation.

Figure 21B:
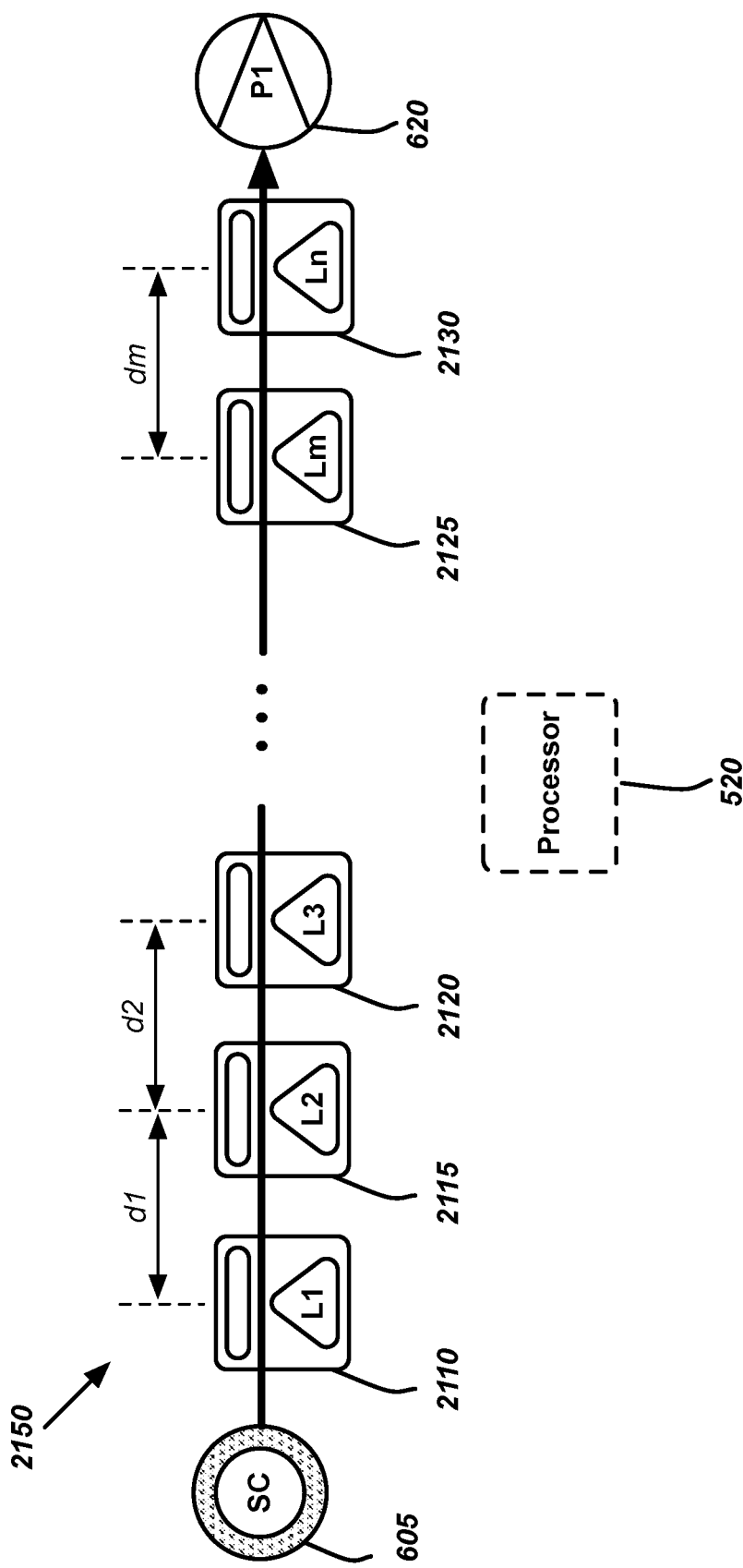
FIG. 21B illustrates a schematic block diagram of an exemplary embodiment of the sample processing module with more than two optical measurement elements, included in the sample collection and testing device of FIG. 1.

FIG. 21B illustrates a schematic block diagram of an exemplary embodiment of the sample processing module 2150 with more than two optical measurement elements, included in the sample collection and testing device of FIG. 1. As shown, the sample processing module 2150 may include a sample collection element 605, several optical measurement elements 2110-2130 (e.g., lasers, LED light sources, etc.), and a pump 620. The fluid flow path (shown by thick arrow) may be a capillary tube.

Similar to the sample processing module 2100 of FIG. 21A, the sample processing module 2150 may include other components such as a controller (or a processor), one or more cameras such as camera 570 (FIG. 6), one or more cavities such as cavities 640-655 (FIG. 6), additional optical measurement elements, additional pumps, an actuator, a disposable cartridge, etc. These components may be similar to the corresponding components of FIG. 21A, described above.

During operation, a sample fluid, such as blood, is received by the sample collection element 605 while the pump 620 may move the fluid in the fluid flow pathway in the direction of the thick arrow towards the optical measurement elements 2110-2130. When the leading edge of the fluid reaches a particular optical measurement element 2110-2125 (all optical measurement elements except the last optical measurement element in the pathway), the particular optical measurement element 2110-2125 may send a signal to the controller and the controller may start a timer or use an algorithm to measure elapsed time.

The particular optical measurement element 2110-2125 may make one or more light intensity measurements of the light that goes through the fluid and may send the measurements to the controller 520. For example, the particular optical measurement element 2110-2125 may make the measurements after a quantity of fluid is under the particular optical measurement element 2110-2125 (e.g., the optical measurement element 2110-2125 may be configured to make the measurements after a delay or the controller 520 may send a signal to the optical measurement element after the pump 620 moves the fluid in the fluid pathway for a few pulses (e.g., and without limitations, 1 to 10 pulses).

When the leading edge of the fluid reaches the next optical measurement element 2115-2130 in the pathway, the optical measurement element may send a signal to the controller and the controller may stop the counter and save the value of the counter. If this optical measurement element is not the last optical measurement element 2130 in the pathway, the controller 520 may start a new counter and may repeat the above process when the leading edge of the fluid reaches another optical measurement element in the pathway. The optical measurement element may also make one or more light intensity measurements and send the measurements to the controller 520, as described above.

When the fluid reaches the last optical measurement element 2130 in the pathway, the controller 520 may stop the last counter and save the value of the last counter. In some embodiments, the controller may operate the pump 620 for a few more pulses e.g., and without limitations, 1 to 10 pulses) to bring a quantity of fluid under the optical measurement element 2130. The controller may then stop the pump and may receive one or more light intensity measurements of the light that goes through the fluid from the optical measurement element 2130. As described below, the counter values (and the known distances d1-dm between the consecutive optical measurement elements 2110-2130), the light intensity measurements, and/or their combination may be used to determine indications of blood viscosity, blood thinness/thinness, and/or blood coagulation.

Figure 22A:
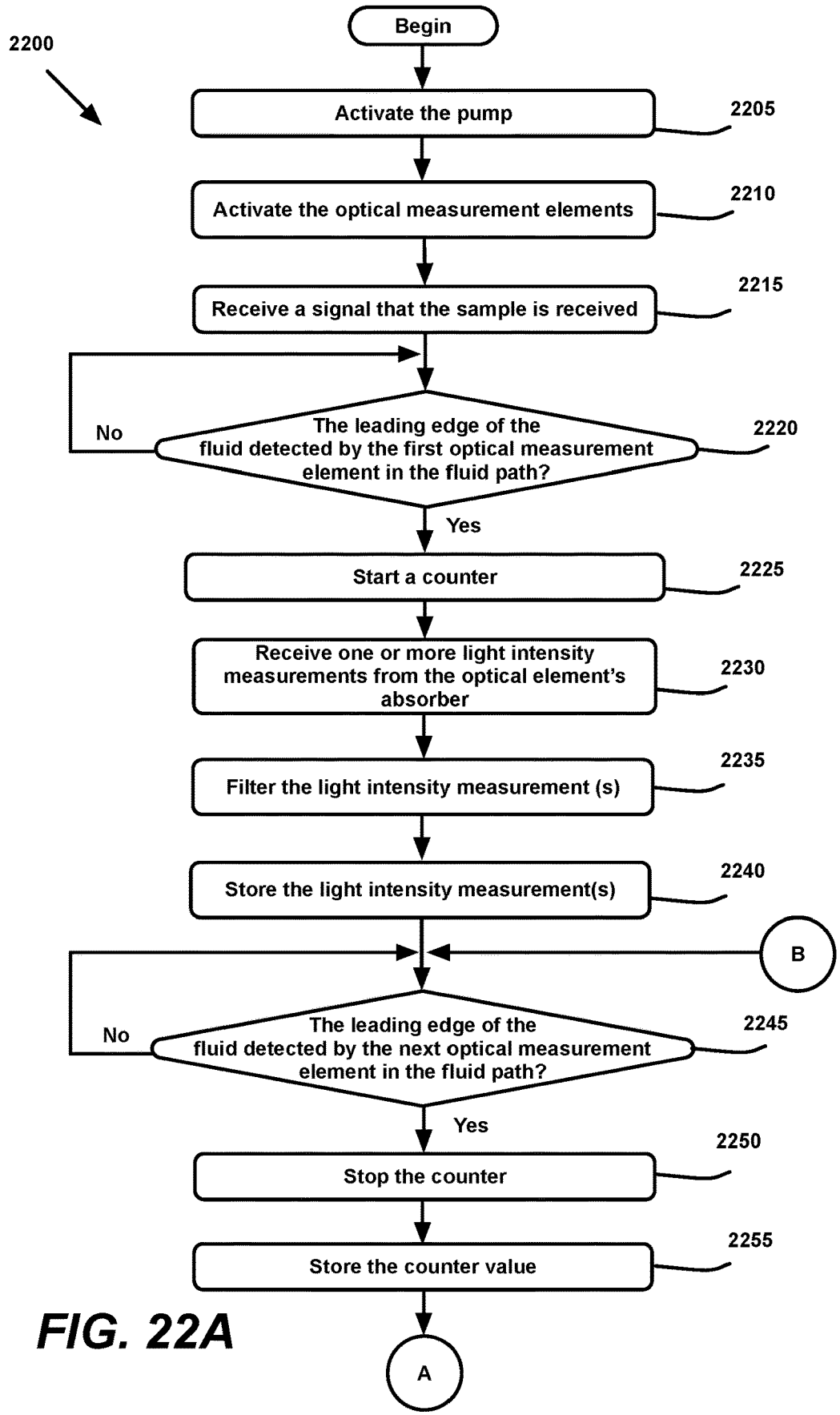
FIGS. 22A-22B illustrate a flow chart of an exemplary process that uses the sample processing module of FIG. 21A or FIG. 21B to measure the time for the leading edge of a sample to move between two optical measurement elements.
Figure 22B:
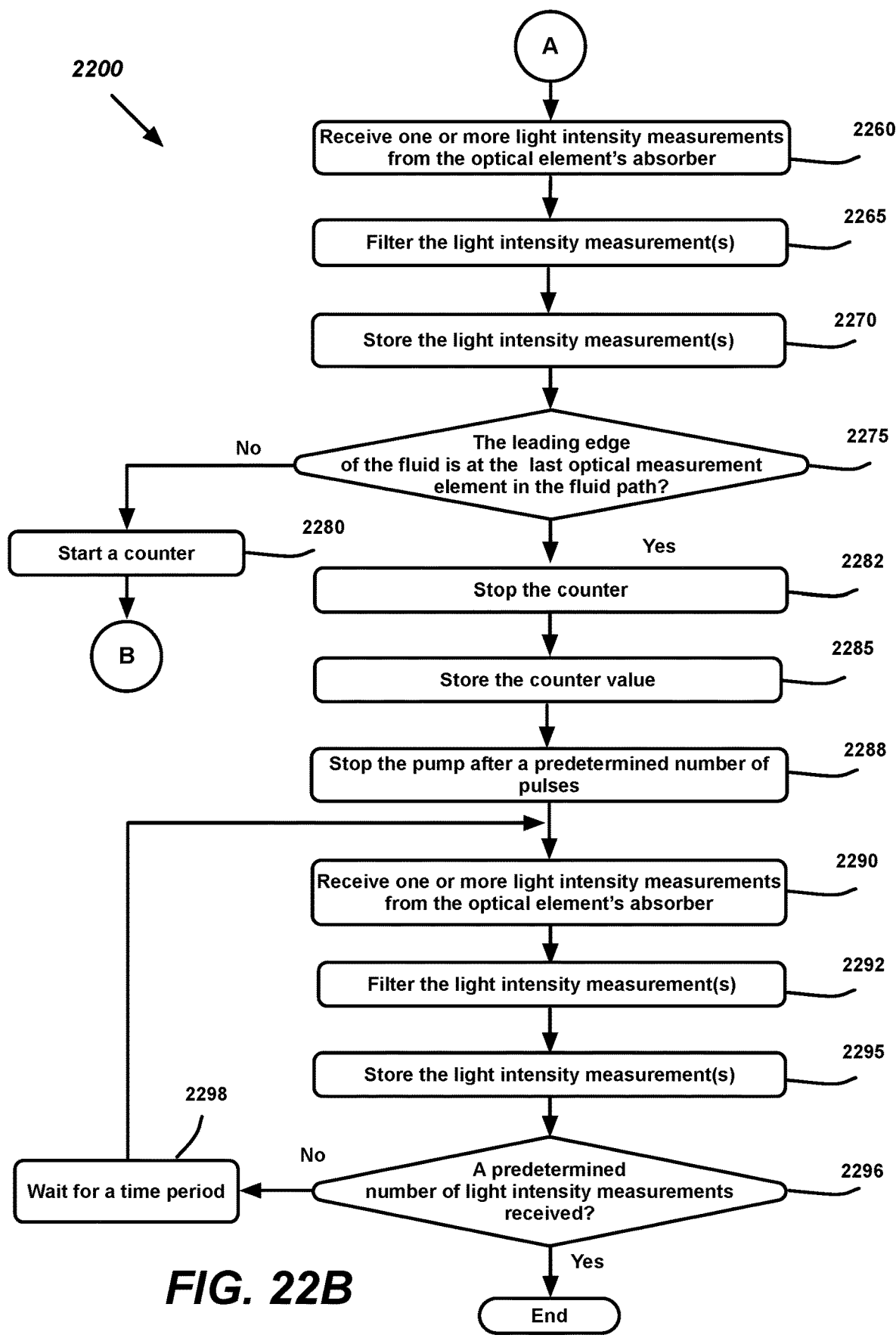

FIGS. 22A-22B illustrate a flow chart of an exemplary process 2200 that uses the sample processing module 2100 of FIG. 21A or the sample processing module 2150 of FIG. 21B to measure the time that the leading edge of the sample moves between two optical measurement elements. Such a process may be executed by the SCTD 100 (e.g., by the controller 520 of FIG. 5). As shown, the process 2200 may activate (at 2205) the pump (e.g., the pump 620 of FIG. 21A or 21B). The process 2100 may activate (at 2210) the optical measurement elements (e.g., the optical measurement elements 610-615 of FIG. 21A or 2110-2130 of FIG. 21B).

The process 2200 may receive (at 2215) a signal that the sample is received by the SCTD. The sample, in some embodiments, may be taken as described above with reference to operation 1650 (FIG. 16) and process 1700 (FIG. 17). The sample may also be taken from a container or a tube. As described below, each model of the SCTD may be calibrated once to map the measurement results of the SCTDs of that model with the results of the PT test. During such a calibration operation non-diluted and diluted samples of the fluid may be received by the SCTD from a container or a tube (instead of directly extracted by the SCTD from a person).

Next, the process 2200 may determine (at 2220) whether the leading edge of the fluid is detected by the first optical measurement element. With reference to FIG. 21A-21B, the sample fluid may travel in the direction of the thick arrow. Once the leading edge of the sample fluid reaches the optical measurement element 610 (FIG. 21A) or 2110 (FIG. 21B), the optical measurement element may detect the presence of the fluid in the fluid flow pathway as described above with reference to the detection of the leading edge 1170 of fluid (FIG. 11).

The process 2200 may iteratively or continuously attempt to detect fluid until the process determines that fluid has been detected, at which point, the process 2200 may activate (at 2225) a counter or other timing algorithm. For example, the controller of the SCTD may start a counter. Such a counter may be a digital and/or analog timer. In some embodiments, the counter may specify a duration during which the fluid is detected. In other embodiments, the counter may specify a number of pump motor pulses to be applied (or a duration during which pulses are applied). The counter may be incremented at regular intervals (e.g., each clock period) when used to measure duration of time.

In some embodiments, as described above, the output of the optical measurement element output may be converted to a digital or analog signal. In such cases, the signal may be analyzed in various appropriate ways in order to generate a "count" value (where such a value, in addition to being a literal counter or timer, may include any appropriate signal analysis). For instance, some embodiments may integrate the signal to calculate an area under a curve that may be used as the count value in order to determine a volume. As another example, the signal may be associated with various thresholds that may be used to activate or deactivate the counter (e.g., the counter value may increase when the signal is above a threshold and be held constant when the signal is below the threshold).

The process 2200 may receive (at 2230) one or more light intensity measurements from the absorber of the light measurement element that has detected the leading edge of the fluid (e.g., as described above with reference to FIG. 21A or 21B). The process 2200 may optionally filter (at 2235) the light intensity measurement(s). Such filtering may include, for instance, averaging or other smoothing, gain or other normalizing adjustments, color filtering or other signal processing, etc. The filtering may be performed by a resource such as filter 1240 (FIG. 12). The process 2200 may store (at 2240) the (filtered and/or unfiltered) light intensity measurement(s).

Next, the process 2200 may determine (at 2245) whether the leading edge of the fluid is detected by the next optical measurement element in the pathway. With reference to FIGS. 21A-21B, the sample fluid may travel in the direction of the thick arrow. Once the leading edge of the sample fluid reaches the next optical measurement element in the pathway, the optical measurement element may detect the presence of the fluid in the fluid flow pathway as described above with reference to the detection of the leading edge 1170 of fluid (FIG. 11).

The process 2200 may iteratively or continuously attempt to detect fluid until the process determines that fluid has been detected, at which point, the process 2200 may stop (at 2250) the counter (or the timing algorithm). The process 2200 may store (at 2255) the counter value (or the results of the timing algorithm).

The process 2200 may receive (at 2260) one or more light intensity measurements from the absorber of the light measurement element that has detected the leading edge of the fluid (e.g. as described above with reference to FIG. 21 or 21B). The process 2200 may optionally filter (at 2265) the light intensity measurement(s). Such filtering may include, for instance, averaging or other smoothing, gain or other normalizing adjustments, color filtering or other signal processing, etc. The filtering may be performed by a resource such as filter 1240 (FIG. 12). The process 2200 may store (at 2270) the (filtered and/or unfiltered) light intensity measurement(s).

The process 2200 may then determine (at 2275) whether the leading edge of the fluid is at the last optical measurement element in the fluid pathway. For example, the process 2200 may determine that the optical measurement element that detected the leading edge of the fluid (at 2245) is the optical measurement element 615 (FIG. 21A) or the optical measurement element 2130 (FIG. 21B).

When the leading edge of the fluid is not at the last optical measurement element in the fluid pathway, the process 2200 may start (at 2280) a new counter and may proceed to 2245, which was described above.

Otherwise, the process 2200 may stop (at 2282) the counter (or the timing algorithm). The process 2200 may store (at 2285) the counter value (or the results of the timing algorithm).

The process 2200 may stop (at 2288) the pump after a predetermined number of pulses (or after a predetermined time period). With reference to FIG. 21A or 21B, the pump 620 may provide one or more pulses to move the leading edge of the fluid forward such that the fluid moves under the emitter 1110 and the absorber 1120 (FIG. 11) of the last optical measurement element 615 (FIG. 21A) or 2130 (FIG. 21B). The pump 620 may then be stopped. In the embodiments that the pump 620 is not part of the disposable cartridge portion of the SCTD, stopping the pump may allow the pump 620 to be reused across multiple cartridges.

With further reference to FIG. 22, the process 2200 may receive (at 2290) one or more light intensity from by the optical element's absorber. The process 2200 may optionally filter (at 2592) the light intensity measurement(s). Such filtering may include, for instance, averaging or other smoothing, gain or other normalizing adjustments, color filtering or other signal processing, etc. The filtering may be performed by a resource such as filter 1240 (FIG. 12).

The process 2200 may store (at 2595) the light intensity measurement(s) (and/or the filtered light intensity measurement(s)). As described below, the counter values (and the known distances between the consecutive optical measurement elements), the light intensity measurements, and/or their combination may be used to determine indications of blood viscosity, blood thinness/thickness, and/or blood coagulation.

Next, the process 2200 may determine (at 2296) whether a predetermined number of light intensity measurements is received from the last optical measurement element in the pathway. If yes, the process 2200 may end. Otherwise, the process 2200 may wait (2298) for a time period. The time period may be programmable and, as described below, may be the interval needed to provide a curve of blood thickness/thinness change, and/or a curve of blood coagulation over a period of time. The process 2200 may then proceed to 2290, which was described above to receive additional light intensity measurement(s).

Different embodiments may perform some or all operations of process 2200. For example, in some embodiments the process 2200 may not receive light intensity measurement. In these embodiments, the pump is stopped at 2288 and operations 2230-2240, 2260-2270, and 2290-2298 are skipped. In some embodiments the process 2200 may not measure the time the fluid travels between the optical measurement elements. In these embodiments, operations 2225, 2250-2255, 2280-2288 may be skipped. Some embodiments may determine an indication of the blood viscosity, the blood thickness/thinness, and/or the blood coagulation at only one point in time. These embodiments may skip operations 2296-2298.

Figure 23A:
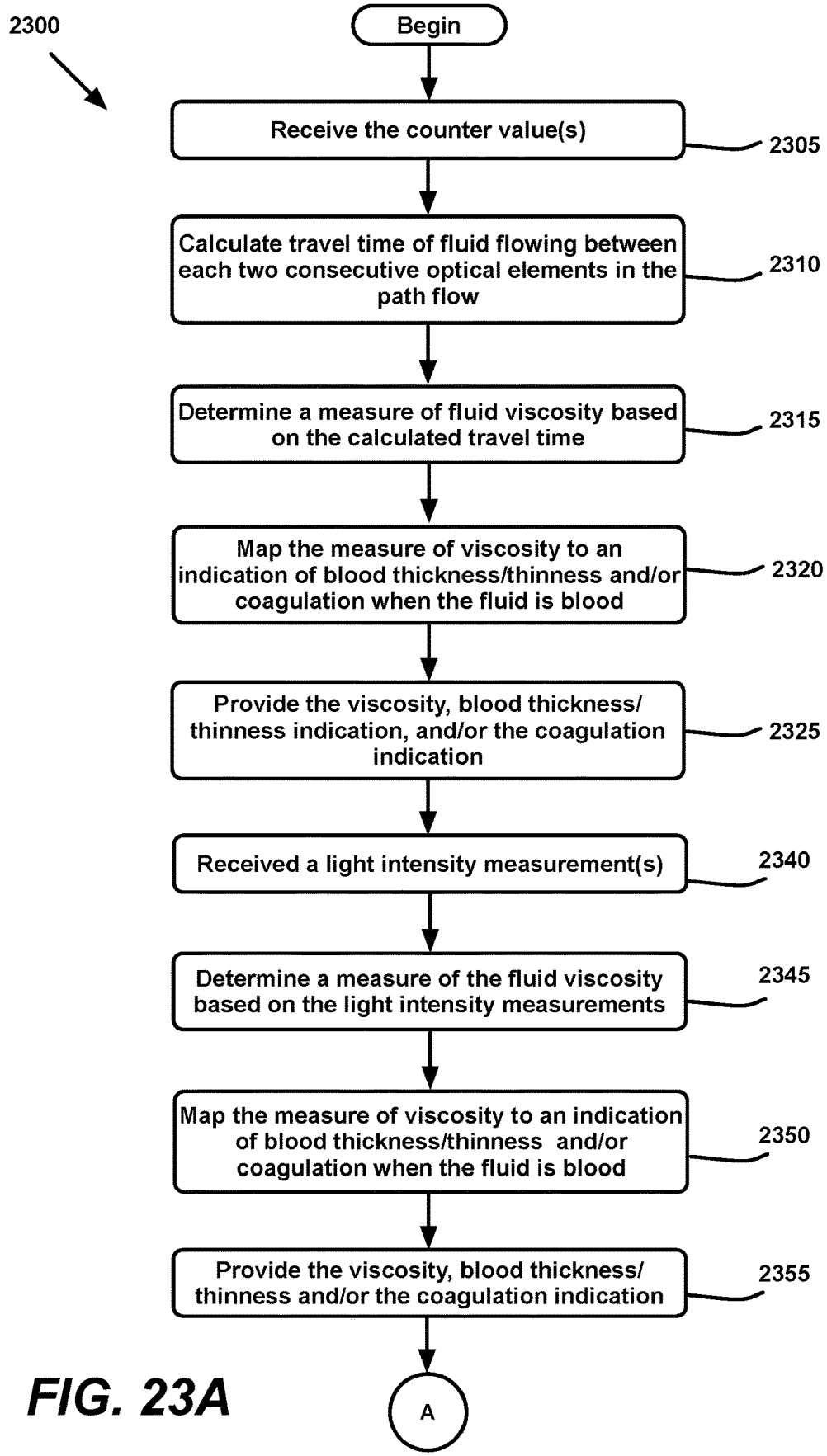
FIGS. 23A-23B illustrate a flow chart of an exemplary process that determines a measure of blood thickness/thinness and/or blood coagulation based on the time blood travels between two points and/or the light intensity of the blood.
Figure 23B:
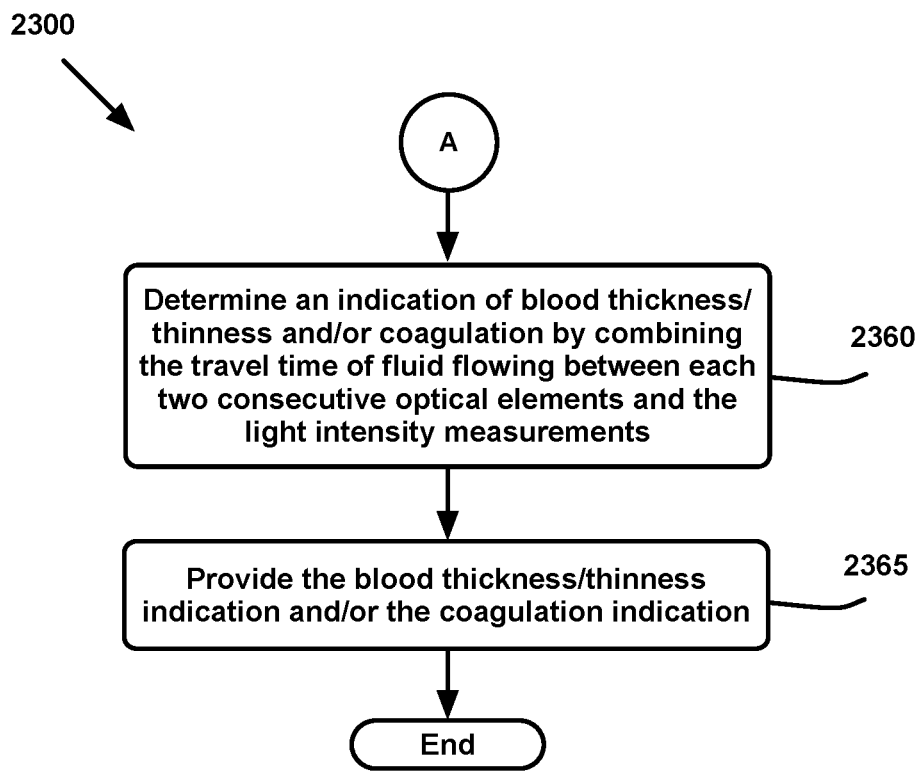

FIGS. 23A-23B illustrate a flow chart of an exemplary process that determines a measure of blood thickness/thinness and/or blood coagulation based on the time blood travels between two points in the fluid flow pathway and/or the light intensity of the blood. Such a process may be executed by the SCTD 100 (e.g., by the controller 520 of FIG. 5).

As shown, the process 2300 may receive (at 2305) the counter value(s) to determine the travel time of the fluid between the two optical measurement elements in the fluid flow pathway. As described above with reference to operation 2225, the counter value may specify a duration during which the fluid travels between the two optical measurement elements, may specify a number of pump motor pulses to be applied (or a duration during which pulses are applied), may be incremented at regular intervals (e.g., each clock period) when used to measure duration of time, etc.

The process 2300 may calculate (at 2310) the travel time of the fluid flowing between each two consecutive optical measurement elements based on the corresponding counter value (or based on the results of the corresponding time algorithm used by the process 2200). The process 2300 may then determine (at 2315) a measure of the fluid viscosity based on the calculated travel time. For example, and without limitations, the process 2300 may use the travel time as an indication of the viscosity or the process 2300 may determine the viscosity based on the travel time and properties of the particular type of fluid in the sample.

When the fluid is blood (or a derivative thereof), the process 2300 may map (at 2320) the measure of viscosity to an indication of blood thickness/thinness and/or blood coagulation. For example, the measurements of each particular model of the SCTD device (e.g., an SCTD device with specific types of components, a particular distance between the two optical measurement elements, particular diameter(s) of the fluid flow pathway, a particular pump, etc.) may be compared with the measurements of a PT test device for different samples and different dilutions of each sample. The process 2300 may map the viscosity measure into blood thickness/thinness and/or coagulation indication using a table look up. The table values may be generated by a process such as the process 2700, described below.

The PT test results may be expressed as prothrombin time (in seconds) being a function of the percentage of the prothrombin activity (a measure of blood coagulation) (e.g., in a progressively diluted plasma). The results of the SCTD device measurements and the PT test device measurements may be compared to provide a mapping of the viscosity measurement of the SCTD device to the PT measurement of the PT test device.

The process 2300 may then provide (at 2325) the measure of viscosity, the blood thickness/thinness indication, and/or the coagulation indication. The results may be provided via the SCTD 100 (e.g., using UI 120), a user device or medical device 510, and/or other appropriate ways. Some embodiments may send the results (and/or measure or intermediate values) to multiple external devices or systems using an element such as communication module 560.

The process 2300 may receive (at 2340) one or more light intensity measurement(s) made by the optical measurement element(s). For example, as described above, the process 2300 may receive light intensity measurements made by the optical measurement elements 610-615 of FIG. 21A or 2110-2130 of FIG. 21B. The process 2300 may receive the light intensity measurement from the optical measurement elements or the process 2300 may receive the light intensity measurement stored in a storage device (e.g., stored by the process 2200 of FIGS. 22A-22B).

The process 2600 may determine (at 2345) a measure of the fluid's viscosity based on the light intensity measurements. The more light intensity measured means the more light has passed through the liquid, which means the fluid is thinner and has less viscosity. The less light intensity measured means the less light has passed through the liquid, which means the fluid is thicker and has more viscosity.

When the fluid is blood (or a derivative thereof), the process 2300 may map (at 2350) the measure of viscosity to an indication of blood thickness/thinness and/or coagulation. For example, the results of each particular model of the SCTD device (e.g., an SCTD device with specific types of components, a particular distance between the two optical measurement elements, particular diameter(s) of the fluid flow pathway, a particular pump, etc.) may be compared with the results of a PT test device for different samples and different dilutions of each sample.

The viscosity measure used for the mapping (at 2350) may be the measure of the viscosity determined at operation 2345, or a function of the measure of the viscosity determined at operation 2345 and the measure of the viscosity determined at operation 2315.

In some embodiments, in addition to, or in lieu of, mapping the viscosity measure to the indication of blood thickness/blood thinness and/or the indication of the blood coagulation, the process 2300 may use a combination of the travel time of the fluid flowing between the first and second optical elements (calculated at 2310) and the light intensity measurements received (at operation 2340 and/or 2365) to determine (at 2360) an indication of the blood thickness/thinness and/or blood coagulation. This combination may be more robust that the PT test due to combing of the two different measurement techniques. In addition, the test performed by the SCTD of the present embodiments uses whole blood samples as opposed on the PT test that uses plasma. The process 2300 may then provide (at 2365) the blood thickness/thinness indication, and/or the coagulation indication as described above with reference to operation 2235.

The results of the SCTD device measurements and the PT test device measurements may be compared to provide a mapping of the viscosity measurement of the SCTD device to the PT measurement of the PT test device. When the process 2300 receives multiple light intensity measurements, the process 2300 may provide a curve that shows an indication of blood thickness/thinness and/or an indication of blood coagulation, similar to a curve generated by a PT test.

The process 2300 may then provide (at 2365) the viscosity, the blood thickness/thinness indication, and/or the coagulation indication. The results may be provided via the SCTD 100 (e.g., using UI 120), a user device or medical device 510, and/or other appropriate ways. Some embodiments may send the results (and/or measure or intermediate values) to multiple external devices or systems using an element such as communication module 560. The process 2300 may end.

Figure 24:
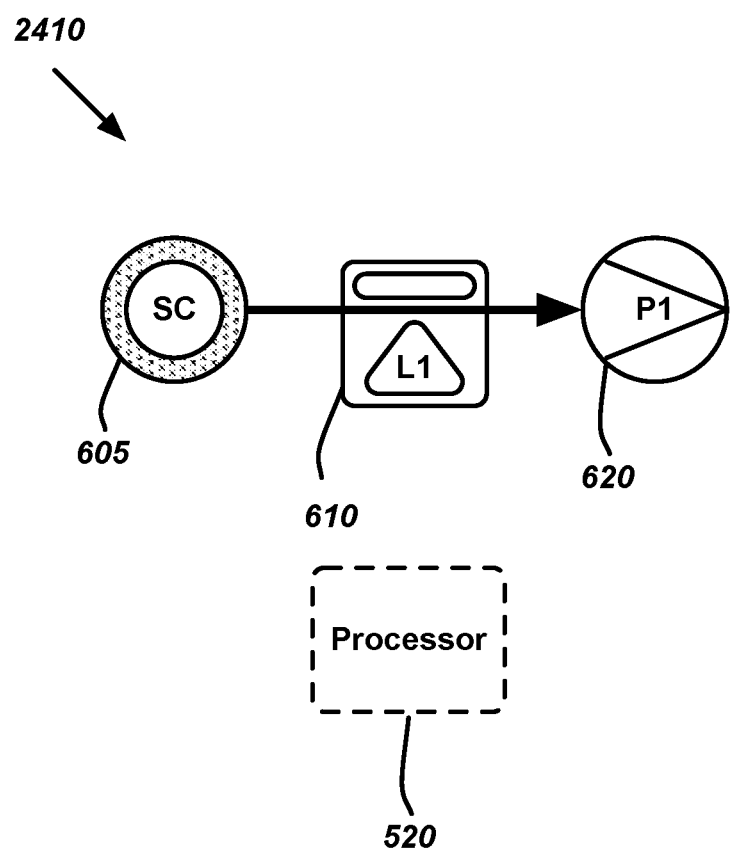
FIG. 24 illustrates a schematic block diagram of an exemplary embodiment of the sample processing module with one optical measurement element, included in the sample collection and testing device of FIG. 1.

FIG. 24 illustrates a schematic block diagram of an exemplary embodiment of the sample processing module 2410 included in the sample collection and testing device of FIG. 1. The sample processing module 2410 may be used to determine the viscosity of a fluid such as blood. As shown, this example module may include a sample collection element 605, an optical measurement element 610 (e.g., lasers, LED light sources, etc.), and a pump 620. The fluid flow path (shown by thick arrow) may be a capillary tube.

The sample processing module 2410, in some embodiments, may include a processor 520. In other embodiments the processor 520 may be external to the sample processing module 2410. Different embodiments may include additional components, for example and without limitation, one or more cameras such as camera 570 (FIG. 6), one or more cavities such as cavities 640-655 (FIG. 6), additional optical measurement elements, additional pumps, etc. The sample collection element 605, the optical measurement element 610, the pump 620, and the processor 520 may be similar to the corresponding components of FIGS. 6-8 and 21. The pump 620 may be unidirectional or bi-directional in different embodiments. The sample collection element 605 may include an actuator, such as the actuator 335 of FIG. 3 that may include components such as a linear solenoid, a rotary motor, etc. In some embodiments, the actuator may be a controllable electronic actuator such that attributes such as depth or height, pressure, velocity, acceleration, torque, etc. may be able to be controlled based on various parameters (e.g., default values, user selections, measured values, etc.).

The sample processing module 2410, or portions thereof, may be self-contained such that each subject may use a new disposable cartridge 240 (FIG. 2). As such, the fluid collected by the cartridge may be completely contained within the cartridge and not exposed to the SCTD device 100 (FIG. 1). The cartridge elements may be made out of (and/or enclosed or embedded in) appropriate materials that are impervious to the various fluids collected or used within the sample processing module 2410. Such materials may include plastics, silicone, composites, etc. In this example, the fluid flow pathway is indicated by thicker arrows, while communicatively coupled elements are indicated by thinner lines or arrows. In addition, the components that contact the sample are indicated by a fill pattern.

In some embodiments, the disposable cartridge portion may include the sample collection element 605 and the tubing between them. Such a configuration allows the more expensive components (such as the pump 620, the optical measurement element 610, the processor 520, etc.) to be reused across multiple cartridges.

The sample collection element 605, in some embodiments, may not include a separate pump and the pump 620 may act as the pump for the sample collection element 605. The sample collection element 605, in some embodiments, may measure the amount of fluid in a sample taken by the SCTD device and stop taking further fluid when a predetermined amount of sample is taken e.g., as described above with reference to operations 1740-1750 of FIG. 17).

The controller 520 may be an electronic device capable of executing instructions and/or processing data. The controller 530 may include a processor. The controller may be able to at least partly control the operations of various other components (although various connections have been omitted for clarity). For instance, the controller 520 may receive and analyze data from the optical measurement element 610. The controller 520 may start and stop the pump 620. The controller may open or close a valve (e.g., the pinch valve 320 of FIG. 3) in the sample collection element 605. The controller 520 may have an associated memory (not shown).

During operation, a sample fluid, such as blood, is received by the sample collection element 605 while the pump 620 may pump the fluid in the direction of the thick arrow towards the optical measurement element 610. When the leading edge of the fluid reaches the optical measurement element 610, the optical measurement element 610 may send a signal to the controller and the controller may operate the pump 620 for a few more pulses to bring a quantity of fluid under the optical measurement element 610. The controller may then stop the pump and may receive one or more light intensity measurements of the light that goes through the fluid from the optical measurement element 610. As described below, the light intensity measurements may be used to determine indications of blood viscosity, blood thinness/thickness, and/or blood coagulation.

Figure 25:
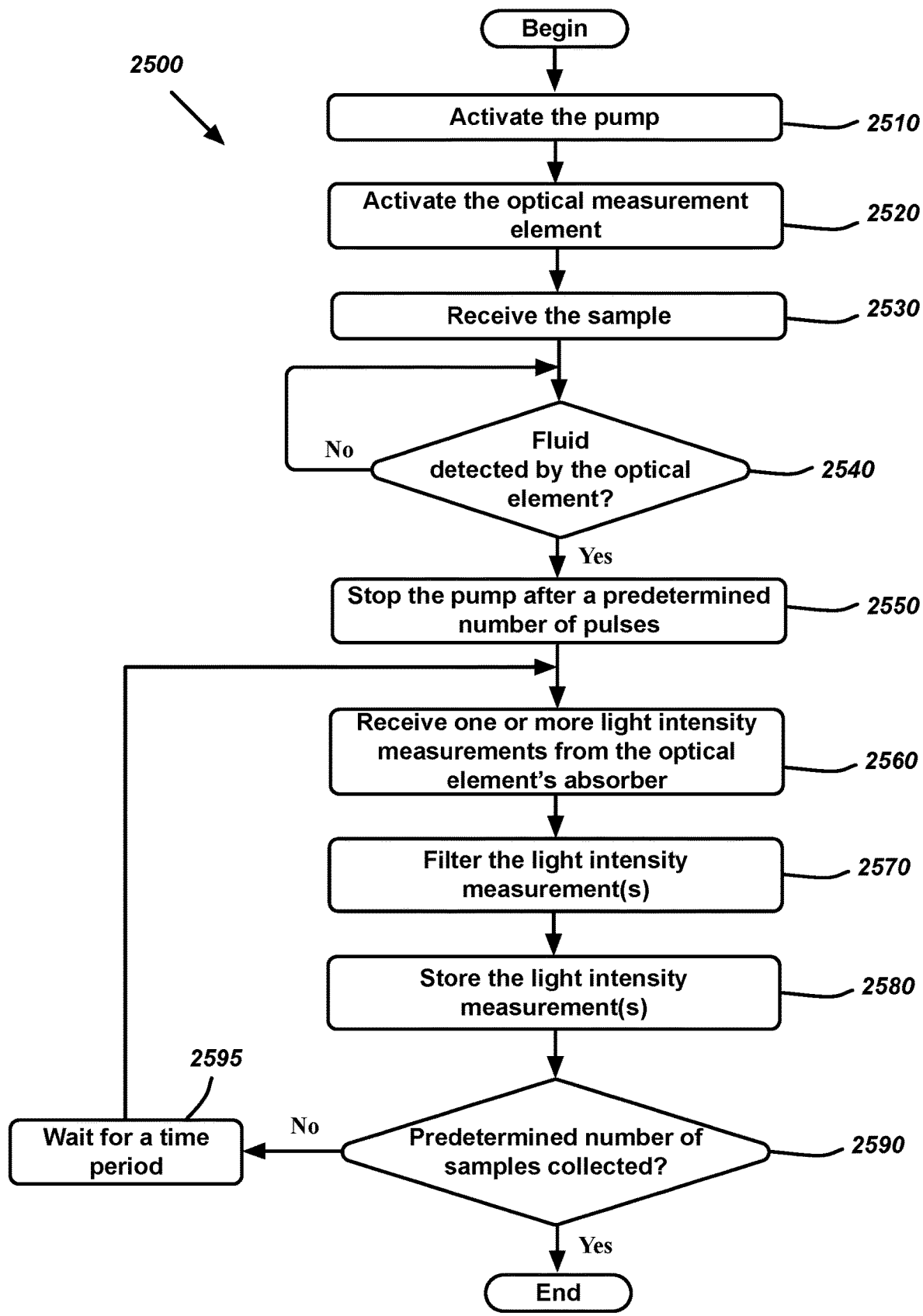
FIG. 25 illustrates a flow chart of an exemplary process that uses the sample processing module of FIG. 24 to measure the intensity of light that passes through the sample.

FIG. 25 illustrates a flow chart of an exemplary process 2500 that uses the sample processing module 2410 of FIG. 24 to measure the intensity of light that passes through the sample. Such a process may be executed by the SCTD 100 (e.g., by the controller 520 of FIG. 5). As shown, the process 2500 may activate (at 2510) the pump (e.g., the pump 620 of FIG. 24). The process 2500 may activate (at 2520) the optical measurement element (e.g., the optical measurement element 610 of FIG. 24).

The process 2500 may receive (at 2530) the sample. The sample, in some embodiments, may be taken as described above with reference to operation 1650 (FIG. 16) and process 1700 (FIG. 17). As described above, each model of the SCTD may be calibrated once to map the results of the SCTDs of that model with the results of a PT test device. As described above, each model of the SCTD may be calibrated once to map the measurement results of the SCTDs of that model with the results of the PT test. During such a calibration operation, non-diluted and diluted samples of the fluid may be received by the SCTD from a container or a tube.

Next, the process 2500 may determine (at 2540) whether the leading edge of the fluid is detected by the optical measurement element. With reference to FIG. 24, the sample fluid may travel in the direction of the thick arrow from the sample collection element 605 towards the optical measurement element 610. Once the leading edge of the sample fluid reaches the optical measurement element 610, the optical measurement element 610 may detect the presence of the fluid in the fluid flow pathway as described above with reference to the detection of the leading edge 1170 (FIG. 11).

The process 2500 may iteratively or continuously attempt to detect fluid until the process determines that fluid has been detected, at which point, the process 2500 may stop (at 2550) the pump after a predetermined number of pulses (or after a predetermined time period). With reference to FIG. 24, the pump 620 may provide one or more pulses to move the leading edge of the fluid forward such that the fluid moves under the emitter 1110 and the absorber 1120 (FIG. 11) of the optical measurement element 610. The pump 620 may then be stopped. In the embodiments that the pump 620 is not part of the disposable cartridge portion of the SCTD, stopping the pump may allow the pump 620 to be reused across multiple cartridges.

With further reference to FIG. 25, the process 2500 may make (at 2560) a light intensity measurement by the optical element's absorber. The process 2500 may optionally filter (at 2570) the light intensity measurement. Such filtering may include, for instance, averaging or other smoothing, gain or other normalizing adjustments, color filtering or other signal processing, etc. The filtering may be performed by a resource such as filter 1240 (FIG. 12)

The process 2500 may then optionally store (at 2580) the light intensity measurement (or the filtered light intensity measurement). As described below with reference to FIG. 26, the light intensity may be used to determine the viscosity of the fluid based.

Next, the process 2500 may determine (at 2590) whether a predetermined number of samples is collected. If yes, the process 2500 may end. Otherwise, the process 2500 may wait (2595) for a time period. The time period may be programmable and, as described below, may be the interval needed to provide a curve of blood thickness/thinness change, and/or a curve of blood coagulation over a period of time. The process 2500 may then proceed to 2560, which was described above to make another light intensity measurement. Some embodiments may determine the blood viscosity, the blood thickness/thinness, and/or the blood coagulation at only one point in time. These embodiments may skip operations 2590-2595.

Figure 26:
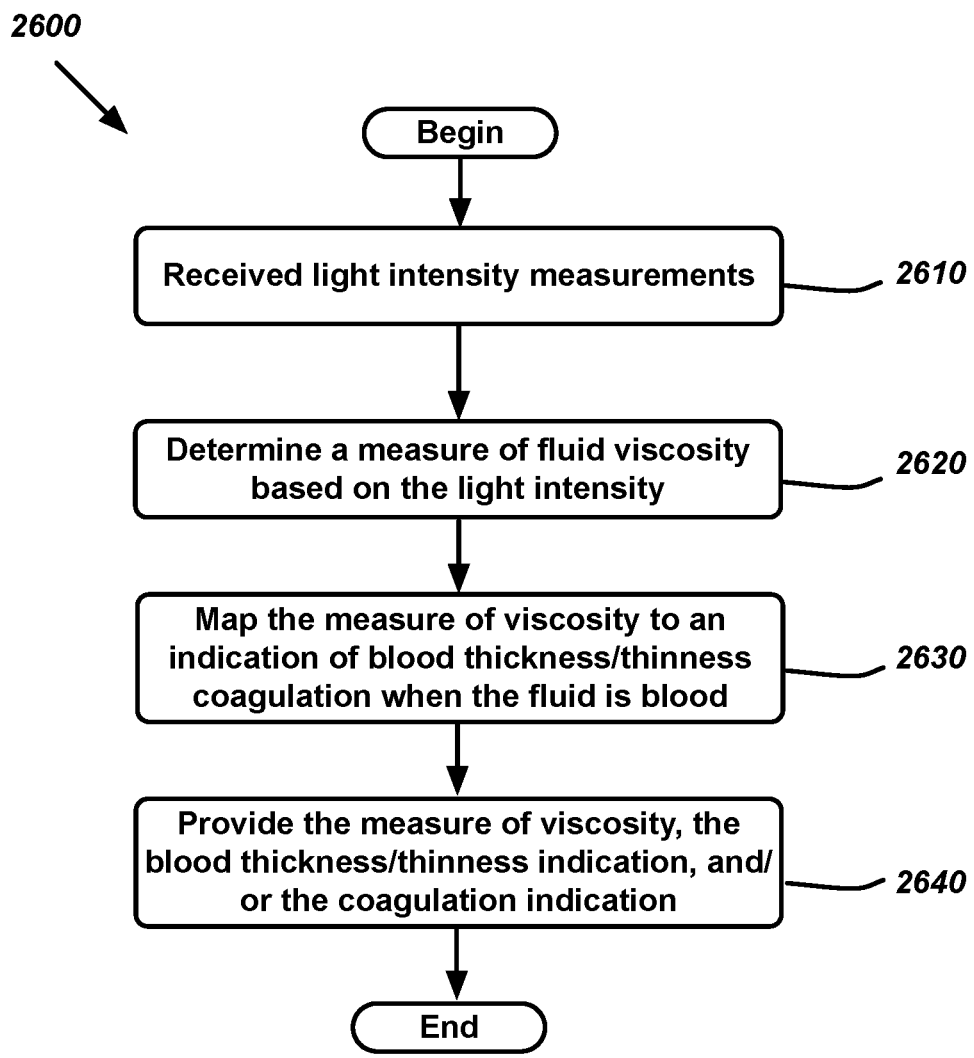
FIG. 26 illustrates a flow chart of an exemplary process that determines a measure of blood thickness/thinness and/or blood coagulation based on the light intensity measurement of the blood.

FIG. 26 illustrates a flow chart of an exemplary process 2600 that determines a measure of blood thickness/thinness and/or blood coagulation based on the light intensity measurement of the blood. Such a process may be executed by the SCTD 100 (e.g., by the controller 520 of FIG. 5). As shown, the process 2600 may receive (at 2610) the light intensity measurements made by an optical measurement element (e.g., the optical measurement element 610 of FIG. 24). The process 2600 may determine (at 2620) a measure of the fluid's viscosity based on the measured light intensity. The more light intensity measured means the more light has passed through the liquid, which means the fluid is thinner and has less viscosity. The less light intensity measured means the less light has passed through the liquid, which means the fluid is thicker and has more viscosity.

When the fluid is blood (or a derivative thereof), the process 2600 may map (at 2630) the measure of viscosity to an indication of blood thickness/thinness and/or blood coagulation. For example, the results of each particular model of the SCTD device (e.g., an SCTD device with specific types of components, a particular distance between the two optical measurement elements, particular diameter(s) of the fluid flow pathway, a particular pump, etc.) may be compared with the results of a PT test device for different samples and different dilutions of each sample. The results of the SCTD device measurements and the PT test device measurements may be compared to provide a mapping of the viscosity measurement of the SCTD device to the PT measurement of the PT test device.

When the process 2600 receives multiple light intensity measurements, the process 2600 may provide a curve that shows an indication of blood thickness/thinness and/or an indication of blood coagulation, similar to a curve generated by a PT test. The process 2600 may map the measure of viscosity into coagulation indication using a table look up. The table values may be generated by a process such as the process 2700, described below.

The process 2600 may then provide (at 2640) the measure of viscosity, the blood thickness/thinness indication, and/or the coagulation indication. The results may be provided via the SCTD 100 (e.g., using UI 120), a user device or medical device 510, and/or other appropriate ways. Some embodiments may send the results (and/or measure or intermediate values) to multiple external devices or systems using an element such as communication module 560. The process 2600 may then end. Some embodiments may use the light intensity measurements received (at 2610) to provide (at 2630) an indication of blood thickness/thinness and/or an indication of blood coagulation without determining a measure of viscosity.

Figure 27:
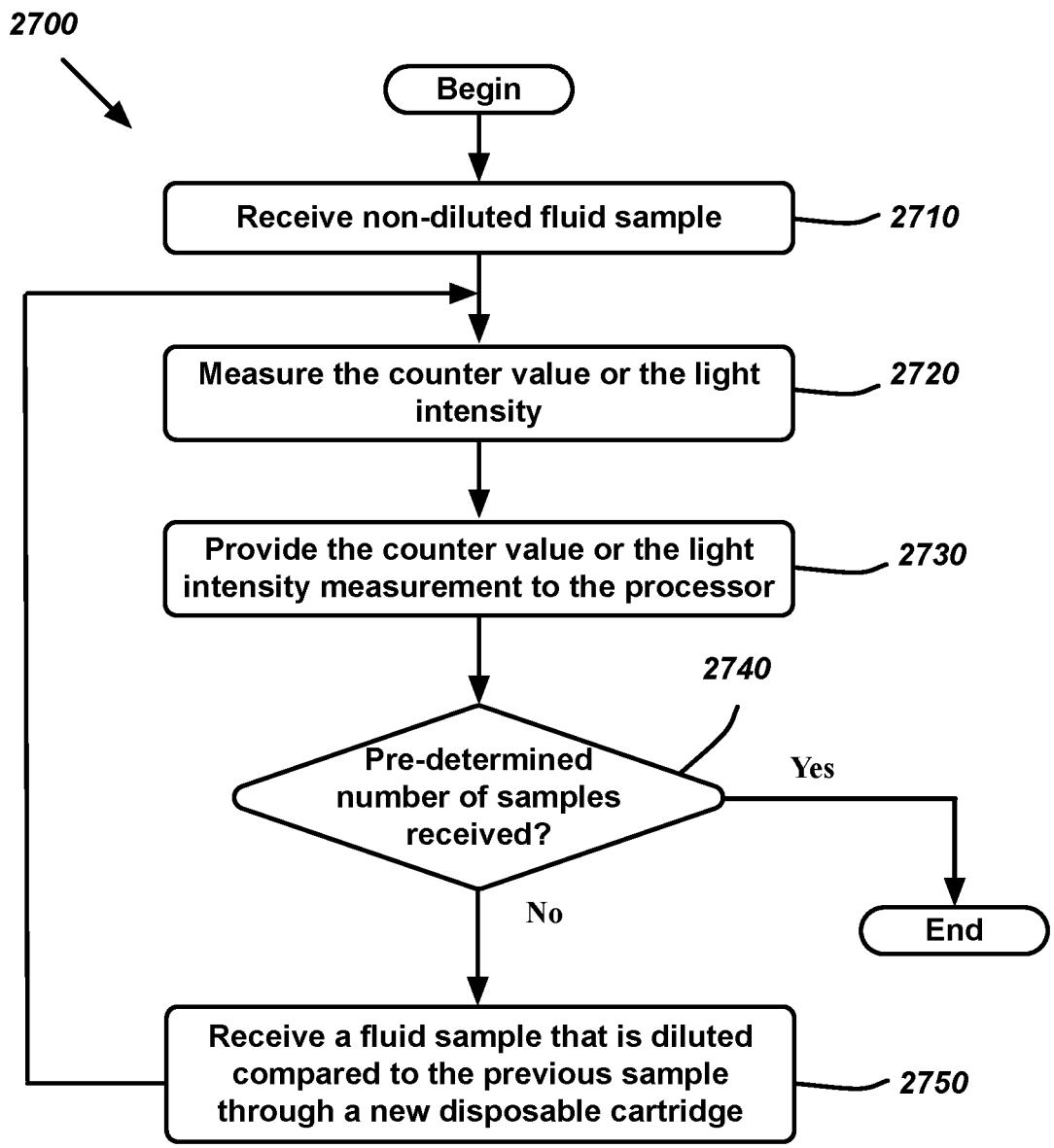
FIG. 27 illustrates a flow chart of an exemplary process that receives different samples of a fluid and makes measurements to provide data for the calibration of the SCTD with PT test results.

FIG. 27 illustrates a flow chart of an exemplary process 2700 that receives different samples of a fluid and makes measurements to provide data for the calibration of the measurements made by the SCTD with the measurements made by a PT test device. Such a process may be executed by the SCTD 100 (e.g., by the controller 520 of FIG. 5). As shown, the process 2700 may receive (at 2710) a quality of non-diluted fluid sample. For example, when the fluid is blood, blood sample may be collected from a person and the sample may be divided in many portions. Each portion may be diluted (e.g., with saline, water, or other appropriate fluid) by a percentage of volume. For each, each successive portion may be 50% more diluted than the immediately preceding portion. The non-diluted portion of the sample may be received (at 2710) by the process 2700.

The process 2700 may then make a counter measurement (e.g., as described above with reference to operations 2240-2270 of FIGS. 22A-22B) or the process 2700 may make a light intensity measurement (e.g., as described above with reference to operations 2540-2570 of FIG. 25). The process 2700 may then provide (at 2730) the counter value or the light intensity measurement to the processor (e.g., the processor 520 of FIG. 21A, 21B, or 24).

The process 2700 may then determine (at 2740) whether a predetermined number of samples is received. For example, the process 2700 may determine whether the number of samples received is the same as the number of the portions of the sample described above. If yes, then the process 2700 may end. Otherwise, the process 2700 may receive (at 2750, through a new disposable cartridge, a fluid sample that is diluted compared to the previous sample. The process 2700 may then proceed to 2720, which was described above.

The process 2700 may be repeated several times using non-diluted and diluted samples from different subjects. The results may be averaged and may be used, as described above, by the process 2300 in operation 2340 or the process 2600 in operation 2630.

Figure 28:
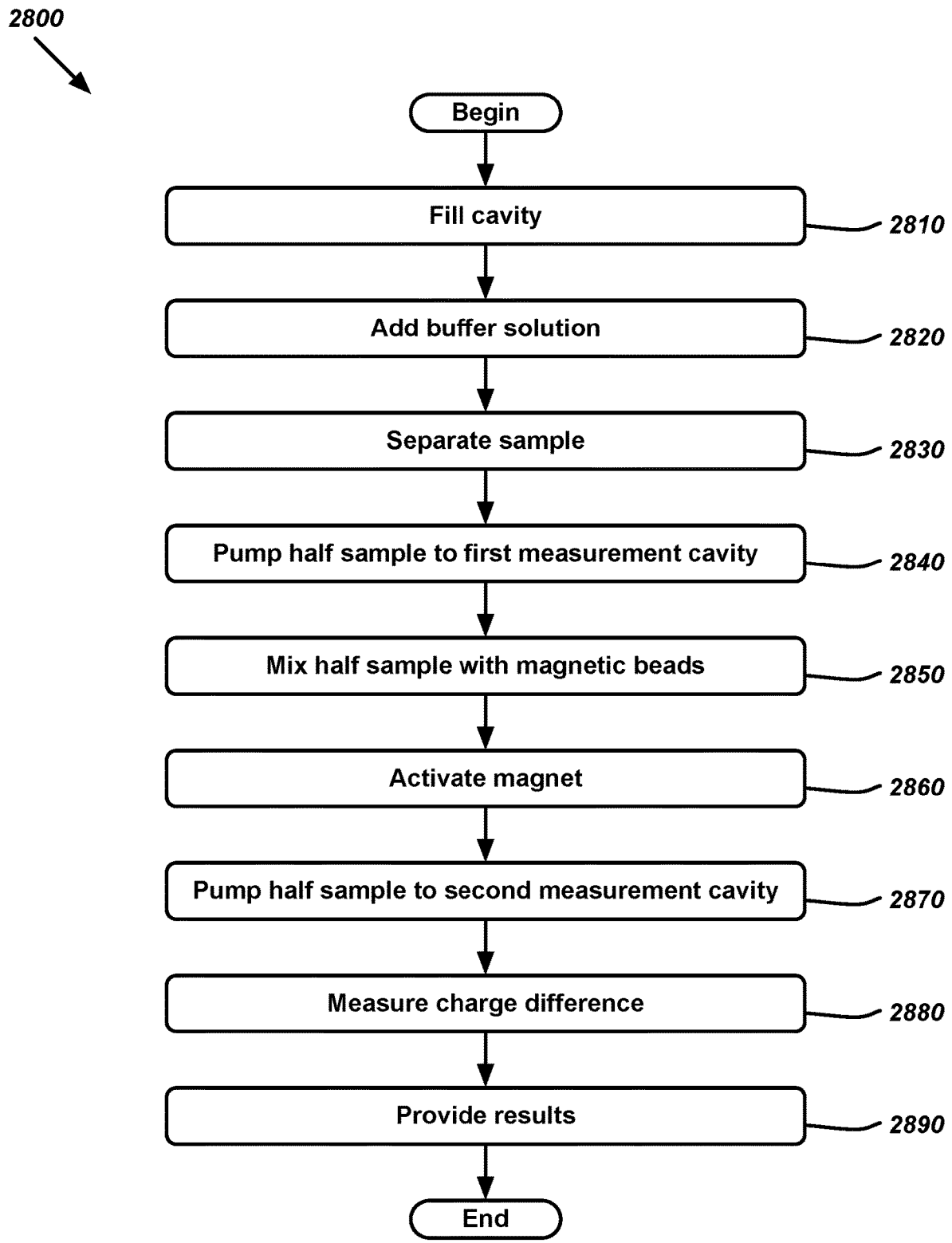
FIG. 28 illustrates a flow chart of an exemplary process that processes a sample using the sample processing module of FIG. 6.

FIG. 28 illustrates a flow chart of an exemplary process 2800 that processes a sample using the sample processing module 110 of FIG. 6. Such a process may be executed by the SCTD 100. The process may begin after a sample is taken, such as described above in reference to operation 1650 and process 1700.

As shown, process 2800 may fill (at 2810) a first cavity (e.g., cavity 640). Such a cavity may be filled using a first pump (e.g., pump 620) and a first optical sensor (e.g., sensor 610) to provide a specified amount of fluid to the cavity (e.g., cavity 640). Some embodiments may apply one thousand pulses, for example, to the pump in order to move one microliter of blood, with an accuracy of approximately one nanoliter.

In some embodiments, the optical sensor (e.g., sensor 610) may be placed before a pump (e.g., pump 620) such that when fluid is detected at the optical sensor, a stepper motor of the pump may be operated for a number of pulses in order to move a defined amount of fluid. Such sensor placement may result in improved accuracy by eliminating additional fluid that may be retained past the pump and later pulled into the associated cavity.

Next, the process may add (at 2820) a buffer solution. The buffer solution may be stored in a second cavity (e.g., cavity 645) and moved into the first cavity using a second pump (e.g., pump 625). The second pump may then be reversed and the mixture moved into the second cavity. Such operations may be performed over multiple iterations to thoroughly mix the solution.

The process may then separate (at 2830) the sample into halves (and/or other portion ratios). A third pump (e.g., pump 630) and second optical sensor (e.g., sensor 635) may be used to accurately measure the appropriate amount of fluid (whether half or some other ratio) and move (at 2840) that amount into a third cavity (e.g., cavity 650). The third cavity may include electrically charged (and/or otherwise tagged) HAAH antibodies (or any other appropriate antibody).

In addition, the second pump may be used to move (at 2840) the half sample in the second cavity to the first measurement cavity (e.g., cavity 640). The third pump may move the mixture in the third cavity between the third cavity and the second cavity to thoroughly mix the solution. At this point, any HAAH molecules in the blood sample will attach to the HAAH antibodies (or the target molecules will attach to other types of charged antibodies).

Next, the process may mix (at 2850) the half sample in the third cavity with the content of a fourth cavity (e.g., cavity 655) using a fourth pump (e.g., pump 635). The fourth cavity may include HAAH and magnetic beads that attach to any leftover HAAH antibodies that have not been attached to HAAH molecules in the blood.

The process may then activate (at 2860) the electromagnet. Next, the process may use the fourth pump to move (at 2870) the contents of the third cavity to the fourth cavity (or second measurement cavity), excluding the contents that are retained in the third cavity by the electromagnet.

The process may then measure (at 2880) the charge difference between the charge of the first cavity and the charge of the fourth cavity. The difference is proportional to the density of HAAH in the blood and may be provided as the final output of the process. After providing (at 2890) the results of the charge difference measurement, the process may end.

In addition, the results and/or other parameters (e.g., optical measurement waveforms, count values, subject information, test parameters, etc.) may be stored for future reference and analysis.

HAAH molecules (and HAAH antibodies) are described as one example only. Other embodiments may utilize various other antibodies such that the density of any target molecules in a sample may be determined.

Figure 29:
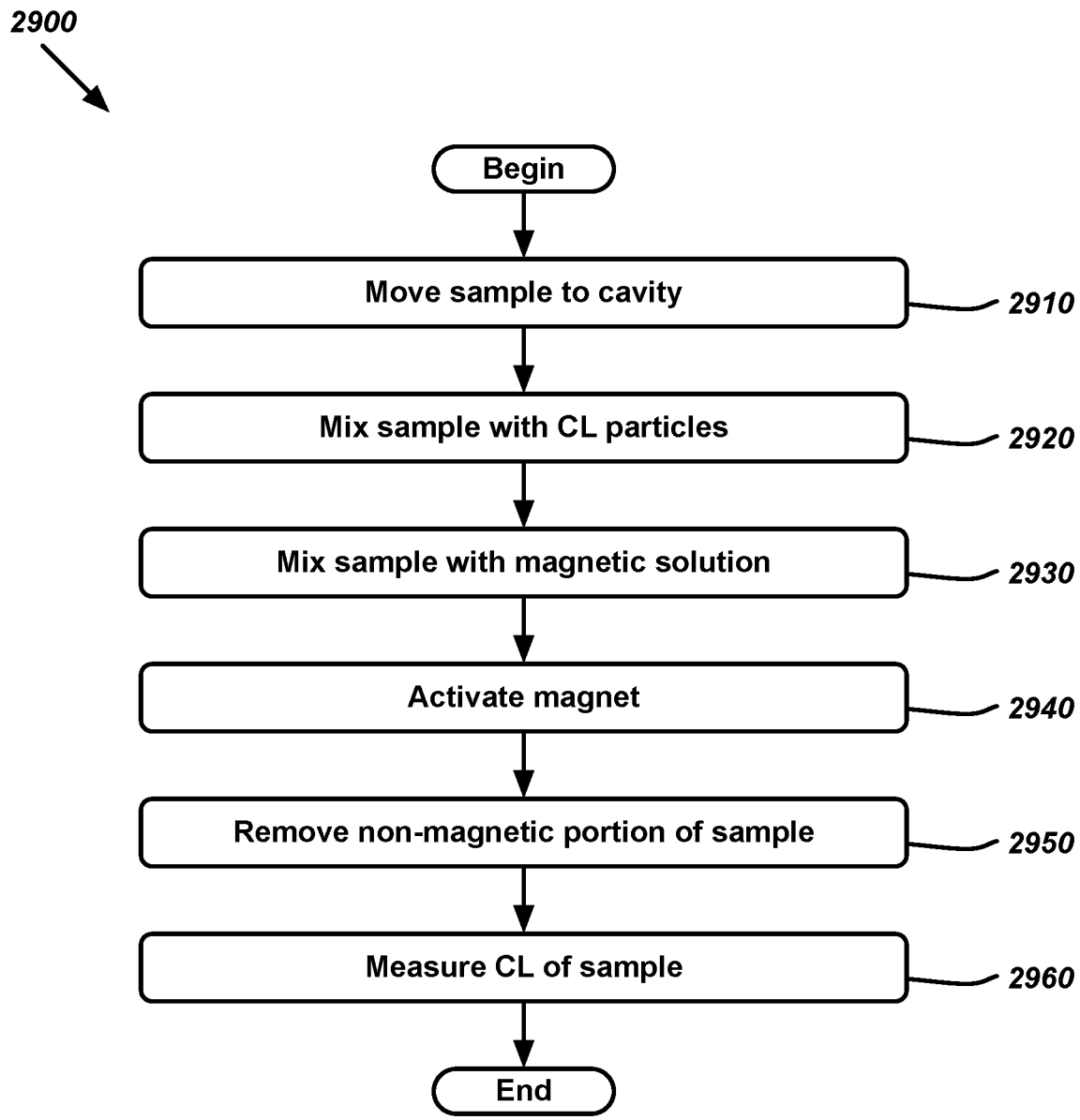
FIG. 29 illustrates a flow chart of an exemplary process that processes a sample using the sample processing module of FIG. 7.

FIG. 29 illustrates a flow chart of an exemplary process 2900 that processes a sample using the sample processing module of FIG. 7. Such a process may be executed by the SCTD 100. The process may begin after a sample is taken, such as described above in reference to operation 1650 and process 1700.

As shown, process 2900 may move (at 2910) the sample to a first cavity such as cavity 640. Such a sample may be collected via sample collection element 605 and pump 620. The operations of the pump may be at least partly controlled based on data provided from a measurement element such as element 610. The first cavity may be pre-filled with a buffer solution.

Next, the process may mix (at 2920) the sample and buffer solution with a CL agent attached to an antibody (e.g., CL attached to HAAH antibody). A second cavity, such as cavity 645, may be pre-filled with such antibodies. A pump such as pump 625 may be used to mix the contents of the first and second cavities by moving the mixture between the cavities several times.

The process may then mix (at 2930) the sample with the complementary molecule attached to magnetic beads such as those described above (e.g., HAAH protein attached to magnetic beads). A third cavity (e.g., cavity 650) may be pre-filled with such a solution and the sample may be mixed using pump 630 to move the mixture between the second and third cavities.

Next, the process may activate (at 2940) the electromagnet (e.g., magnet 660) and then remove (at 2950) the non-magnetic portion of the sample mixture. The non-magnetic portion may be removed using pump 630, for instance, such that the non-magnetic portion (which includes the bound CL agents and antibodies) may be retained in the second cavity.

Finally, the process may measure (at 2960) the CL of the mixture in the second cavity and then may end. Such a measurement may be made using a detector such as detector 700 described above. The measurement may be provided to various appropriate resources, such as a processor, user device, etc. Likewise, the measurement may be provided by a UI 120 of some embodiments.

Figure 30:
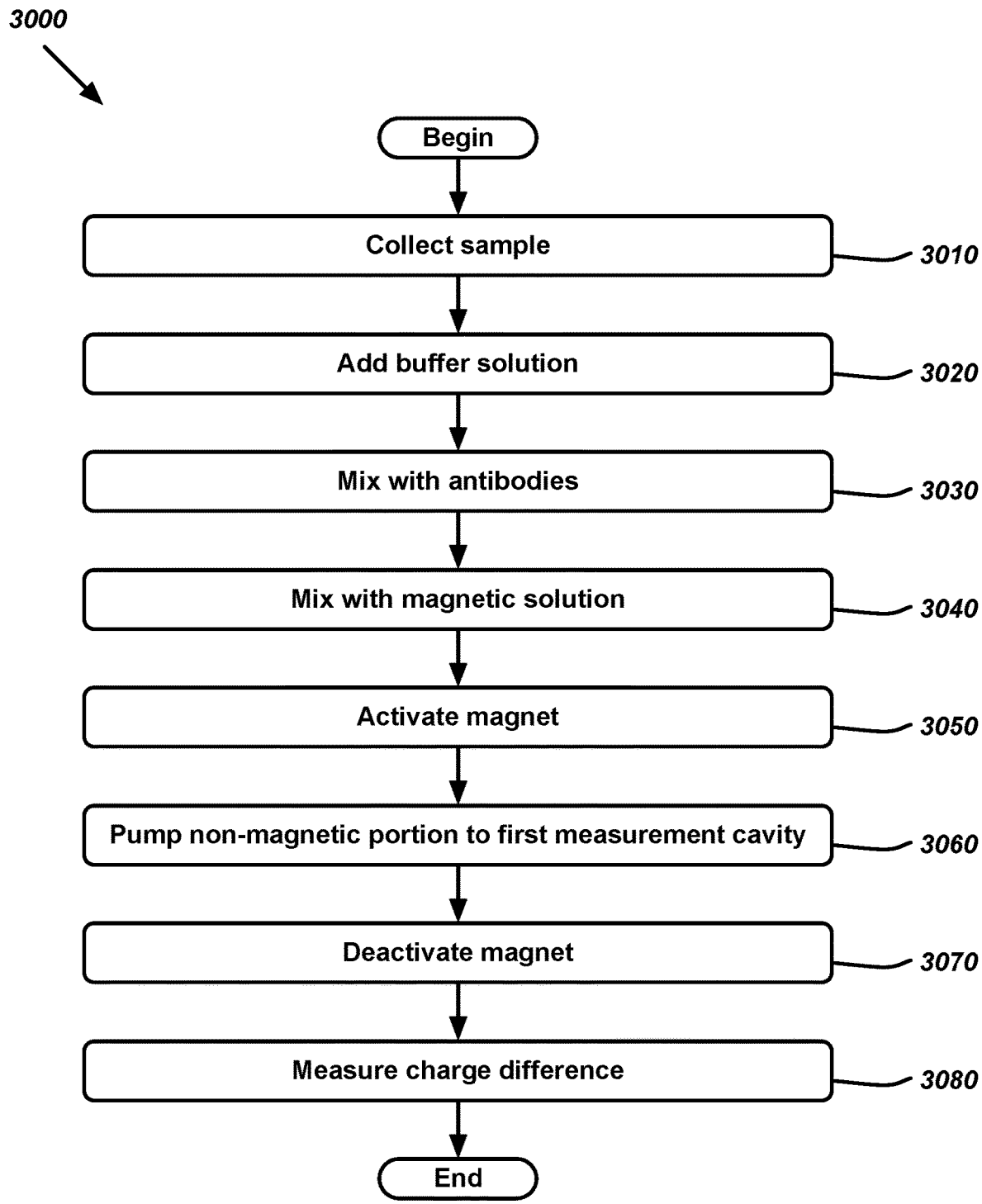
FIG. 30 illustrates a flow chart of an exemplary process that processes a sample using the sample processing module of FIG. 8.

FIG. 30 illustrates a flow chart of an exemplary process 3000 that processes a sample using the sample processing module 110 of FIG. 8. Such a process may be executed by the SCTD 100. The process may begin after a sample is taken, such as described above in reference to operation 1650 and process 1700.

As shown, process 3000 may collect (at 3010) a sample. Such a sample may be collected via sample collection element 810 using a first pump 830, first and second measurement elements 820, and a first cavity (C1) 840.

Next, the process may add (at 3020) a buffer solution to the sample. The buffer solution may be moved to the first cavity (C1) 840 using a second pump 830, third and fourth measurement elements 820, and a pre-filled cavity (BS) 850. As above, the solution may be moved between cavity (BS) and cavity (C1) several times to thoroughly mix the solution. Some portion of the mixture (usually 50%) may be retained in some embodiments (e.g., within cavity (C1)) for future analysis.

The process may then mix (at 3030) the mixture with electrically charged antibodies by moving a portion (usually 50%) of the contents of cavity (C1) to cavity (C2) while also moving the contents of cavity (AB) into cavity (C2) as well. The pre-filled cavity (AB) may include such antibodies, which may be mixed with the mixture of cavity (C1). The mixing of such elements may be performed using a combination of the pumps 830, where some pumps may act as valves at any given time while one or more pumps may be used to move the contents of various cavities along the fluid pathway to other cavities.

Next, the process may mix (at 3040) the mixture in cavity (C2) with a certain agent or protein (e.g., HAAH protein) attached to magnetic beads. Pre-filled cavity (MB) may include such a magnetic solution. The mixture may be retained in cavity (C2). The process may then activate (at 3050) the electromagnet 870 such that the magnetic beads (and associated particles) are retained in the cavity (C2).

Process 3000 may then pump (at 3060) the non-magnetic portion of the mixture in cavity (C2) to a third measurement cavity (C3). Next, the process may deactivate (at 3070) the magnet.

Finally, the process may measure (at 3080) the charge difference between the first measurement cavity (C1) and the third measurement cavity (C3) and then may end. Alternatively, different embodiments may perform various other measurements (e.g., charge, impedance or conductance, pH level, color or other visual attributes, and/or any other measurable attribute of the fluid).

The measured value may be provided to various appropriate resources, such as a processor 520, user device 510, etc.

One of ordinary skill in the art will recognize that processes 1600, 1700, 1800, 1900, 2000, 2200, 2300, 2500, 2660, and 2700 are exemplary in nature and different embodiments may perform such processes in various different ways. For instance, the various operations may be performed in different orders. As another example, some embodiments may include additional operations and/or omit various operations. Further, some embodiments may divide the processes into multiple sub-processes and/or combine multiple processes into a macro process. Some operations, and/or sets of operations may be performed iteratively, and/or based on some criteria other than those described above.

III. Computer System

Many of the processes and modules described above may be implemented as software processes that are specified as one or more sets of instructions recorded on a non-transitory storage medium. When these instructions are executed by one or more computational element(s) (e.g., microprocessors, microcontrollers, digital signal processors (DSPs), application-specific integrated circuits (ASICs), field programmable gate arrays (FPGAs), etc.) the instructions cause the computational element(s) to perform actions specified in the instructions.

In some embodiments, various processes and modules described above may be implemented completely using electronic circuitry that may include various sets of devices or elements (e.g., sensors, logic gates, analog to digital converters, digital to analog converters, comparators, etc.). Such circuitry may be able to perform functions and/or features that may be associated with various software elements described throughout.

Figure 31:
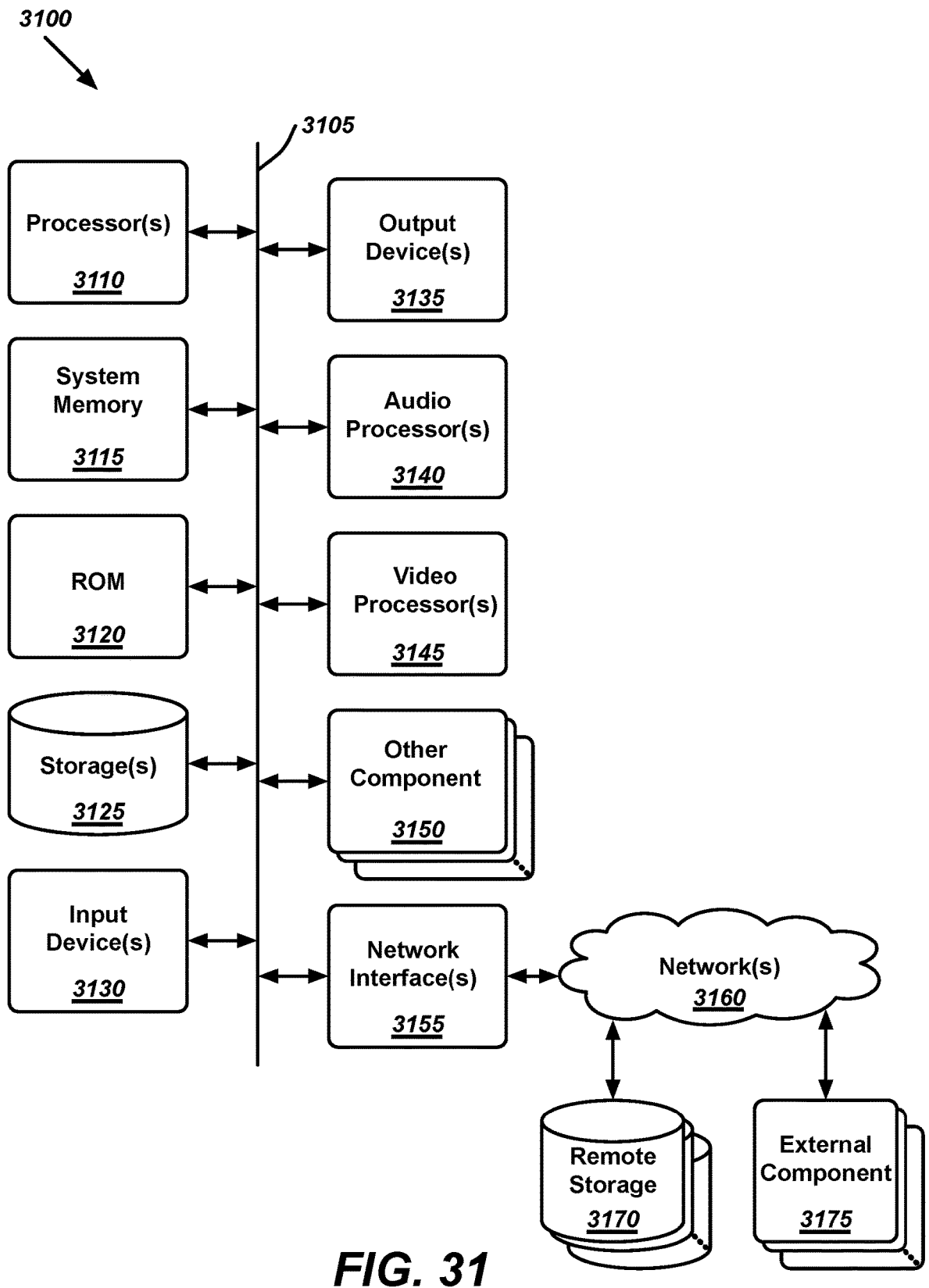
FIG. 31 illustrates a schematic block diagram of an exemplary computer system used to implement some embodiments.

FIG. 31 illustrates a schematic block diagram of an exemplary computer system 3100 used to implement some embodiments. For example, the system and devices described above in reference to FIGS. 1-15, 21, and 24 may be at least partially implemented using computer system 3100. As another example, the processes described in reference to FIGS. 16-20, 22-23, and 25-27 may be at least partially implemented using sets of instructions that are executed using computer system 3100.

Computer system 3100 may be implemented using various appropriate devices. For instance, the computer system may be implemented using one or more personal computers (PCs), servers, mobile devices (e.g., a smartphone), tablet devices, and/or any other appropriate devices. The various devices may work alone (e.g., the computer system may be implemented as a single PC) or in conjunction (e.g., some components of the computer system may be provided by a mobile device while other components are provided by a tablet device).

As shown, computer system 3100 may include at least one communication bus 3105, one or more processors 3110, a system memory 3115, a read-only memory (ROM) 3120, permanent storage devices 3125, input devices 3130, output devices 3135, audio processors 3140, video processors 3145, various other components 3150, and one or more network interfaces 3155.

Bus 3105 represents all communication pathways among the elements of computer system 3100. Such pathways may include wired, wireless, optical, and/or other appropriate communication pathways. For example, input devices 3130 and/or output devices 3135 may be coupled to the system 3100 using a wireless connection protocol or system.

The processor 3110 may, in order to execute the processes of some embodiments, retrieve instructions to execute and/or data to process from components such as system memory 3115, ROM 3120, and permanent storage device 3125. Such instructions and data may be passed over bus 3105.

System memory 3115 may be a volatile read-and-write memory, such as a random access memory (RAM). The system memory may store some of the instructions and data that the processor uses at runtime. The sets of instructions and/or data used to implement some embodiments may be stored in the system memory 3115, the permanent storage device 3125, and/or the read-only memory 3120. ROM 3120 may store static data and instructions that may be used by processor 3110 and/or other elements of the computer system.

Permanent storage device 3125 may be a read-and-write memory device. The permanent storage device may be a non-volatile memory unit that stores instructions and data even when computer system 3100 is off or unpowered. Computer system 3100 may use a removable storage device and/or a remote storage device as the permanent storage device.

Input devices 3130 may enable a user to communicate information to the computer system and/or manipulate various operations of the system. The input devices may include keyboards, cursor control devices, audio input devices and/or video input devices. Output devices 3135 may include printers, displays, audio devices, etc. Some or all of the input and/or output devices may be wirelessly or optically connected to the computer system 3100.

Audio processor 3140 may process and/or generate audio data and/or instructions. The audio processor may be able to receive audio data from an input device 3130 such as a microphone. The audio processor 3140 may be able to provide audio data to output devices 3140 such as a set of speakers. The audio data may include digital information and/or analog signals. The audio processor 3140 may be able to analyze and/or otherwise evaluate audio data (e.g., by determining qualities such as signal to noise ratio, dynamic range, etc.). In addition, the audio processor may perform various audio processing functions (e.g., equalization, compression, etc.).

The video processor 3145 (or graphics processing unit) may process and/or generate video data and/or instructions. The video processor may be able to receive video data from an input device 3130 such as a camera. The video processor 3145 may be able to provide video data to an output device 3140 such as a display. The video data may include digital information and/or analog signals. The video processor 3145 may be able to analyze and/or otherwise evaluate video data (e.g., by determining qualities such as resolution, frame rate, etc.). In addition, the video processor may perform various video processing functions (e.g., contrast adjustment or normalization, color adjustment, etc.). Furthermore, the video processor may be able to render graphic elements and/or video.

Other components 3150 may perform various other functions including providing storage, interfacing with external systems or components, etc.

Finally, as shown in FIG. 31, computer system 3100 may include one or more network interfaces 3155 that are able to connect to one or more networks 3160. For example, computer system 3100 may be coupled to a web server on the Internet such that a web browser executing on computer system 3100 may interact with the web server as a user interacts with an interface that operates in the web browser. Computer system 3100 may be able to access one or more remote storages 3170 and one or more external components 3175 through the network interface 3155 and network 3160. The network interface(s) 3155 may include one or more application programming interfaces (APIs) that may allow the computer system 3100 to access remote systems and/or storages and also may allow remote systems and/or storages to access computer system 3100 (or elements thereof).

As used in this specification and any claims of this application, the terms "computer", "server", "processor", and "memory" all refer to electronic devices. These terms exclude people or groups of people. As used in this specification and any claims of this application, the term "non-transitory storage medium" is entirely restricted to tangible, physical objects that store information in a form that is readable by electronic devices. These terms exclude any wireless or other ephemeral signals.

Each of the processes described herein, including the processes 1600, 1700, 1800, 1900, 2000, 2200, 2300, 2500, 2600, 2700, 2800, 2900, and 3000 are illustrated as a collection of blocks in a logical flow graph, which represent a sequence of operations that may be implemented in hardware, software, or a combination thereof. In the context of software, the blocks represent computer-executable instructions stored on one or more computer-readable storage media that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described blocks may be combined in any order and/or in parallel to implement the processes. Additionally, any number of the described blocks may be optional and eliminated to implement the processes.

It should be recognized by one of ordinary skill in the art that any or all of the components of computer system 3100 may be used in conjunction with some embodiments. Moreover, one of ordinary skill in the art will appreciate that many other system configurations may also be used in conjunction with some embodiments or components of some embodiments.

In addition, while the examples shown may illustrate many individual modules as separate elements, one of ordinary skill in the art would recognize that these modules may be combined into a single functional block or element. One of ordinary skill in the art would also recognize that a single module may be divided into multiple modules.

The foregoing relates to illustrative details of exemplary embodiments and modifications may be made without departing from the scope of the disclosure as defined by the following claims.

What is claimed is:

1. A sample collection and testing device for analyzing blood, the sample collection and testing device comprising:
   a controller;

a fluid flow pathway;

a pump configured to move a blood sample through the fluid flow pathway; and first and second optical fluid measurement elements located across the fluid flow pathway such that the blood sample reaches the first optical fluid measurement element before reaching the second optical fluid measurement element, each optical fluid measurement element configured to measure a light intensity of the fluid blood sample in the fluid flow pathway;

wherein the controller is configured to:

start the pump to move the blood sample in the fluid flow pathway;

receive a signal from the first optical fluid measurement element indicating a detection of a leading edge of the blood sample in the fluid flow pathway;

stop the pump in response to receiving the signal from the first optical fluid measurement element to stop the moving of the blood sample in the fluid flow pathway;

receive a plurality of light intensity measurements from the first optical fluid measurement element, each light intensity measurement measured at a corresponding point of time;

start the pump to move the blood sample in the fluid flow pathway;

receive a signal from the second optical fluid measurement element indicating a detection of a leading edge of the blood sample in the fluid flow pathway;

stop the pump in response to receiving the signal from the second optical fluid measurement element to stop the moving of the blood sample in the fluid flow pathway;

receive a plurality of light intensity measurements from the second optical fluid measurement element, each light intensity measurement measured at a corresponding point of time;

determine a travel time of the blood sample between the first and second optical fluid measurement elements; and provide a mapping of a combination of the travel time of the blood sample between the first and second optical fluid measurement elements and the light intensity measurements of the first and second optical fluid measurement elements into an indication of a coagulation of the blood sample over a time period.

2. The sample collection and testing device of claim 1, further comprising:

a sample collection element configured to receive the blood sample;

wherein the controller is configured to:

receive a signal from the sample collection element indicating a detection of the blood sample at the sample collection element; and start the pump after receiving the signal from the sample collection element.

3. The sample collection and testing device of claim 2, wherein the sample collection element and the fluid flow pathway are disposable, wherein the pump is usable over a plurality of blood samples, wherein the pump is configured to operate by receiving pulses, and wherein controller is configured to operate the pump for a plurality of pulses after the detection of the leading edge of the blood sample at a last optical fluid measurement element across the fluid flow pathway such that a quantity of blood reaches the last optical fluid measurement element without the leading edge of the blood reaching the pump.

4. The sample collection and testing device of claim 1, wherein the sample collection and testing device is a first sample collection and testing device, wherein the controller is configured to:

map the light intensity measurements into the indication of the blood coagulation based on a look up of a table generated by comparing results of blood tests of similar blood samples by a prothrombin time test (PT test) device and a second sample collection and testing device with a same configuration as the first sample collection and testing device.

5. The sample collection and testing device of claim 1, wherein the controller is configured to:

determine a viscosity of the blood sample from the plurality of light intensity measurements received from the first and second optical fluid measurement elements over the time period; and provide the mapping of the light intensity measurements into an indication of a coagulation of the blood sample based on a change in the viscosity of the blood over the time period.

6. The sample collection and testing device of claim 1, wherein the controller is configured to:

determine a viscosity of the blood sample from the plurality of light intensity measurements received from the first and second optical fluid measurement elements over the time period; and provide the mapping of the light intensity measurements into an indication of a thickness or a thinness of the blood sample based on a change in the viscosity of the blood over the time period.

7. The sample collection and testing device of claim 1, wherein each optical fluid measurement element comprises:

an emitter configured to generate an optical output; and an absorber configured to:

receive an optical input; and measure a light intensity of the optical input;

wherein the optical output of the emitter passes through a portion of the fluid flow pathway and is received as the optical input to the absorber after passing through the portion of the fluid flow pathway.

8. The sample collection and testing device of claim 1, wherein the mapping of the combination of the travel time of the blood sample between the first and second optical fluid measurement elements and the light intensity measurements of the first and second optical fluid measurement elements into the indication of the coagulation of the blood sample comprises providing a mapping to a result of a prothrombin time test (PT test) indicating the coagulation of the blood sample.

9. The sample collection and testing device of claim 1, wherein the controller is configured to:

start a digital counter when the pump is started to move the blood sample from the first optical fluid measurement element towards the second optical fluid measurement element;

stop the digital counter when the pump is stopped in response to receiving the signal from the second optical fluid measurement element; and determine the travel time of the blood sample between the first and second optical fluid measurement elements based on a value of the digital counter.

10. An automated method of measuring blood attributes, the method comprising:

by a controller of a sample collection and testing device:
   starting a pump of the sample collection and testing device to move a blood sample in a fluid flow pathway of the sample collection and testing device;
   receiving a signal from a first optical fluid measurement element of the sample collection and testing device indicating a detection of a leading edge of the blood sample in the fluid flow pathway;
   stopping the pump in response to receiving the signal from the first optical fluid measurement element to stop the moving of the blood in the fluid flow pathway;
   receiving a plurality of light intensity measurements from the first optical fluid measurement element, each light intensity measurement measured at a corresponding point of time;
   starting the pump to move the blood sample in the fluid flow pathway;
   receiving a signal from a second optical fluid measurement element of the sample collection and testing device indicating a detection of a leading edge of the blood sample in the fluid flow pathway;
   stopping the pump in response to receiving the signal from the second optical fluid measurement element to stop the moving of the blood in the fluid flow pathway;
   receiving a plurality of light intensity measurements from the second optical fluid measurement element, each light intensity measurement measured at a corresponding point of time;
   determining a travel time of the blood sample between the first and second optical fluid measurement elements; and
   providing a mapping of a combination of the travel time of the blood sample between the first and second optical fluid measurement elements and the light intensity measurements of the first and second optical fluid measurement elements into an indication of a coagulation of the blood sample over a time period.

11. The automated method of claim 10 further comprising:
   by the controller of the sample collection and testing device:
      receiving a signal from a sample collection element of the sample collection and testing device indicating a detection of the blood sample at the sample collection element; and
      starting the pump after receiving the signal from the sample collection element.

12. The automated method of claim 11, wherein the sample collection element and the fluid flow pathway are disposable, wherein the pump is usable over a plurality of blood samples, wherein the pump is configured to operate by receiving pulses, the method further comprising:
   by the controller of the sample collection and testing device, operating the pump for a plurality of pulses after the detection of the leading edge of the blood sample at a last optical fluid measurement element in the fluid flow pathway such that a quantity of blood reaches the last optical fluid measurement element without the leading edge of the blood reaching the pump.

13. The automated method of claim 10, wherein the sample collection and testing device is a first sample collection and testing device, the method further comprising:
   by the controller of the sample collection and testing device:
      mapping the light intensity measurements into the indication of the blood coagulation based on a look up of a table generated by comparing results of blood tests of similar blood samples by a prothrombin time test (PT test) device and a second sample collection and testing device with a same configuration as the first sample collection and testing device.

14. The automated method of claim 10 further comprising:
   by the controller of the sample collection and testing device:
      determining a viscosity of the blood sample from the plurality of light intensity measurements received from the first and second optical fluid measurement elements over the time period; and
      providing the mapping of the light intensity measurements into an indication of a coagulation of the blood sample based on a change in the viscosity of the blood over the time period.

15. The automated method of claim 10 further comprising:
   by the controller of the sample collection and testing device:
      determining a viscosity of the blood sample from the plurality of light intensity measurements received from the first and second optical fluid measurement elements over the time period; and
      providing the mapping of the light intensity measurements into an indication of a thickness or a thinness of the blood sample based on a change in the viscosity of the blood over the time period.

16. The automated method of claim 10, wherein the mapping of the combination of the travel time of the blood sample between the first and second optical fluid measurement elements and the light intensity measurements of the first and second optical fluid measurement elements into the indication of the coagulation of the blood sample comprises providing a mapping to a result of a prothrombin time test (PT test) indicating the coagulation of the blood sample.

17. The automated method of claim 10, wherein determining the travel time of the blood sample between the first and second optical fluid measurement elements comprises:
   by the controller of the sample collection and testing device:
      starting a digital counter when the pump is started to move the blood sample from the first optical fluid measurement element towards the second optical fluid measurement element;
      stopping the digital counter when the pump is stopped in response to receiving the signal from the second optical fluid measurement element; and
      determining the travel time of the blood sample between the first and second optical fluid measurement elements based on a value of the digital counter.

18. The automated method of claim 10, wherein determining the travel time of the blood sample between the first and second optical fluid measurement elements comprises:
   by the controller of the sample collection and testing device:
      starting an analog timer when the pump is started to move the blood sample from the first optical fluid measurement element towards the second optical fluid measurement element;

stopping the analog timer when the pump is stopped in response to receiving the signal from the second optical fluid measurement element; and determining the travel time of the blood sample between the first and second optical fluid measurement elements based on a value of the analog timer.

19. The automated method of claim 10, wherein the controller is configured to:

start an analog timer when the pump is started to move the blood sample from the first optical fluid measurement element towards the second optical fluid measurement element;

stop the analog timer when the pump is stopped in response to receiving the signal from the second optical fluid measurement element; and determine the travel time of the blood sample between the first and second optical fluid measurement elements based on a value of the analog timer.

\* \* \* \* \*